US009638771B2

(12) United States Patent
Soutome et al.

(10) Patent No.: US 9,638,771 B2
(45) Date of Patent: May 2, 2017

(54) HIGH-FREQUENCY COIL AND MAGNETIC RESONANCE IMAGING DEVICE EMPLOYING SAME

(75) Inventors: Yoshihisa Soutome, Tokyo (JP); Yoshitaka Bito, Kokubunji (JP); Hiroyuki Takeuchi, Kashiwa (JP); Tetsuhiko Takahashi, Tokyo (JP); Hisaaki Ochi, Kodaira (JP); Hideta Habara, Musashino (JP)

(73) Assignee: HITACHI, LTD., Tokyo (JP)

( * ) Notice: Subject to any disclaimer, the term of this patent is extended or adjusted under 35 U.S.C. 154(b) by 1070 days.

(21) Appl. No.: 13/811,979

(22) PCT Filed: Jul. 25, 2011

(86) PCT No.: PCT/JP2011/066860
§ 371 (c)(1),
(2), (4) Date: Jan. 24, 2013

(87) PCT Pub. No.: WO2012/023385
PCT Pub. Date: Feb. 23, 2012

(65) Prior Publication Data
US 2013/0119991 A1    May 16, 2013

(30) Foreign Application Priority Data

Aug. 17, 2010 (JP) ................................. 2010-182502

(51) Int. Cl.
*G01R 33/34* (2006.01)
*A61B 5/055* (2006.01)
(Continued)

(52) U.S. Cl.
CPC .............. *G01R 33/34* (2013.01); *A61B 5/055* (2013.01); *G01R 33/34046* (2013.01);
(Continued)

(58) Field of Classification Search
CPC .......... G01R 33/34046; G01R 33/3657; G01R 33/422; G01R 33/34; G01R 33/34084;
(Continued)

(56) References Cited

U.S. PATENT DOCUMENTS 4,916,418 A    4/1990  Rath
5,467,017 A  * 11/1995  Duerr ............... G01R 33/34061
                                                     324/318
(Continued)

FOREIGN PATENT DOCUMENTS

JP    2000-166895    6/2000
JP      3095402      8/2000
(Continued)

OTHER PUBLICATIONS

J. Thomas Vaughan et al., High Frequency Volume Coils for Clinical NMR Imaging and Spectroscopy, Magnetic Resonance in Medicine, 1994, pp. 206-218, vol. 32.
(Continued)

*Primary Examiner* — Melissa Koval
*Assistant Examiner* — Rishi Patel
(74) *Attorney, Agent, or Firm* — Baker Botts L.L.P.

(57) ABSTRACT

A technique is provided to reserve large examination space in the tunnel type MRI apparatus, without increasing production cost nor reducing significantly irradiation efficiency and homogeneity in an irradiation distribution within an imaging region. The present invention provides an RF coil unit in which four partial cylindrical coils are placed with a gap therebetween in the circumferential direction inside a cylindrical RF shield, in such a manner that two pairs of the partial cylindrical coils are opposed to each other, and magnetic fields produced by the individual partial cylindrical coils are combined, thereby producing a circularly polarized wave field or an elliptically polarized wave field. The
(Continued)

partial cylindrical coil is provided with a partial cylindrical conductor, multiple first conductors substantially parallel with the central axis of the RF shield, multiple capacitors connecting both ends of the first conductors with the partial cylindrical conductor, and a second conductor adjacent to at least one of the ends of the first conductor. The partial cylindrical coils are respectively provided with high frequency signals having a desired amplitude ratio and phase difference, while a reference frequency thereof being identical.

17 Claims, 28 Drawing Sheets

(51) Int. Cl.
    *G01R 33/345*     (2006.01)
    *G01R 33/36*     (2006.01)
    *G01R 33/422*     (2006.01)

(52) U.S. Cl.
    CPC ..... *G01R 33/3453* (2013.01); *G01R 33/3678* (2013.01); *G01R 33/34084* (2013.01); *G01R 33/365* (2013.01); *G01R 33/3657* (2013.01); *G01R 33/422* (2013.01)

(58) Field of Classification Search
    CPC .......... G01R 33/34092; G01R 33/3453; G01R 33/365; A61B 5/055
    USPC ................................................ 324/318–322
    See application file for complete search history.

(56) References Cited

U.S. PATENT DOCUMENTS

| | | | | |
|---|---|---|---|---|
| 5,777,474 A | * | 7/1998 | Srinivasan | G01R 33/34046 324/318 |
| 5,990,681 A | * | 11/1999 | Richard | G01R 33/34046 324/318 |
| 2006/0012369 A1 | * | 1/2006 | Neufeld | G01R 33/343 324/318 |
| 2006/0033497 A1 | * | 2/2006 | Chmielewski | G01R 33/34046 324/318 |
| 2006/0238198 A1 | * | 10/2006 | Nabetani | G01R 33/34076 324/318 |
| 2008/0129292 A1 | | 6/2008 | Leussler et al. | |
| 2009/0128150 A1 | | 5/2009 | Ham et al. | |
| 2012/0086452 A1 | * | 4/2012 | Dohata | G01R 33/3456 324/318 |
| 2012/0262173 A1 | * | 10/2012 | Soutome | G01R 33/34076 324/309 |
| 2013/0221968 A1 | * | 8/2013 | Habara | G01R 33/34046 324/322 |

FOREIGN PATENT DOCUMENTS

| | | |
|---|---|---|
| JP | 3471862 | 9/2003 |
| JP | 2007-511316 | 5/2007 |
| JP | 2008-67807 | 3/2008 |
| JP | 2009-539572 | 11/2009 |

OTHER PUBLICATIONS

C.-N. Chen et al., Quadrature Detection Cois-A Furter √2 Improvement in Sensitivity, Journal of Magnetic Resonance, 1983, pp. 324-327, vol. 54.

G. H. Glover et al., Comparison of Linear and Circular Polarization for Magnetic Resonance Imaging, Journal of Magnetic, 1985, pp. 255-270, vol. 64.

J. Jin et al., Analysis of Open Coils Including Shielding Effects for MRI Applications, Book of Abstracts SMRM 12th Annual Meeting and Exhibition, 1993, pp. 1354.

* cited by examiner

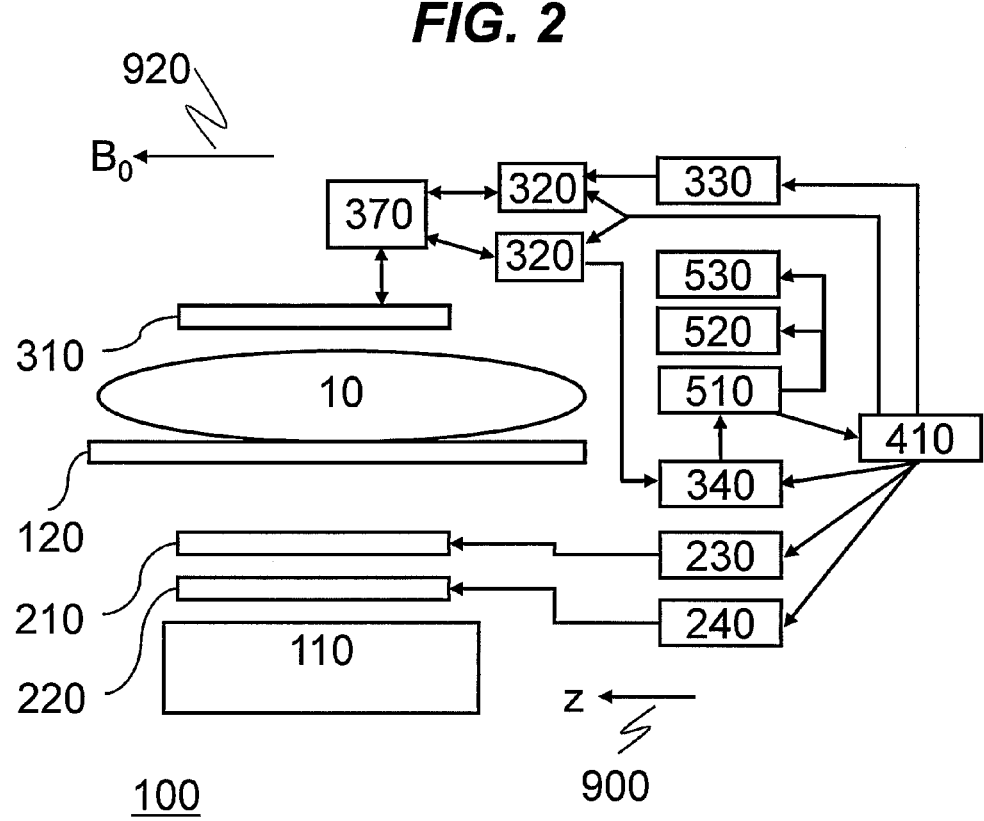

HIGH-FREQUENCY COIL AND MAGNETIC RESONANCE IMAGING DEVICE EMPLOYING SAME

TECHNICAL FIELD

The present invention relates to a magnetic resonance imaging (MRI) apparatus, and more particularly, it relates to a high frequency coil for electromagnetic wave irradiation and detection of a nuclear magnetic resonance signal.

BACKGROUND ART

The MRI apparatus is a medical diagnostic imaging apparatus which produces magnetic resonance in a nuclear spin within any slice passing transversely across an examination target, and obtains a tomographic image within the slice based on nuclear magnetic resonance signals being generated. When a high frequency coil (RF coil) irradiates a test subject placed in a static magnetic field with a high frequency magnetic field, while applying a gradient magnetic field, a nuclear spin within the test subject, for example, a nuclear spin of a hydrogen atom is excited. When the excited nuclear spin returns to the equilibrium state, a circularly polarized wave field is generated as a nuclear magnetic resonance signal. The RF coil detects this signal, and then, the signal is subjected to signal processing to create an image representing a distribution of atomic nuclei of hydrogen within a living body.

The RF coil used for the irradiation of the high frequency magnetic field is required to have a homogeneous distribution of irradiation strength and a high irradiation efficiency. It is desirable that the distribution of irradiation strength shows 70% or higher irradiation strength in an imaging region, with respect to a maximum value of the irradiation strength within the region. This is because, if the distribution of the irradiation strength is imhomogeneous, a difference may occur in the excited state of the nuclear spins depending on portions within the test subject, and this causes contrast unevenness and/or artifacts in the image being obtained.

Generally, for a cylindrical (tunnel type) MRI apparatus, there is known a cylindrical RF coil such as a birdcage coil (e.g., see Patent Document 1) and a TEM coil (e.g., see Non Patent Document 1), as a coil having a homogeneous distribution of irradiation strength, among the RF coils used for irradiation of the high frequency magnetic field.

As a method for enhancing the irradiation efficiency, there is a quadrature phase detection (QD: Quadrature Detection) method (e.g., see Patent Document 2, Non Patent Document 2, and Non Patent Document 3). The QD method uses two RF coils which carry out irradiation of the high frequency magnetic fields being orthogonal to each other, and irradiation of the high frequency magnetic fields is performed in such a manner that a phase difference in time phases of the high frequency magnetic field irradiation from the respective RF coils becomes 90 degrees. The QD method allows the circularly polarized wave field for exciting the nuclear spin of the hydrogen atom to be irradiated with a high degree of efficiency, and therefore, the irradiation strength can be enhanced theoretically by $\sqrt{2}$, compared to the case of irradiation by one RF coil. If it is converted into irradiated power, a half of the power is required only, and therefore the efficiency of the irradiated power is doubled. When the birdcage coil or the TEM coil (hereinafter, referred to as a cylindrical RF coil) is employed, two feeding ports used for the irradiation are arranged at the positions orthogonal to each other, thereby enabling irradiation of the high frequency magnetic fields according to the QD method, just by one coil.

Since the tunnel type MRI apparatus using the cylindrical RE coil is small in diameter and the length of the tunnel is long, a large person or a claustrophobic person is likely to feel more stress. In order to solve this problem, an MRI apparatus with wide examination space is required, excelling in a sense of openness with a large diameter and a short tunnel. Recently, in some cases, there are installed inside the MRI apparatus, a contrast medium injector and a nonmagnetic therapeutic instrument, so as to conduct a detailed diagnosis and treatment. Therefore, in order to reserve the space for installing various equipment to be placed in proximity to the test subject, it is requested to provide an MRI apparatus with wide examination space.

The tunnel type MRI apparatus has a structure arranging a static magnetic field magnet, a gradient magnetic field coil, an RF shield, and an RF coil, in this order from the outer side toward the inner side of the tunnel. The space inside the RF coil corresponds to the examination space for placing the test subject. Therefore, in order to expand the examination space accommodating the test subject, it seems sufficient just to increase the inner diameter of the static magnetic field magnet positioned at the outermost. However, size-up of the inner diameter of the tunnel-type static magnetic field magnet may cause a significant increase of production cost.

Generally, there is provided a distance approximately from 10 mm to 40 mm, between the RF shield and the RF coil. It is possible to consider that the examination space is made larger by reducing this distance, for instance. However, if the RF shield is placed closer to the RF coil, the RF shield current flowing on the RF shield is increased so as to cancel the high frequency magnetic field, and eventually, the irradiation efficiency of the high frequency magnetic field is significantly reduced.

Therefore, it is also conceivable to partially remove the coil conductor of the cylindrical RF coil, or to provide space between multiple RF coils, thereby partially expanding the examination space. As an example to expand the examination space by removing a part of the coil conductor, there is suggested a structure to remove a part of the conductor at opposed portions of a birdcage coil, and two semicylindrical birdcage coils are arranged in opposed manner (e.g., see Non Patent Document 4). In addition, as an example to expand the examination space by arranging two RF coils in opposed manner with space therebetween, there is suggested a partial antenna made up of a shield and a planar conductor structure (e.g., see Patent Document 3).

PRIOR ART DOCUMENT

Patent Document

Patent Document 1: U.S. Pat. No. 4,916,418 Specification
Patent Document 2: Japanese Patent No. 3095402
Patent Document 3: Japanese Patent No. 3471862

Non Patent Document

Non Patent Document 1: "High frequency volume coils for clinical nuclear magnetic resonance imaging and spectroscopy", J. T. Vaughan, et al., Magnetic Resonance in Medicine, Vol. 32, pp. 206-218 (1994)

Non Patent Document 2: "Quadrature Detection Coils—A Further $\sqrt{2}$ Improvement in Sensitivity", C. N. Chen, et al., Journal of Magnetic Resonance, Vol. 54, pp. 308-327 (1983)

Non Patent Document 3: "Comparison of Linear and Circular Polarization for Magnetic Resonance Imaging", G. H. Glover, et al., Journal of Magnetic Resonance, Vol. 64, pp. 255-270 (1985)

Non Patent Document 4: "Analysis of open coils including shielding effects for MRI applications", J. M. Jin, et al., Book of Abstracts SMRM 12th Annual Meeting and Exhibition, pp. 1354 (1993)

DISCLOSURE OF THE INVENTION

Problem to be Solved by the Invention

In the case where two semicylindrical birdcage coils are arranged in opposed manner leaving a gap therebetween, since a part of the cylindrical RF coil is removed, the high frequency magnetic field generated by the coils becomes a linearly polarized wave field being parallel to the direction in which the coils are opposed to each other. Accordingly, the irradiation power efficiency becomes half compared to the QD method. In addition, the partial antenna made up of the shield and the planar conductor structure is an RF coil intended to be used in an open type MRI apparatus in which two static magnetic field magnets are placed in opposed manner, and it is difficult to use this coil as it is, as the RF coil for the tunnel type MRI apparatus.

The present invention has been made in view of the situation above, and an object of the invention is to provide a technique to reserve large examination space in the tunnel type MRI apparatus, without increasing the production cost nor reducing significantly the irradiation efficiency and homogeneity in an irradiation distribution within an imaging region.

Means to Solve the Problem

The present invention provides an RF coil unit in which four partial cylindrical coils are placed with a gap therebetween inside a cylindrical RF shield, in such a manner that there are two pairs of partial cylindrical coils, each pair being opposed to each other, and magnetic fields produced by the individual partial cylindrical coils are combined, thereby generating a circularly polarized wave field or an elliptically polarized wave field. The partial cylindrical coil is provided with a partial cylindrical conductor, multiple first conductors substantially parallel to a central axis of the RF shield, multiple capacitors connecting both ends of each of the first conductors with the partial cylindrical conductor, and a second conductor adjacent to at least one of the ends of the first conductor. The partial cylindrical coils are respectively provided with high frequency signals having a desired amplitude ratio and a phase difference, while a reference frequency thereof being the same.

Specifically, there is provided a high frequency coil (RF coil) having a cylindrical RE shield, a first high frequency coil, and a second high frequency coil, the first high frequency coil and the second high frequency coil being placed with a gap therebetween in a circumferential direction inside the RF shield, each of the first high frequency coil and the second high frequency coil being provided with two partial cylindrical coils opposed to each other placing the central axis of the RF shield therebetween, and each of the partial cylindrical coils being provided with a partial cylindrical conductor sharing the central axis, multiple first conductors being placed inside the partial cylindrical conductor and substantially parallel to the central axis, multiple first capacitors connecting both ends of the first conductors with the partial cylindrical conductor, and at least one second conductor establishing a short-circuit between at least one end of the first conductor and one end of an adjacent first conductor.

There is further provided an RF coil unit having the aforementioned RF coil, and a high frequency signal control unit, the high frequency signal control unit having a first signal dividing and combining unit, and two second signal dividing and combining unit connected respectively to the first high frequency coil and the second high frequency coil, in which the first signal dividing and combining unit supplies high frequency signals having a phase difference of 90 degrees respectively to the two signal dividing and combining unit, and combines the high frequency signals supplied respectively from the two second signal dividing and combining unit by shifting the phase of the high frequency signal from one second signal dividing and combining unit by 90 degrees, the second signal dividing and combining unit supplies high frequency signals having the phase difference of 180 degrees respectively to two partial cylindrical coils of each of the first high frequency coil and the second high frequency coil, and combines the signals supplied from the two partial cylindrical coils by shifting the phase of one signal by 180 degrees.

There is further provided a magnetic resonance imaging apparatus provided with a static magnetic field forming unit for forming a static magnetic field, a gradient magnetic field forming unit for forming a gradient magnetic field, a high frequency magnetic field forming unit for forming a high frequency magnetic field, a transceive coil for applying the high frequency magnetic field to an examination target and detecting a nuclear magnetic resonance signal from the examination target, a signal processing unit for processing the nuclear magnetic resonance signal detected by the transceive coil, a control unit for controlling operations of the gradient magnetic field forming unit, the high frequency magnetic field forming unit, and the signal processing unit, and the aforementioned RF coil unit being used as the transceive coil.

It is further possible that the aforementioned RF coil is provided with a magnetic coupling adjusting unit for adjusting magnetic coupling between the first high frequency coil and the second high frequency coil, the magnetic coupling adjusting unit being a conductor loop, at least one second capacitor being inserted therein, each being placed in one pair of gaps positioned axial-symmetrically with respect to the central axis, among multiple gaps between the first high frequency coil and the second high frequency coil, and a value of the second capacitor may be adjusted so that no magnetic coupling occurs between the first high frequency coil and the second high frequency coil.

The magnetic coupling adjusting unit may be multiple magnetic coupling adjusting circuits each formed by serially connecting a third capacitor and an adjusting inductor, each being positioned within one pair of gaps axial-symmetrically placed with respect to the central axis, among multiple gaps between the first high frequency coil and the second high frequency coil, the third capacitor being connected to the end of the first conductor, the adjusting inductor being connected to the partial cylindrical conductor, being positioned in such a manner that the magnetic coupling occurs between the adjusting inductors respectively connected to the first high frequency coil and the second high frequency coil, and a value of mutual inductance of the adjusting inductors and a value of the third capacitor being adjusted so that no magnetic coupling occurs between the first high frequency coil and the second high frequency coil.

It is further possible that the first capacitor is adjusted in such a manner that resonance occurs in each of the partial cylindrical coils at the frequency of the high frequency signal.

EFFECT OF THE INVENTION

According to the present invention, it is possible to reserve large examination space in the tunnel type MRI apparatus, without increasing production cost nor reducing significantly the irradiation efficiency and homogeneity in the irradiation distribution within an imaging region.

BRIEF DESCRIPTION OF DRAWINGS

FIG. 2 is a block diagram showing a schematic configuration of the MRI apparatus according to the first embodiment;

BEST MODE FOR CARRYING OUT THE INVENTION

<<First Embodiment>>

Hereinafter, the first embodiment to which the present invention is applied will be explained. In all the following figures for explaining the embodiments of the present invention, the constituents having the same function are labeled the same, and tedious explanations will not be made.

Figure 1:
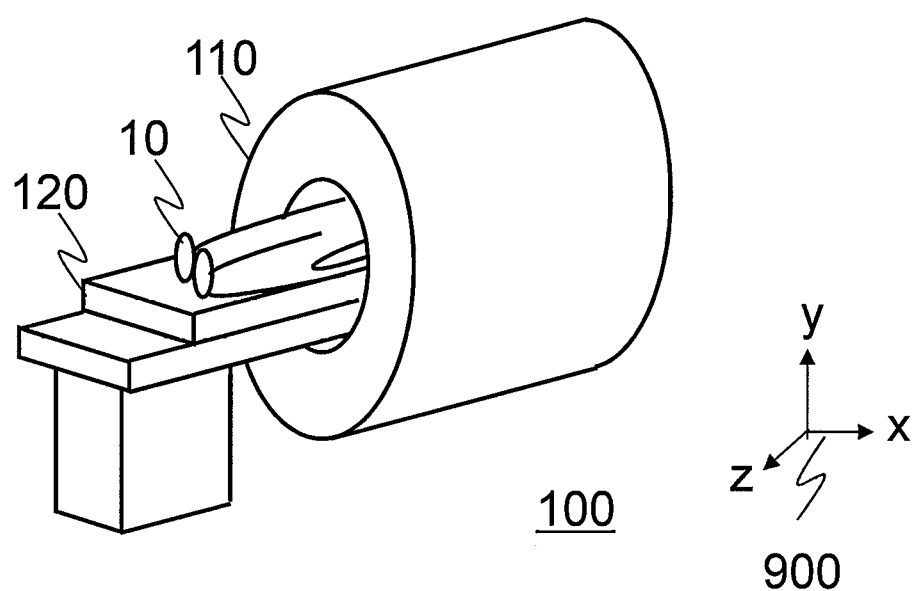
FIG. 1 is an overview of an MRI apparatus according to the first embodiment.

Firstly, the overall structure of the MRI apparatus according to the present embodiment will be explained. FIG. 1 is an overview of the MRI apparatus according to the present embodiment, and the z-axis direction of the coordinate system 900 in the figure indicates a direction of the static magnetic field. The MRI apparatus 100 according to the present embodiment is provided with a magnet 110 intended for a horizontal magnetic field system, and a patient table 120. The test subject 10 is inserted into the imaging space within the pore of the magnet 110, in the state being laid on the patient table 120, and an image is taken. In the present specification, hereinafter, the static magnetic field direction is assumed as the z-direction, a direction orthogonal to the z-direction on the plane of the patient table 120 is assumed as the x-direction, and the plane orthogonal to the patient table is assumed as the y-direction.

FIG. 2 is a block diagram showing a schematic configuration of the MRI apparatus 100 according to the present embodiment. The same constituents as those in FIG. 1 are labeled the same. In this figure, the reference numeral 920 represents the orientation of the static magnetic field ($B_0$).

The MRI apparatus 100 according to the present embodiment is provided with a magnet 110 of the horizontal magnetic field system, a gradient magnetic field coil 210, a shim coil 220 for adjusting homogeneity of the static magnetic field, a power supply for gradient magnetic field 230, a power supply for shim coil 240, a transceive coil 310 for irradiation (transmission) of a high frequency magnetic field to a test subject and simultaneously for detection (receiving) of a nuclear magnetic resonance signal generated from the test subject and outputting the detected signal as a detection signal, a transmit/receive switching unit 320 for switching ON/OFF of a high frequency signal in tune with the timing of transmitting and receiving, a high frequency signal divider/combiner 370, a transmitter 330, a receiver 340, a sequencer 410, a computer 510, a display 520, and a storage memory 530.

The gradient magnetic field coil 210 and the shim coil 220 are connected respectively to the power supply for gradient magnetic field 230 and the power supply for shim coil 240, and by using gradient magnetic field control current and shim control current supplied from the power supply for gradient magnetic field 230 and the power supply for shim coil 240, respectively, the gradient magnetic field and the shim magnetic field are applied to the imaging space.

The transceive coil 310 is connected to two transmit/receive switching units 320 via the high frequency signal divider/combiner 370, and the transmit/receive switching units 320 are respectively connected to the transmitter 330 and the receiver 340. High frequency signals for the high frequency magnetic field irradiation are applied to the transceive coil 310 via the transmit/receive switching unit 320 and the high frequency signal divider/combiner 370, thereby irradiation (transmission) of the high frequency magnetic field is performed to the test subject 10. The transceive coil 310 detects (receives) nuclear magnetic resonance signals which are generated from the test subject 10 according to the irradiated high frequency magnetic field. Those detected signals pass through the high frequency signal divider/combiner 370 and the transmit/receive switching unit 320, and the receiver 340 subjects the signals to signal amplification and detection. The signals after the detection by the receiver 340 are transferred to the computer 510 via an A/D converter (not illustrated). The storage memory 530 connected to the computer 510 stores the signals having been subjected to the detection and measuring conditions, as appropriate.

The computer 510 executes signal processing on the signals being received, such as image reconstruction. The result thereof is shown on the display 520 connected to the computer 510. The computer 510 further controls overall operations of the MRI apparatus 100.

The sequencer 410 carries out control in such a manner that each unit is operated at a timing and with strength being programmed in advance, according to instructions from the computer 510. Specifically, the sequencer 410 sends commands to the power supply for gradient magnetic field 230, the power supply for shim coil 240, the transmit/receive switching unit 320, the receiver 340, and the transmitter 330. The sequencer 410 further sets a magnetic resonance frequency that is used as a reference of detection in the receiver 340.

In the present embodiment, the shape of the transceive coil 310 and the configuration of the high frequency signal divider/combiner 370 are devised so as to expand the examination space which accommodates the test subject 10, and keep the homogeneity of the irradiation distribution at least within the test subject 10 inside the examination space to be approximately the same as conventional homogeneity, thereby maintaining approximately the same homogeneity as conventional one with regard to the irradiation distribution. Firstly, details of the RF coil device 311 used as the transceive coil 310 in the present embodiment, will be explained.

Figure 3A:
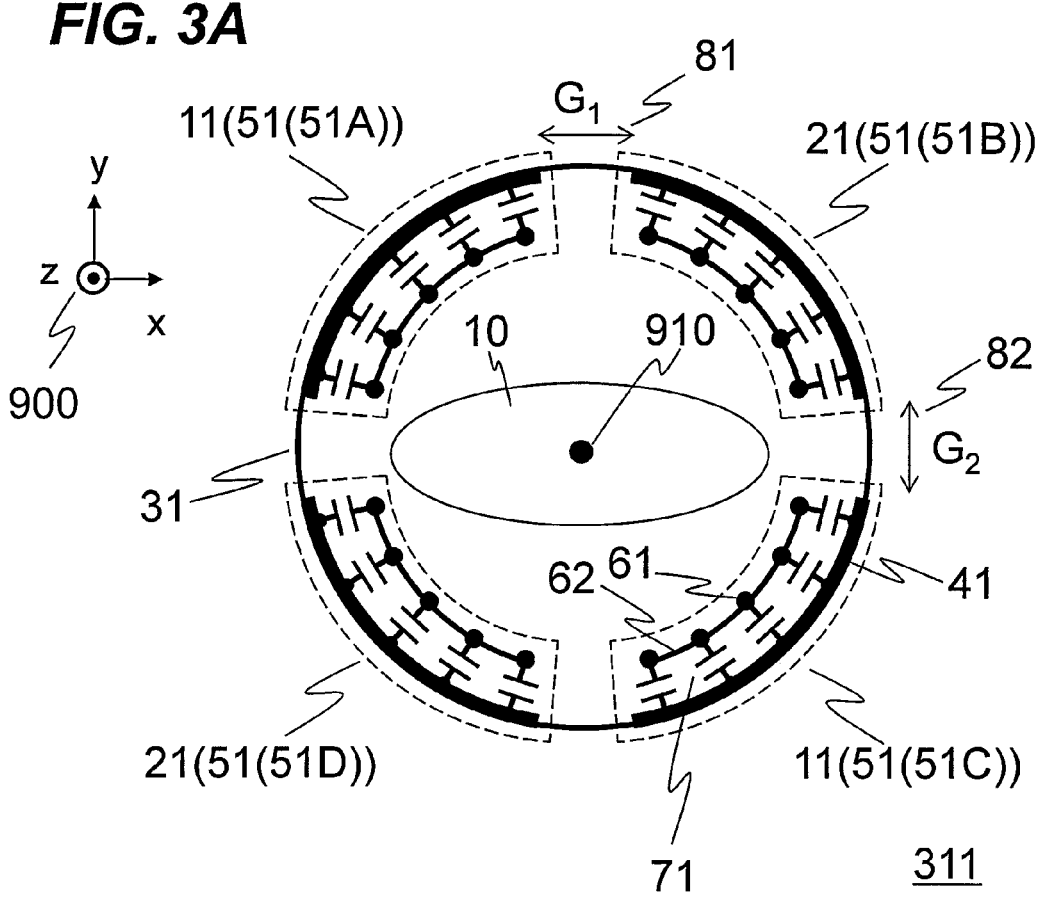
FIG. 3A illustrates an RF coil device according to the first embodiment, and shows the RF coil device viewed in the central axis direction.
Figure 3B:
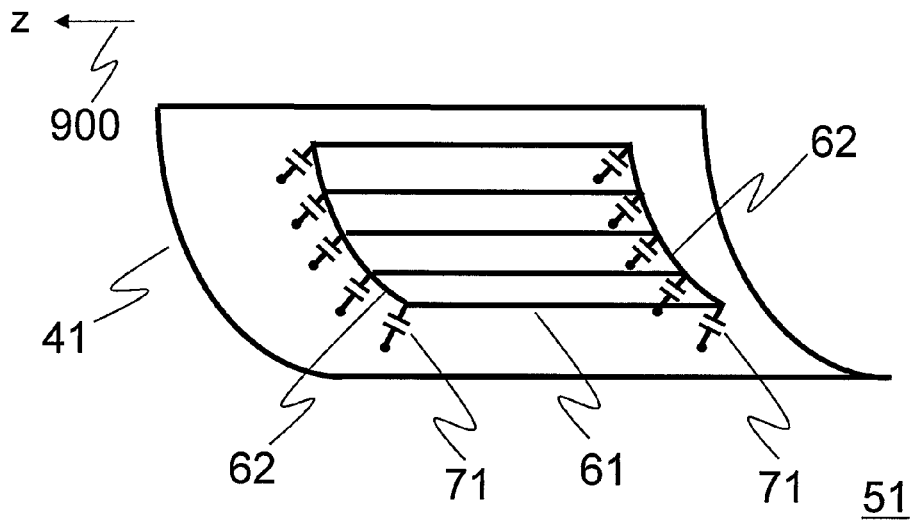
FIG. 3B illustrates an RF coil device according to the first embodiment, and shows a partial cylindrical coil being a constitutional element of the RF coil device, viewed at an oblique angle.
Figure 4A:
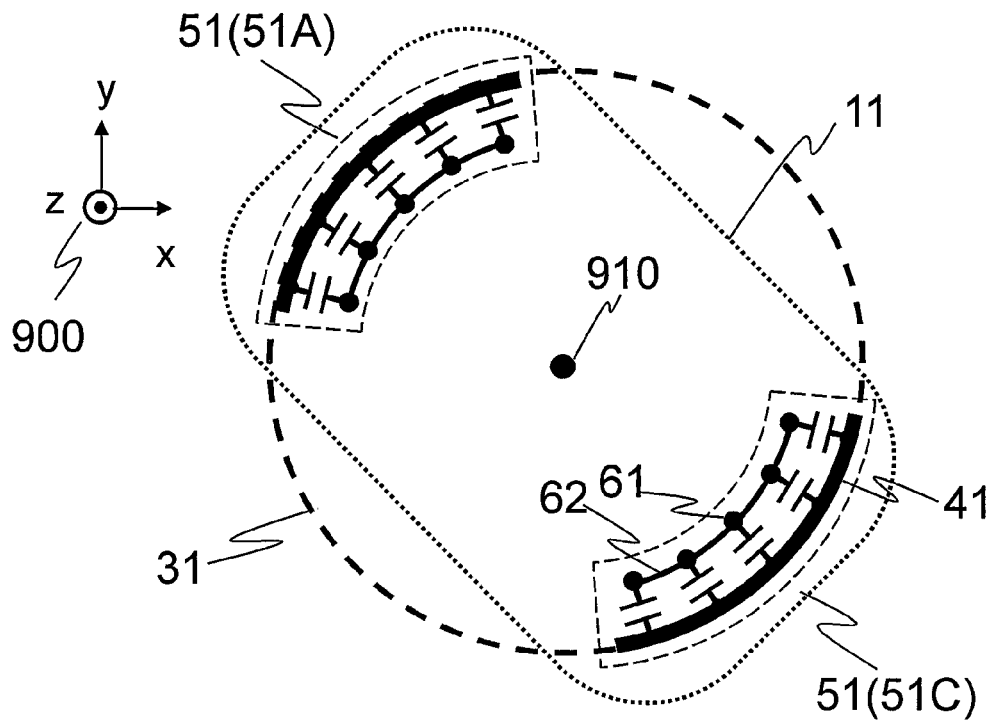
FIG. 4A illustrates a first RF coil of the RF coil device according to the first embodiment.
Figure 4B:
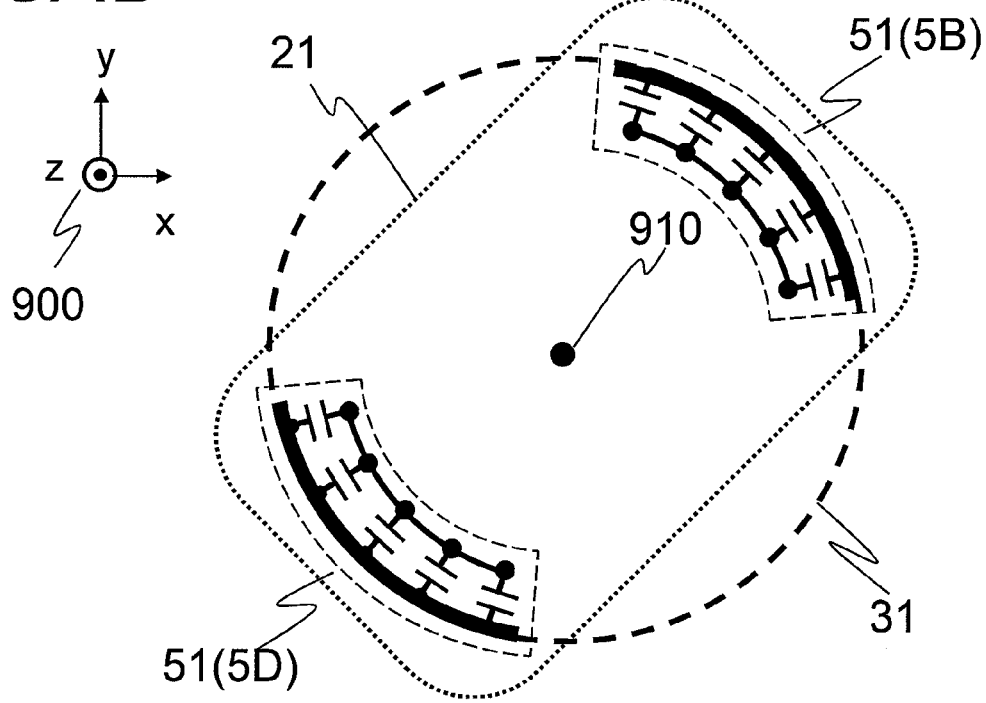
FIG. 4B illustrates a second RF coil of the RF coil device according to the first embodiment.

FIG. 3A, FIG. 3B, FIG. 4A and FIG. 4B illustrate the configuration of the RF coil device 311 of the present embodiment. FIG. 3A illustrates the RF coil device 311 viewed in the direction of the central axis 910 of an RF shield 31 (described below), FIG. 3B illustrates a partial cylindrical coil 51 (described below) being a component of the RF coil device 311 viewed at an oblique angle, FIG. 4A illustrates a first RF coil 11 (described below) in the direction of the central axis 910 of the RF shield 31 (described below), and FIG. 4B illustrates a second RF coil 21 (described below) in the direction of the central axis 910 of the RF shield 31 (described below).

As shown in FIG. 3A, FIG. 3B FIG. 4A and FIG. 4B, the RF coil device 311 is provided with the first RF coil 11, the second RF coil 21, and the RF shield 31.

As shown in FIG. 3A, the RF shield 31 is made of a cylindrical conductor having a size allowing the test subject 10 to be accommodated therein. Thickness of the cylindrical conductor of the RF shield 31 is set to be 50 μm, for instance, so as to allow the gradient magnetic field to pass through and to be shielded against the high frequency magnetic field.

As shown in FIG. 3A and FIG. 4A, the first RF coil 11 is provided with two partial cylindrical coils 51 (51A and 51C), being positioned in opposed manner placing the central axis 910 therebetween, along the circumferential direction of the inner side of the RF shield 31. Furthermore, as shown in FIG. 3A and FIG. 4B, the second RF coil 21 is provided with two partial cylindrical coils 51 (51B and 51D), being positioned in opposed manner placing the central axis 910 therebetween, along the circumferential direction of the inner side of the RF shield 31.

The first RF coil 11 and the second RF coil 21 are arranged with a gap therebetween in the inner circumferential direction of the RF shield 31. As shown in FIG. 3A, the first RF coil 11 and the second RF coil 21 are positioned mirror-symmetrically, with respect to the yz plane assumed as a mirror plane including the central axis 910. A first gap 81 being $G_1$ in length in the circumferential direction is provided between the partial cylindrical coils 51A and 51B, and between the partial cylindrical coils 51C and 51D. A second gap 82 being $G_2$ in length in the circumferential direction is provided between the partial cylindrical coils 51A and 51D, and between the partial cylindrical coils 51B and 51C. In the present embodiment, it is assumed that all the gaps in the circumferential direction, between the first RF coil 11 and the second RF coil 21, are the same. In other words, the length $G_1$ is assumed as equal to the length $G_2$.

As shown in FIG. 3B, the partial cylindrical coil 51 is provided with a partial cylindrical conductor 41, multiple first conductors 61 substantially parallel to the central axis 910, multiple first capacitors 71 respectively connecting both ends of each of the first conductors 61 with the partial cylindrical conductor 41, and multiple second conductors 62 each connecting the end of the first conductor 61 with the end of another first conductor 61 being adjacent. FIG. 3B illustrates the case that there are five first conductors 61, ten first capacitors 71, and eight second conductors 62, but the number of lines and the number of units are not limited to those numbers.

The partial cylindrical conductor 41 shares the central axis 910 with the RF shield 31, and it is arranged in such a manner as coming into contact with the inner surface (inside wall) of the RF shield 31. The first conductors 61 are placed with equal spacing in the circumferential direction of the RF shield 31, keeping a certain distance from the partial cylindrical conductor 41, in other words, on a virtual cylindrical surface sharing the central axis 910 with the RF shield 31. Thickness of the partial cylindrical conductor 41 is set to be 50 μm, so as to allow the gradient magnetic field to pass through and to be shielded against the high frequency magnetic field.

A value of the first capacitor 71 of the partial cylindrical coil 51 is adjusted so that a resonance frequency of a loop conductor 63 made up of the first conductor 61, two first capacitors 71, and the partial cylindrical conductor 41 is tuned to the magnetic resonance frequency used in the MRI apparatus 100.

By way of example, the value of the first capacitor 71 becomes 42 pF under the condition described in the following; inside the RF shield 31 being 690 mm in diameter and 1,000 min length, four partial cylindrical coils 51 (51A to 51D) each having the structure as shown in FIG. 3A and FIG. 3B are placed in such a manner that both $G_1$ and $G_2$ become 130 mm, $G_1$ being the length of the first gap 81 in the circumferential direction and $G_2$ being the length of the second gap 82 in the circumferential direction, the size of the first conductor 61 of the partial cylindrical coil 51 (51A to 51D) is 40 mm in width and 540 mm in length, the size of the second conductor is 45 mm in width and 54 mm in length, the first conductors 61 are arranged along the cylindrical surface being 624 mm in diameter sharing the central axis 910, and the resonance frequency of the loop conductor 63 is tuned to 64 MHz.

The partial cylindrical conductor 41 is electrically conductive with the RF shield 31, and therefore, it is possible to assume the partial cylindrical conductor 41 and the RF shield 31 as a single unit.

Figure 5:
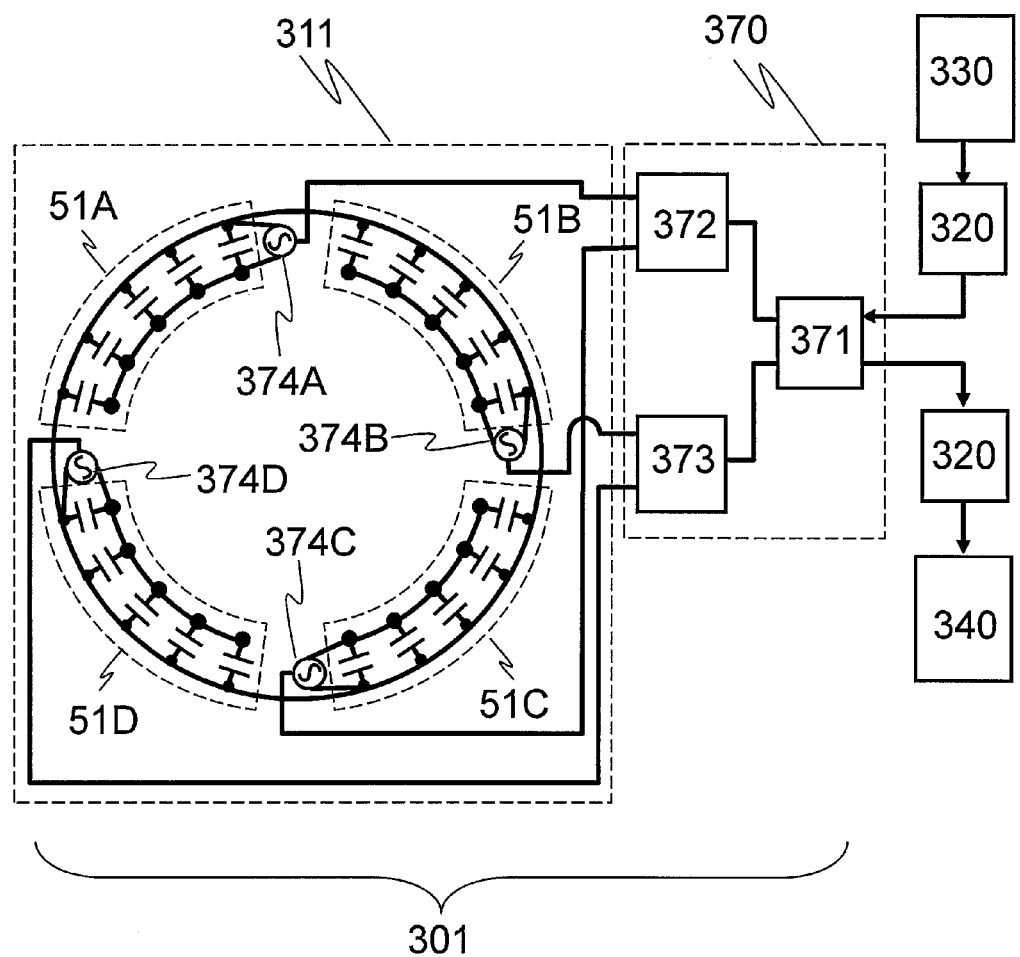
FIG. 5 illustrates a relation of connection among the RF coil device, a high frequency signal divider/combiner, a transmit/receive switching unit, a transmitter, and a receiver, according to the first embodiment.

Further as shown in FIG. 5, each of the partial cylindrical coils 51 (51A, 51B, 51C, and 51D) are respectively provided with feeding ports 374 (the first feeding port 374A, the second feeding port 374B, the third feeding port 374C, and the fourth feeding port 374D), and the feeding ports 374 are placed on the first capacitors 71. Though not illustrated in FIG. 5, there is arranged an impedance adjustment circuit between the feeding port 374 of each partial cylindrical coil 51 and the first capacitor 71. Each partial cylindrical coil 51 is supplied with high frequency signals from the high frequency signal divider/combiner 370, via the feeding port 374, and simultaneously outputs the high frequency signals being detected to the high frequency signal divider/combiner 370.

The high frequency signal divider/combiner 370 supplies each of the partial cylindrical coil 51 (51A, 51B, 51C, and 51D) constituting the RF coil device 311, with high frequency signals at a predetermined phase difference, and also cancels the phase difference to combine the high frequency signals detected by each partial cylindrical coil 51 (51A, 51B, 510, and 51D). Hereinafter, the RF coil device 311 and the high frequency signal divider/combiner 370 are referred to as an RF coil unit 301.

Next, an explanation will be made as to a detailed configuration of the high frequency signal divider/combiner 370, and a detailed connection of the RF coil device 311 with the transmitter 330 and the receiver 340, via the high frequency signal divider/combiner 370 and the transmit/receive switching unit 320.

As shown in FIG. 5, the high frequency signal divider/combiner 370 incorporates a QD hybrid 371 being the first signal dividing/combining unit, and two 0°-180° dividers/combiners being the second signal dividing/combining unit.

Those two 0°-180° dividers/combiners are respectively referred to as the first 0°-180° divider/combiner 372 and the second 0°-180° divider/combiner 373.

The QD hybrid 371 is a two-input and two-output circuit. When the input signal is one, this signal is divided into two signals at a phase difference of 90 degrees of signal waveforms, and those signals are outputted. When there are two input signals, the phase of one signal is made to shift by 90 degrees to be combined with the other signal, and the signal after being combined is outputted. The first 0°-180° divider/combiner 372 and the second 0°-180° divider/combiner 373 have a function for dividing one high frequency signal into two high frequency signals at a phase difference of 180 degrees, and a function for shifting one of two high frequency signals phases by 180 degrees to combine those signals for outputting.

The transmitter 330 and the receiver 340 are connected to the QD hybrid 371 respectively via the transmit/receive switching units 320. Two outputs from the QD hybrid 371 are connected respectively to the input of the first 0°-180° divider/combiner 372 and to the input of the second 0°-180° divider/combiner 373. Two outputs from the first 0°-180° divider/combiner 372 are connected respectively to the first feeding port 374A of the partial cylindrical coil 51A, and to the third feeding port 374C of the partial cylindrical coil 51C. Two outputs from the second 0°-180° divider/combiner 373 are connected respectively to the second feeding port 374B of the partial cylindrical coil 51B and to the fourth feeding port 374D of the partial cylindrical coil 51D.

ON/OFF control of the transmit/receive switching unit 320 is performed according to an instruction from the sequencer 410. According to the instruction, the transmit/receive switching unit 320 connected to the transmitter 330 is turned on, upon irradiation of a high frequency signal, and the transmit/receive switching unit 320 connected to the receiver 340 is turned on, upon detecting a nuclear magnetic resonance signal.

In FIG. 5, the feeding port 374 is placed on the first capacitor 71 at the outermost of the partial cylindrical coil 51. However, the position for arranging the feeding port 374 is not limited to this example. It is only required that the feeding port is positioned in such a manner that the first capacitor 71 becomes caught therein. FIG. 5 further illustrates an example that there are five first conductors 61. However, the number of lines is not limited to this example, but at least two lines are required.

Next, it will be explained that a value of the first capacitor 71 is adjusted as discussed above, and the RF coil device 311 connected to the transmitter 330 and the receiver 340 via the transmit/receive switching unit 320 and a high frequency signal divider/combiner 370 irradiates the test subject 10 with the high frequency magnetic field, and simultaneously detects a nuclear magnetic resonance signal generated from the test subject 10 and outputs as a detection signal. The transmitter 330 outputs the high frequency signal as described above, according to an instruction from the sequencer 410 which is controlled by the computer 510 based on a predetermined program. The transmit/receive switching unit 320 connected to the transmitter 330 is turned on according to the instruction from the sequencer 410.

As shown in FIG. 5, when the high frequency signal is inputted from the transmitter 330, via the transmit/receive switching unit 320, the QD hybrid 371 divides the inputted high frequency signal into two high frequency signals in such a manner that the phase difference between those signals becomes 90 degrees, and the two high frequency signals are outputted respectively to the first 0°-180° divider/combiner 372 and the second 0°-180° divider/combiner 373.

The first 0°-180° divider/combiner 372 divides the inputted high frequency signal into two high frequency signals at a phase difference of 180 degrees therebetween, and applies the two high frequency signals respectively to the first feeding port 374A and to the third feeding port 374C. The second 0°-180° divider/combiner 373 divides the inputted high frequency signal into two high frequency signals at a phase difference of 180 degrees therebetween, and applies the two high frequency signals respectively to the second feeding port 374B and to the fourth feeding port 374D.

Figure 6:
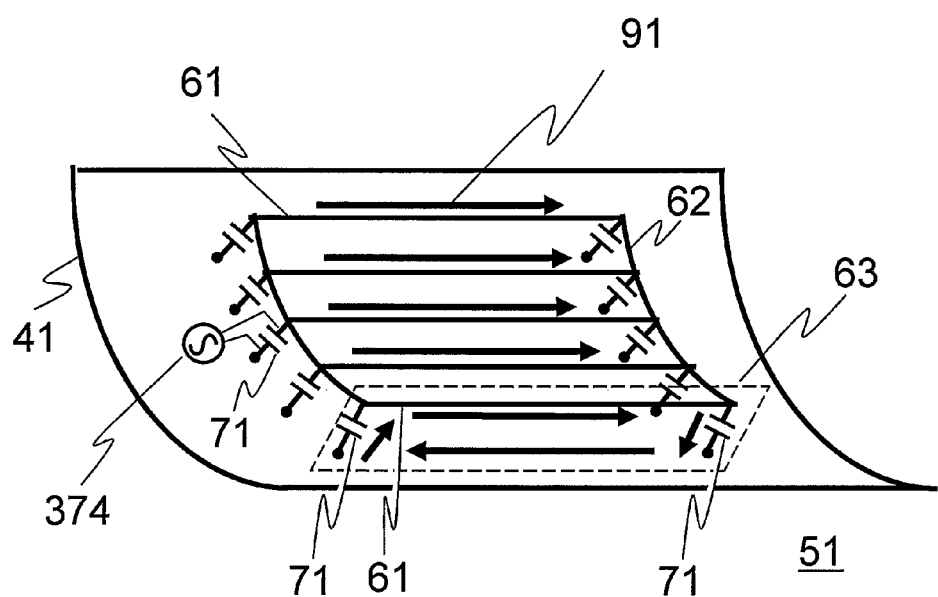
FIG. 6 illustrates current flowing in the partial cylindrical coil of the RF coil device according to the first embodiment.

With reference to FIG. 6, an explanation will be made as to the RF current which flows in the partial cylindrical coil 51, when high frequency signals are applied to the feeding port 374. When the high frequency signals are applied to the first capacitor 71 of the partial cylindrical coil 51, the loop conductor 63 made up of the first conductor 61, two first capacitors 71, and the partial cylindrical conductor 41 comes into a condition of resonance, and the RF current 91 flows along the loop conductor 63. On this occasion, since the ends of adjacent first conductors 61 are short-circuited by the second conductors 62, all the electric potential generated at the ends of the first conductors 61 which are short-circuited by the second conductors become the same. Since a distance between the first conductor 61 and the partial cylindrical conductor 41 is constant as to each of the multiple first conductors 61, all the inductance of the first conductors 61 are also the same, and all the RF current 91 flowing in the first conductors 61 have the same phase and the same amplitude.

Figure 7A:
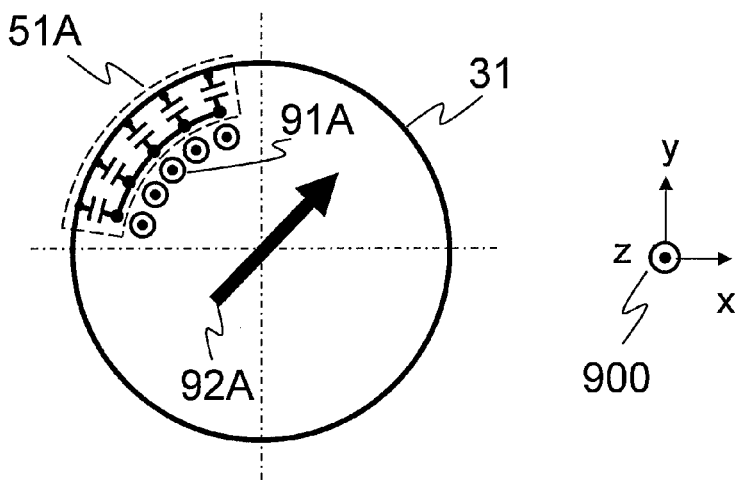
FIG. 7A illustrates current in the first RF coil of the RF coil device according to the first embodiment, and the magnetic field being generated.
Figure 7B:
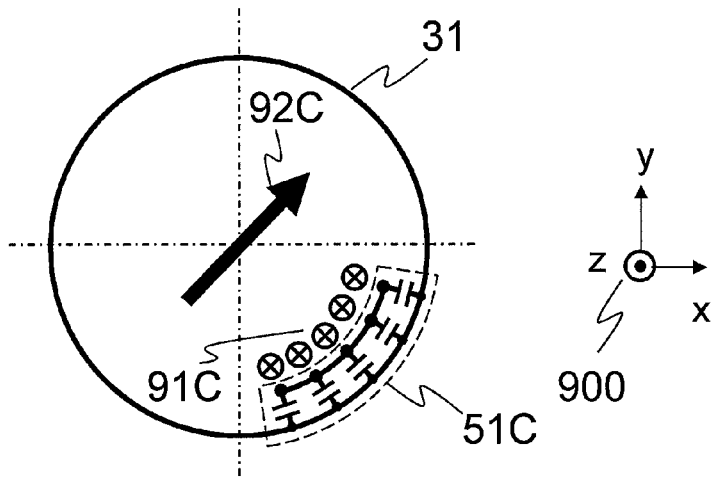
FIG. 7B illustrates current in the first RF coil of the RF coil device according to the first embodiment, and the magnetic field being generated.
Figure 7C:
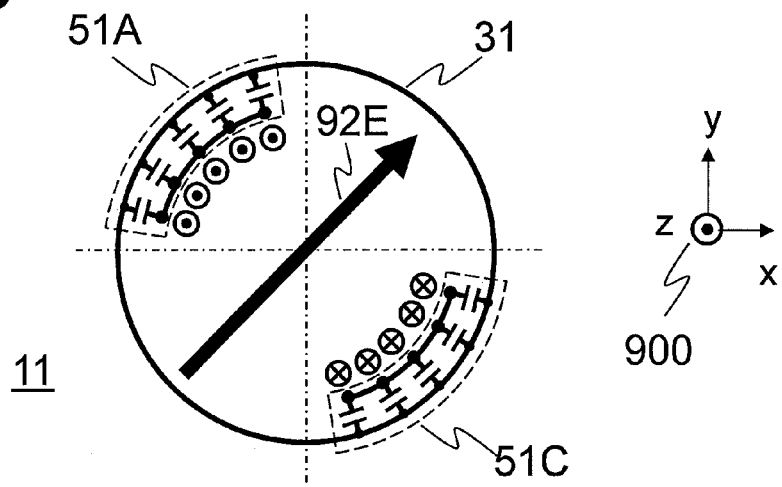
FIG. 7C illustrates current in the first RF coil of the RF coil device according to the first embodiment, and the magnetic field being generated.

With reference to FIG. 7A, FIG. 7B and FIG. 7C, the operations of the partial cylindrical coils 51A and 51C will be explained, when the high frequency signals having the phase difference 180 degrees therebetween are applied to the first feeding port 374A and the third feeding port 374C, respectively. For ease of explanation, the second RF coil 21 is not illustrated in FIG. 7A, FIG. 7B and FIG. 7C. The RF current flowing in the respective partial cylindrical coils 51A and 51C is labeled as 91A and 91C, respectively.

As shown in FIG. 7A, when the RF current 91A flows on the first conductor 61 of the partial cylindrical coil 51A, towards the front, vertically with respect to FIG. 7A on paper, and the high frequency magnetic field 92A generated by the RF current 91A becomes a linear polarized wave field which forms an angle of 45 degrees with respect to the x-axis of the coordinate system 900 at the center of the RF shield 31. This is because, the length $G_1$ of the first gap 81 in the circumferential direction is equal to the length $G_2$ of the second gap 82 in the circumferential direction, and four partial cylindrical coils 51 (51A to 51D) are arranged symmetrically with respect to the x-direction and y-direction of the coordinate system 900.

As shown in FIG. 7B, the RF current 91C flowing in the partial cylindrical coil 51C flows toward the backside with respect to the figure on paper, since the phase difference between the high frequency signals applied to the partial cylindrical coil 51A and the partial cylindrical coil 51C is 180 degrees. On this occasion, the high frequency magnetic field 92C generated by the RF current 91C shows the same orientation as the high frequency magnetic field 92A.

Therefore, as shown in FIG. 7C, the first RF coil 11 being provided with the partial cylindrical coil 51A and the partial cylindrical coil 51C generates the high frequency magnetic field 92E forming an angle of 45 degrees with respect to the x-axis of the coordinate system 900. In order to facilitate visualization, in FIG. 7A, the partial cylindrical coils 51B, 51C, and 51D are not illustrated, in FIG. 7B, the partial cylindrical coils 51A, 51B, and 51D are not illustrated, and in FIG. 7C, the partial cylindrical coils 51B and 51D are not illustrated.

Figure 8:
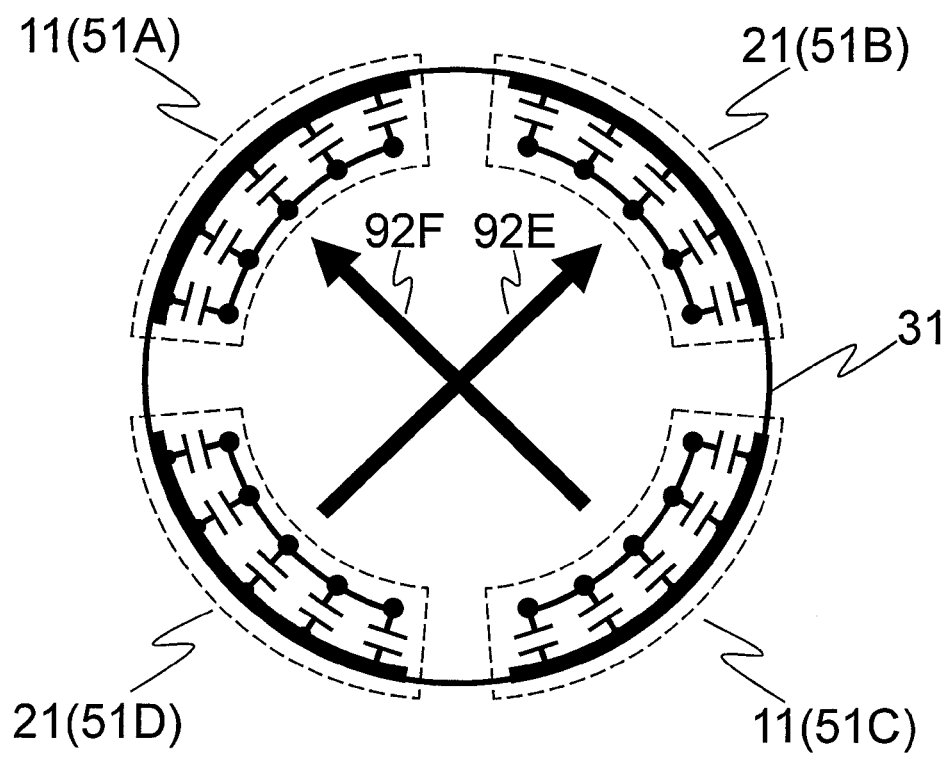
FIG. 8 illustrates the magnetic field generated by the RF coil device according to the first embodiment.

As shown in FIG. 8, the high frequency magnetic field 92F generated by the second RF coil 21 being provided with the partial cylindrical coil 51S and the partial cylindrical coil 51D, forms an angle of 90 degrees with respect to the high frequency magnetic field 92E. In the present embodiment, since the length $G_1$ of the first gap 81 in the circumferential direction is equal to the length $G_2$ of the second gap 82 in the circumferential direction, the second RF coil 21 has a structure obtained by rotating the first RF coil 11 by 90 degrees about the central axis 910 of the RF shield 31. Therefore, the high frequency magnetic field 92E generated by the first RF coil 11 and the high frequency magnetic field 92F generated by the second RF coil 21 respectively have orientations being orthogonal to each other.

Since the phase difference in the high frequency signals respectively applied to the first 0°-180° divider/combiner 372 and the second 0°-180° divider/combiner 373 is 90 degrees, the phase difference between the high frequency magnetic field 92E and the high frequency magnetic field 92F becomes 90 degrees. Therefore, the combined magnetic field of the high frequency magnetic field 92E and the high frequency magnetic field 92F becomes a magnetic field that rotates within the xy plane, when viewed from the z-direction of the coordinate system 900. Thus, the RF coil device 311 of the present embodiment receives a supply of the high frequency signals from the high frequency signal divider/combiner 370, and irradiates the inside of the RF shield 31 with rotating magnetic field, in the same manner as the QD irradiation method. Hereinafter, irradiation of the high frequency magnetic field according to the RF coil unit 301 of the present embodiment is also referred to as QD irradiation.

According to the high frequency magnetic field being irradiated, nuclear magnetic resonance signals become a magnetic field rotating within the xy plane viewed from the z-direction of the coordinate system 900, and it is emitted from the test subject 10. According to the reciprocity theorem, the RE coil device 311 detects the magnetic field rotating within the xy plane, in the same manner as the case where the high frequency magnetic field is irradiated.

Specifically, there are generated high frequency signals associated with the nuclear magnetic resonance signals, respectively on the first feeding port 374A, the second feeding port 374B, the third feeding port 374C, and the fourth feeding port 374D. As shown in FIG. 5, the high frequency signals generated on the first feeding port 374A and the third feeding port 374C are inputted into the first 0°-180° divider/combiner 372, and in here, the phase of the signal from one feeding port is made to shift by 180 degrees to combine the signals. The high frequency signals generated on the second feeding port 374B and the fourth feeding port 374D are inputted into the second 0°-180° divider/combiner 373, and the phase of the signal from one feeding port is made to shift by 180 degrees to combine the signals. Two signals combined by the first 0°-180° divider/combiner 372 and the second 0°-180° divider/combiner 373 are inputted into the QD hybrid circuit 371, and the phase of one signal is made to shift by 90 degrees to combine those signals, and then, the combined signal is outputted. Upon receiving, the transmit/receive switching unit 320 connected to the receiver 340 is turned on according to the instruction from the sequencer 410, and therefore, the output is transferred to the receiver 340 via the transmit/receive switching unit 320.

As discussed above, the RF coil device 311 of the present embodiment receives a supply of high frequency signals from the high frequency signal divider/combiner 370, irradiates the test subject 10 with the high frequency magnetic field, and also detects a nuclear magnetic resonance signal generated from the test subject 10, and outputs the nuclear magnetic resonance signal as a detection signal via the high frequency signal divider/combiner 370. Therefore, the RF coil unit 301 of the present embodiment, being provided with the RF coil device 311 and the high frequency signal divider/combiner 370 operates as a transceive coil of the MRI apparatus.

Next, it will be explained that any magnetic coupling does not occur between the first RF coil 11 and the second RF coil 21 of the RF coil device 311 of the present embodiment, in other words, those coils are in the state of decoupling upon transmitting and receiving. Generally, when two or more coils are employed, the magnetic coupling occurs in some cases between the coils depending on the coil arrangement, and this may reduce the irradiation strength of the coils and split the impedance peak into two, thereby hampering a desired irradiation of high frequency magnetic field.

Figure 9A:
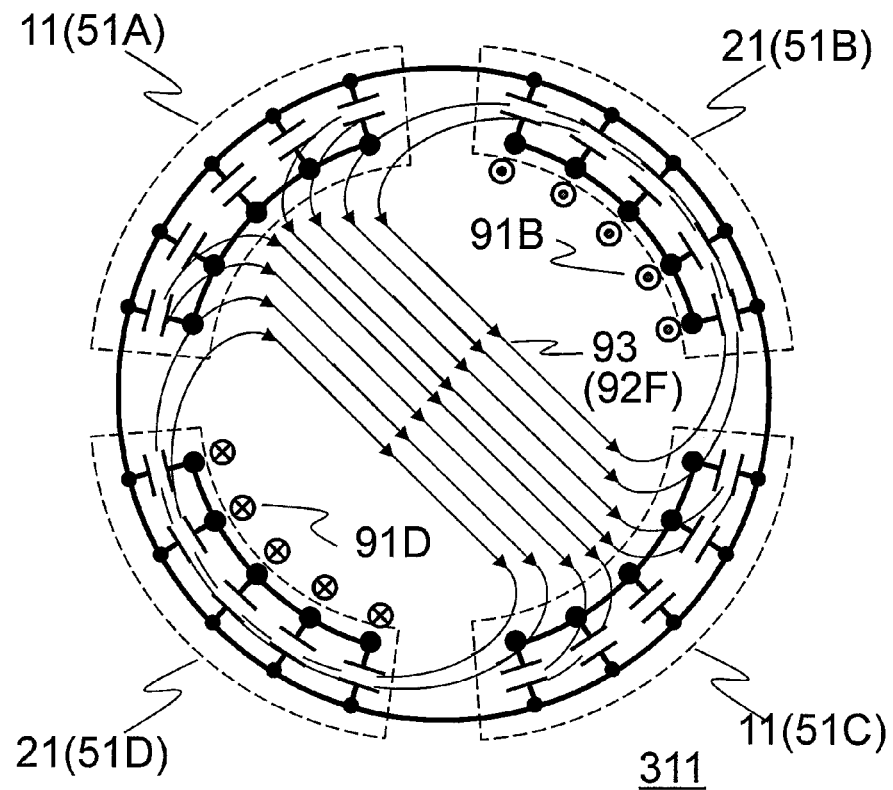
FIG. 9A illustrates the magnetic field generated by the second RF coil of the RF coil device according to the first embodiment.

As shown in FIG. 9A, upon applying the high frequency signal to the second RF coil 21, the RF current 91B and 91D flows respectively in the two partial cylindrical coils 51B and 51D constituting the second RF coil 21. On this occasion, since the phase difference of the high frequency signals applied to the two partial cylindrical coils 51B and 51D is 180 degrees, the RF current 91B and 91D flow in the directions opposite to each other. Consequently, the high frequency magnetic field 92F occurs. When the high frequency magnetic field 92F is represented as flux 93, as shown in FIG. 9A, the flux 93 proceeds along the inner wall of the RF shield 31, respectively from the two partial cylindrical coils 51B and 51D, interlinked with the two partial cylindrical coils 51A and 51C constituting the first RF coil 11, and takes a route to returning to the original partial cylindrical coils. On this occasion, the flux 93 in proximity to the central axis 910 of the RF shield 31 takes a direction parallel to the direction in which two partial cylindrical coils 51A and 51C are opposed to each other.

Figure 9B:
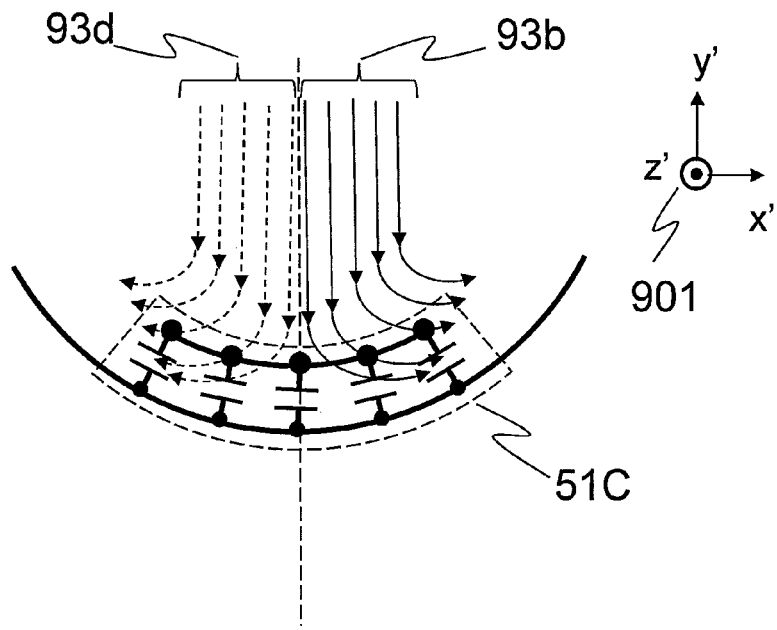
FIG. 9B illustrates the magnetic field generated by the second RF coil of the RF coil device according to the first embodiment.

FIG. 9B shows a relation between the flux 93 generated by the second RF coil 21 and the partial cylindrical coil 51C. Here, a coordinate system 901 is considered, assuming the direction in which the partial cylindrical coils 51A and 51C are opposed as y'-axis, also assuming the direction in which the partial cylindrical coils 51B and 51D are opposed as x'-axis and the direction of the central axis 910 of the RF shield 31 as z'-axis. In the coordinate system 901, the flux 93 is oriented to −y' direction in proximity to the central axis 910 of the RF shield 31, but since the RF shield 31 exists, the flux is split into two ways, +x' direction and −x' direction, in proximity to the partial cylindrical coil 51C. On this occasion, each of the flux 93$d$ oriented to −x' direction and the flux 93$b$ oriented to +x' is interlinked with the loop conductor 63 made up of the first conductor 61, two first capacitors 71, and the partial cylindrical conductor 41 of the partial cylindrical coil 51C. The direction in which the flux 93$d$ is interlinked with the loop conductor is opposite to the direction in which the flux 93$b$ is interlinked.

Figure 10A:
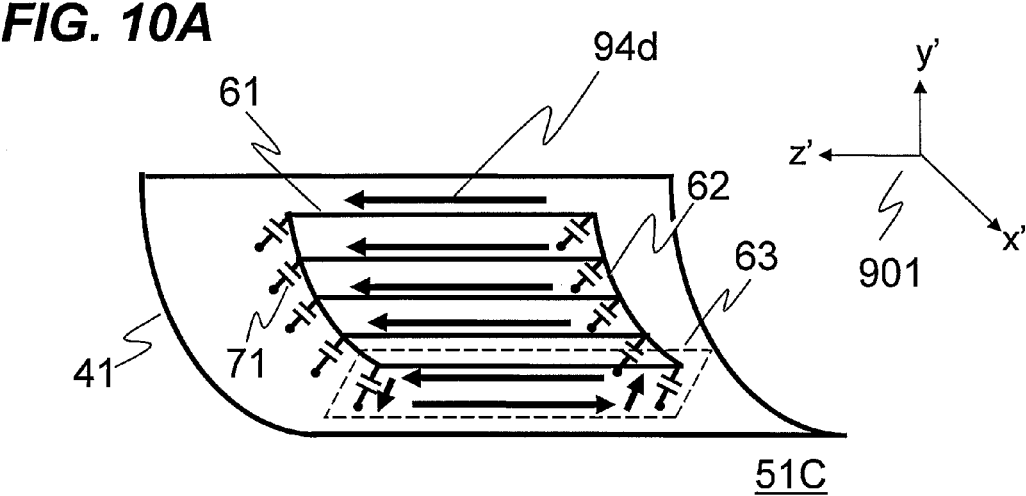
FIG. 10A illustrates inductive current flowing in the partial cylindrical coil of the RF coil device according to the first embodiment.
Figure 10B:
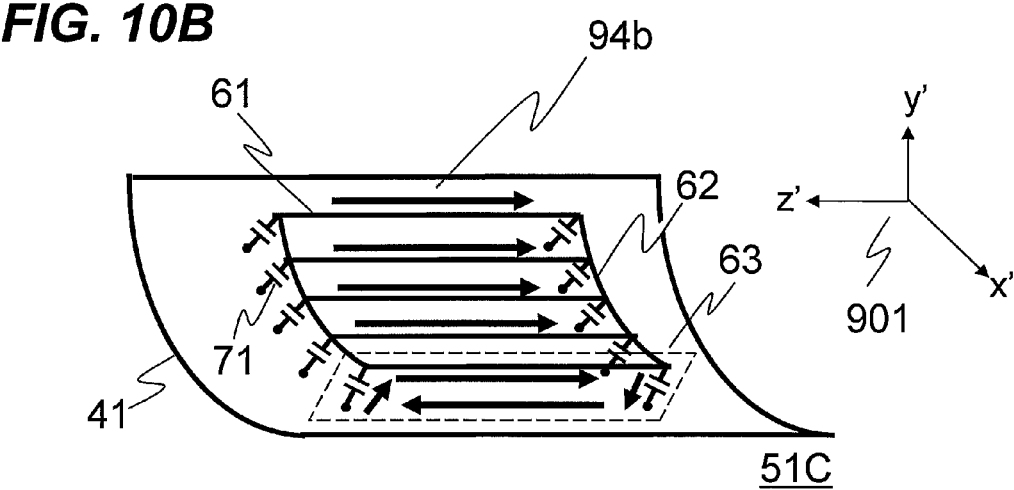
FIG. 10B illustrates inductive current flowing in the partial cylindrical coil of the RF coil device according to the first embodiment.

As shown in FIG. 10A, according to the flux 93$d$, there is generated in the partial cylindrical coil 51C, the inductive current 94$d$ flowing on the loop conductor 63 in the direction so as to generate the flux oriented to the +x' direction. On the other hand, as shown in FIG. 10B, according to the flux 93$b$, there is generated in the partial cylindrical coil 51C, the inductive current 94$b$ flowing on the loop conductor 63 in the direction so as to generate the flux oriented to the –x' direction. On this occasion, the RF current flowing on all the first conductors 61 has the same phase and the same amplitude, and therefore, the inductive current 94*d* and the inductive current 94*b* flow on all the first conductors 61. Since the distributions of the flux 93*d* and the flux 93*b* are symmetrical in the x' axis direction, the magnitude of the inductive current 94*d* and the magnitude of the inductive current 94*b* are equal to each other. However, since the direction of the inductive current 94*d* and the direction of the inductive current 94*b* flowing on the first conductors 61 are opposite to each other, the inductive current 94*d* and the inductive current 94*b* flowing on the first conductors 61 cancel each other. Therefore, due to the high frequency magnetic field generated by the second RF coil 21, the inductive current does not flow on the partial cylindrical coil 51C of the first RF coil 11.

According to the symmetric property in the layout of the four partial cylindrical coils 51A, 51B, 51C, and 51D, the inductive current does not flow either, similarly in the partial cylindrical coil 51A which is placed being opposed to the partial cylindrical coil 51C, due to the high frequency magnetic field generated by the second RF coil 21. Also, due to the high frequency magnetic field generated by the first RF coil 11, the inductive current flows neither in the partial cylindrical coils 51B nor 51D of the second RF coil 21. Therefore, magnetic coupling does not occur between the second RF coil 21 and the first RF coil 11.

A degree of expansion of the examination space and its performance as to the RF coil device 311 of the embodiment discussed above were compared with those of a conventionally known birdcage coil, and its comparison result is shown in the following. The irradiation strength and the homogeneity of the irradiation distribution were assumed as the performance. The irradiation distributions of both coils were obtained according to electromagnetic simulation.

The specifications of the RF coil device 311 used for the comparison were as the following. The RF shield 31 was 690 mm in diameter and 1,000 mm in length, the dimension of the first conductor 61 of the partial cylindrical coil 51 was 40 mm in width and 540 mm in length, and the number of the first conductors was five, the dimension of the second conductor 62 was 45 mm in width and 54 mm in length, and the number of the second conductors were eight. The first conductors 61 and the second conductors 62 were placed along the cylindrical surface being 624 mm in diameter sharing the central axis 910 of the RF shield 31. Inside the RF shield 31, four partial cylindrical coils were arranged in such a manner that both the length $G_1$ of the first gap 81 in the circumferential direction and the length $G_2$ of the second gap 82 in the circumferential direction were 130 mm. A value of the first capacitor 71 was adjusted in such a manner that the resonance frequency of the RF coil device 311 became 64 MHz.

The birdcage coil as a comparison target employed the RF shield 31 having the same dimension as the RF coil device 311, and it was a 16-rung high-pass birdcage coil being 540 mm in length, in which coil elements being 40 mm in width were arranged along the cylindrical surface being 624 mm in diameter, sharing the central axis 910 with the RF shield 31. A value of the capacitor of this birdcage coil was also adjusted in such a manner that the resonance frequency became 64 MHz.

In the RF coil device 311, a supply of the high frequency signals is received from the high frequency signal divider/combiner 370, and the QD irradiation according to the method as explained in the present embodiment was carried out, whereas in the birdcage coil, irradiation according to an ordinary QD method was carried out.

The test subject 10 inserted into the coil has a very large influence on the irradiation strength of the coil. Therefore, the irradiation strength was calculated, placing a cylindrical phantom simulating a human abdominal region, 300 mm in diameter and 500 mm in length, at the position where the center of the cylindrical phantom shared the center of the RF shield 31, and the central axis of the cylindrical phantom shared the central axis 910. The electric conductivity of the phantom was 0.6 [S/m], and the relative permittivity was 45. Since the irradiation distribution largely depends on the shape of the test subject 10 inserted into the coil, the homogeneity of the irradiation distribution was evaluated under the condition that the cylindrical phantom was not inserted (no load).

In the RF coil device 311, on a plane vertical to the central axis 910, passing through the center of the RF shield 31 (assumed as the origin point), an average irradiation strength per 1 watt in the region being 150 mm in radius about the origin point was 0.294 [A/m/√W], and a degree of homogeneity of the irradiation distribution in the same region was 3.4%. On the other hand, in the 16-rung high-pass birdcage coil, the average irradiation strength per 1 watt in the same region was 0.345 [A/m/√W], and the degree of homogeneity of the irradiation distribution was 2.3%. The degree of homogeneity of the irradiation distribution was expressed as a percentage, being a ratio of a difference between a maximum value and a minimum value to a sum of the maximum value and the minimum value of the irradiation strength within the set region.

The irradiation strength of the RF coil device 311 according to the present embodiment was 85% of the strength of the 16-rung high-pass birdcage coil that carried out the QD irradiation. The difference of 15% falls into an allowance range of the power capacity held by the amplifier of the transmitter 330, and thus the difference can be smoothed out. Therefore, it was shown that the RF coil device 311 of the present embodiment had the irradiation strength approximately equivalent to that of the conventional birdcage coil. As for the degree of homogeneity, the difference between the RF coil device 311 and the birdcage coil was just around 1% being extremely small, and it was shown that the RF coil device 311 of the present embodiment had almost equivalent irradiation distribution as that of the birdcage coil.

Figure 11:
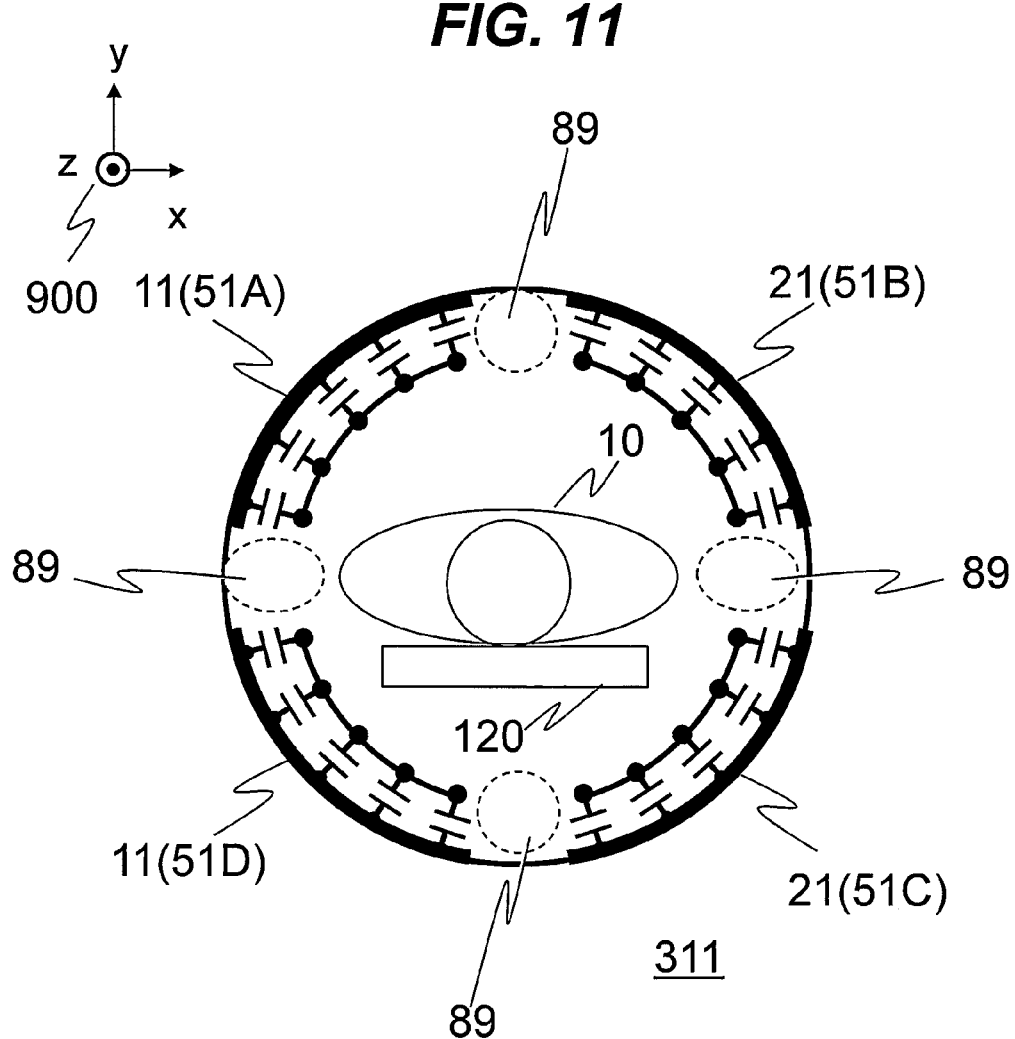
FIG. 11 illustrates examination space that is expanded by the RF coil device according to the first embodiment.

On the other hand, as for the examination space, as shown in FIG. 11, if the RF coil device 311 is employed, the space 89 is expanded in both the x-axis and y-axis directions of the coordinate system 900, compared to the case where the birdcage coil is employed. Specifically, since each of the length $G_1$ of the first gap 81 in the circumferential direction and the length $G_2$ of the second gap 82 in the circumferential direction is set to be 130 mm, when the center of the RF shield 31 is assumed as the origin point of the coordinate system 900, in the region within ±65 mm in the y-direction, the space 89 in the x-axis direction expands 66 mm in total, 33 mm to the left and 33 mm to the right, and in the region within ±65 mm in the x-direction, the space 89 in the y-axis direction expands 66 mm in total, 33 mm to the upside and 33 mm to the downside. Therefore, by using the RF coil device 311 of the present embodiment, instead of the 16-rung birdcage coil, it is possible to expand the examination space, while keeping the comparable irradiation strength and degree of homogeneity.

As discussed above, according to the present embodiment, it is possible to expand the examination space that the test subject enters, without enlarging the inner diameter of the magnet or the gradient magnetic field coil. Also, it is possible to use irradiation of the QD method (QD irradiation), and achieve the irradiation strength and the homogeneity of irradiation distribution, which are comparable with those of the conventional cylindrical RF coil.

Therefore, according to the present embodiment, it is possible to provide a transceive coil which is able to reserve larger examination space, compared to the bridge coil, in a tunnel type MRI apparatus, without significantly reducing the irradiation efficiency and the homogeneity of irradiation distribution in a desired imaging region, and without enlarging the inner diameter of the magnet or the gradient magnetic field coil.

According to the present embodiment, the transceive coil as described above is employed, and the examination space that the test subject enters is expanded, without enlarging the inner diameter of the magnet or the gradient magnetic field coil, whereby it is possible to configure an MRI apparatus which provides a sense of openness to the test subject, and an MRI apparatus which is able to reserve space for installing various equipment within the examination space.

Figure 12A:
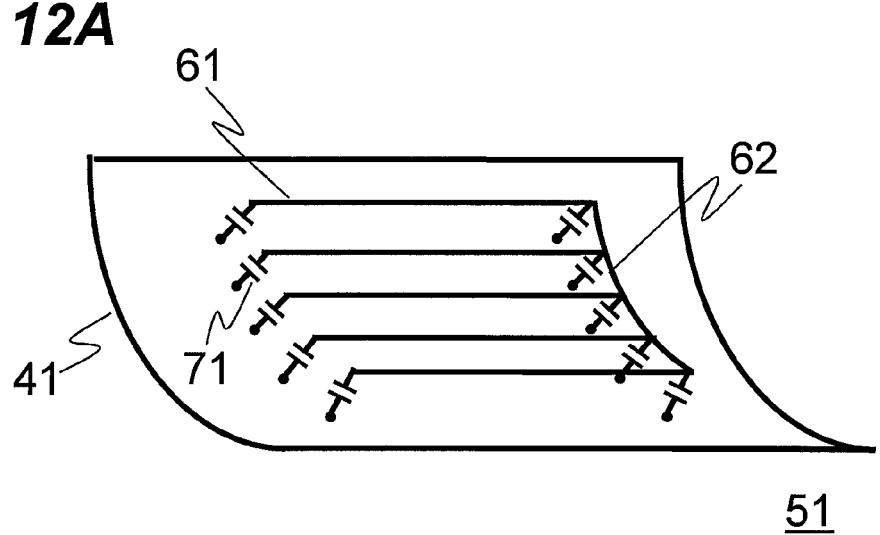
FIG. 12A illustrates modification examples of the partial cylindrical coil of the RF coil device according to the first embodiment.
Figure 12B:
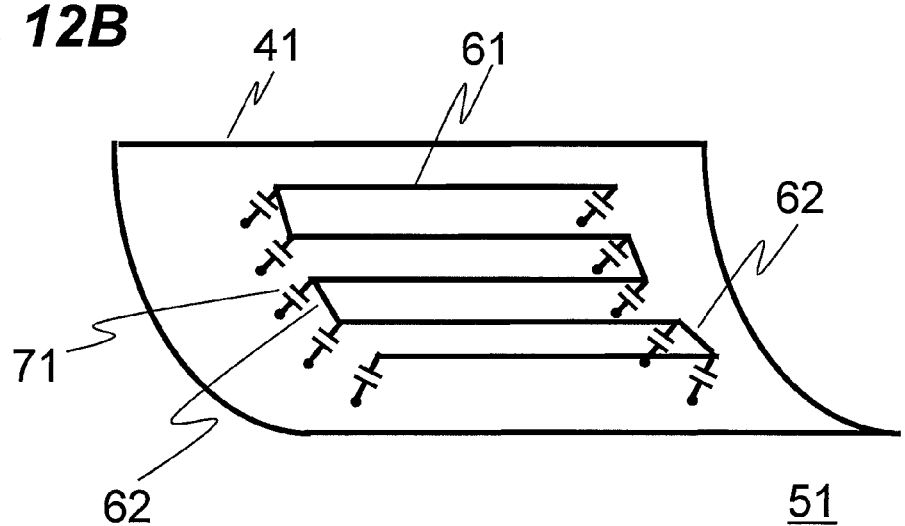
FIG. 12B illustrates modification examples of the partial cylindrical coil of the RF coil device according to the first embodiment.

It is to be noted that in the partial cylindrical coil 51 of the present embodiment, the second conductor 62 connects the ends of the first conductor 61 with the ends of the adjacent first conductor 61. It is configured as such, aiming to achieve the same phase and the same amplitude as to the RF current 91 that flows in the adjacent loop conductor 63, and this is not the only connection method for the adjacent first conductors 61. It is acceptable that at lease one end of both ends of the first conductors 61 is short-circuited by the second conductor 62. By way of example, as shown in FIG. 12A, it is possible that the ends only on one side of the first conductors 61 being adjacent to each other, are connected via the second conductor 62. As shown in FIG. 12B, it is also possible that the ends on one side of the adjacent first conductors 61 are connected via the second conductor 62 alternately like meander lines.

In the present embodiment, the thickness of the RF shield 31 and that of the partial cylindrical conductor 41 are set to be 50 μm, but their thickness is not limited to 50 μm. For example, it may be approximately a skin depth of the cylindrical conductor in a frequency of AC magnetic field that is generated when the gradient magnetic field is switched. It is only required that the thickness allows the gradient magnetic field to pass through while being shielded against the high frequency magnetic field. The RF shield 31 and the partial cylindrical conductor 41 may be a netlike conductive liner sheet. Alternatively, they may be formed by spreading multiple conductive liner sheets entirely, partially overlapped one another, the surface of the conductive liner sheets being covered with an insulator. In other words, the RF shield 31 and the partial cylindrical conductor 41 are only required to have a structure that allows the gradient magnetic field to pass through while being shielded against the high frequency magnetic field.

The configuration (inner wiring) of the high frequency signal divider/combiner 370 is not limited to the illustration of the aforementioned FIG. 5. It is only required that the relation of the amplitude and phase between the input signal and the output signal of the high frequency signal divider/combiner 370 satisfies the relation described above.

Further in the present embodiment, the phase difference between the high frequency signals applied to the first feeding port 374A and to the third feeding port 374C, respectively, and the phase difference between the high frequency signals applied to the second feeding port 374B and to the fourth feeding port 374D, respectively, is 180 degrees, but it is not necessarily 180 degrees strictly. As far as the reduction of the irradiation strength of the RF coil device 311 is within 10%, due to the reason that the phase difference is not 180 degrees, a certain angle near 180 degrees may be employed. The phase difference between the high frequency signals supplied to the first 0°-180° divider/combiner 372 and to the second 0°-180° divider/combiner 373, respectively is 90 degrees, but it is not necessarily 90 degrees strictly. As far as the reduction of the irradiation strength of the RF coil device 311 is within 10%, due to the reason that it is not 90 degrees, a certain angle near 90 degrees may be employed.

In the embodiment described above, there has been explained an example that the partial cylindrical conductor 41 of the partial cylindrical coil 51 is arranged in such a manner as coming into contact with the inner wall of the RF shield 31, and they are regarded as a single unit. However, the positional relation of both units is not limited to this example. The partial cylindrical conductor 41 may be placed at a predetermined distance from the inner wall of the RF shield 31. Alternatively, the partial cylindrical conductor 41 and the RF shield 31 may be integrated, in other words, the partial cylindrical conductor 41 is not provided, and the RF shield 31 may also serve as the partial cylindrical conductor 41.

Figure 13:
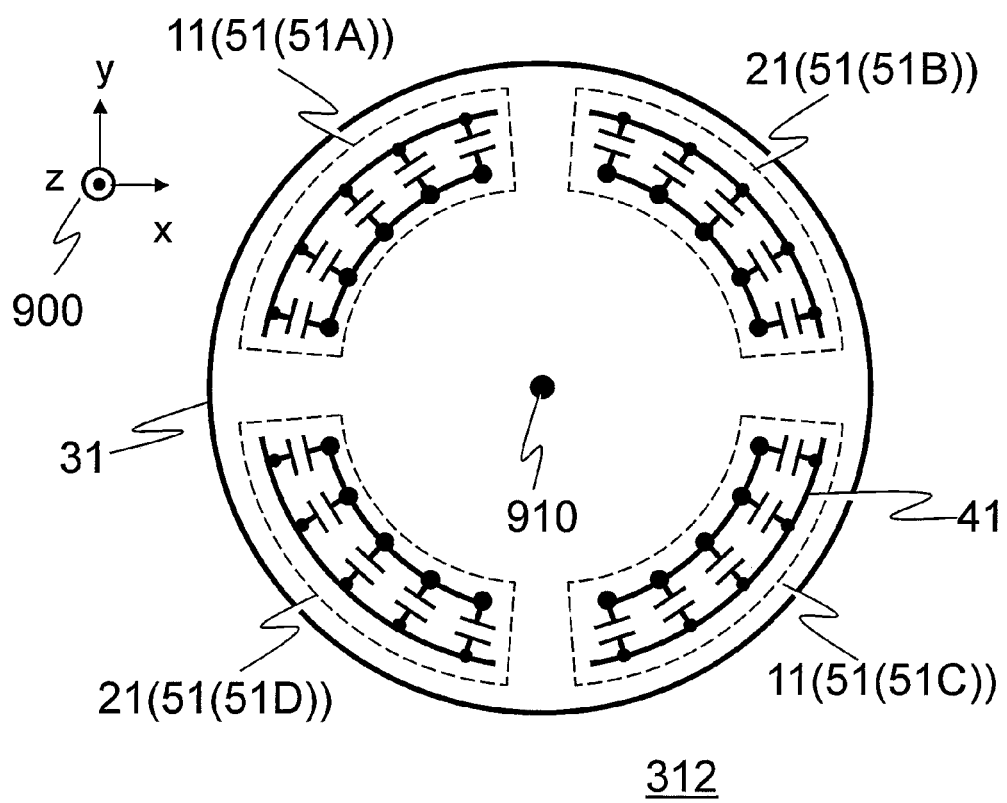
FIG. 13 illustrates an alternative example of the RF coil device according to the first embodiment.

FIG. 13 illustrates an example that the partial cylindrical conductor 41 of each of the partial cylindrical coils 51 (51A, 51B, 51C, and 51D) is placed at a predetermined distance from the inner wall of the RF shield 31 (referred to as an RF coil device 312). In this example here, it is desirable to make the distance between the partial cylindrical conductor 41 and the inner wall of the RF shield 31 as short as possible, so as not to reduce the examination space of the RF coil device 312. For example, 5 mm or less is desirable.

FIG. 13 illustrates the RF coil device 312 viewed from the direction of the central axis 910, omitting the feeding port 374. The configuration of the RF coil device 312 is different from the RF coil device 311 as shown in FIG. 3A and FIG. 3B, only in the point that the partial cylindrical conductor 41 of the partial cylindrical coil 51 is separated from the inner wall of the RF shield 31, and the remaining part of the configuration is the same.

In the RF coil device 312, the RF current 91 flowing in the partial cylindrical coil 51 flows on the partial cylindrical conductor 41, and therefore, even though the partial cylindrical conductor 41 is at a distance from the RF shield 31, there is no change in the distribution of the RF current 91. The distribution of the high frequency magnetic field generated by the partial cylindrical coil 51 is different only in the vicinity of the region where the partial cylindrical conductor 41 is separated from the inner wall of the RF shield 31, and the distribution is the same inside the partial cylindrical coil 51 and in the inner space where the test subject 10 is placed.

Therefore, the RF coil unit provided with the RF coil device 312 implements the QD irradiation, in the same manner as the RF coil unit 301 provided with the RF coil device 311. In other words, with the RF coil device 312, it is possible to achieve the same effect as produced by the RF coil device 311.

In the RF coil device 312, as shown in FIG. 13, the partial cylindrical coil 51 is positioned at a distance from the RF shield 31. Therefore, even when there occur any errors in the dimensions of the RF shield 31, it is possible to place the partial cylindrical coil 51 at a desired position, thereby enhancing the positional precision of the coil. In the case where the RF shield 31 is integrated with the gradient magnetic field coil 210, since the partial cylindrical coil 51 is separated from the RF shield 31, this may prevent the partial cylindrical coil 51 from directly receiving vibration from the gradient magnetic field coil 210. With this configuration, it is possible to prevent deterioration of the solder for fixing the capacitor provided in the partial cylindrical coil 51, thereby enhancing the stability of the coil.

As explained so far, according to the RF coil device 312 as a modification example of the present embodiment, it is possible to provide a transceive coil which is able to reserve a large examination space in the tunnel type MRI apparatus, compared to the birdcage coil, without reducing significantly the irradiation efficiency and the homogeneity of irradiation distribution within a desired imaging region, nor expanding the inner diameter of the magnet or the gradient magnetic field coil. In addition, it is possible to enhance the positional precision and stability of the transceive coil.

<<Second Embodiment>>

Next, a second embodiment to which the present invention is applied will be explained. The MRI apparatus of the present embodiment is basically the same as that of the first embodiment. However, the RF shield, the first RF coil and the second RF coil, provided in the RF coil device, are different in shape. Hereinafter, an explanation will be made as to the present embodiment, focusing on the configuration being different from the first embodiment. Also in the present embodiment, the orientation of the static magnetic field generated by the magnet 110 of the horizontal magnetic field system is assumed as the z-axis direction of the coordinate system 900.

Figure 14A:
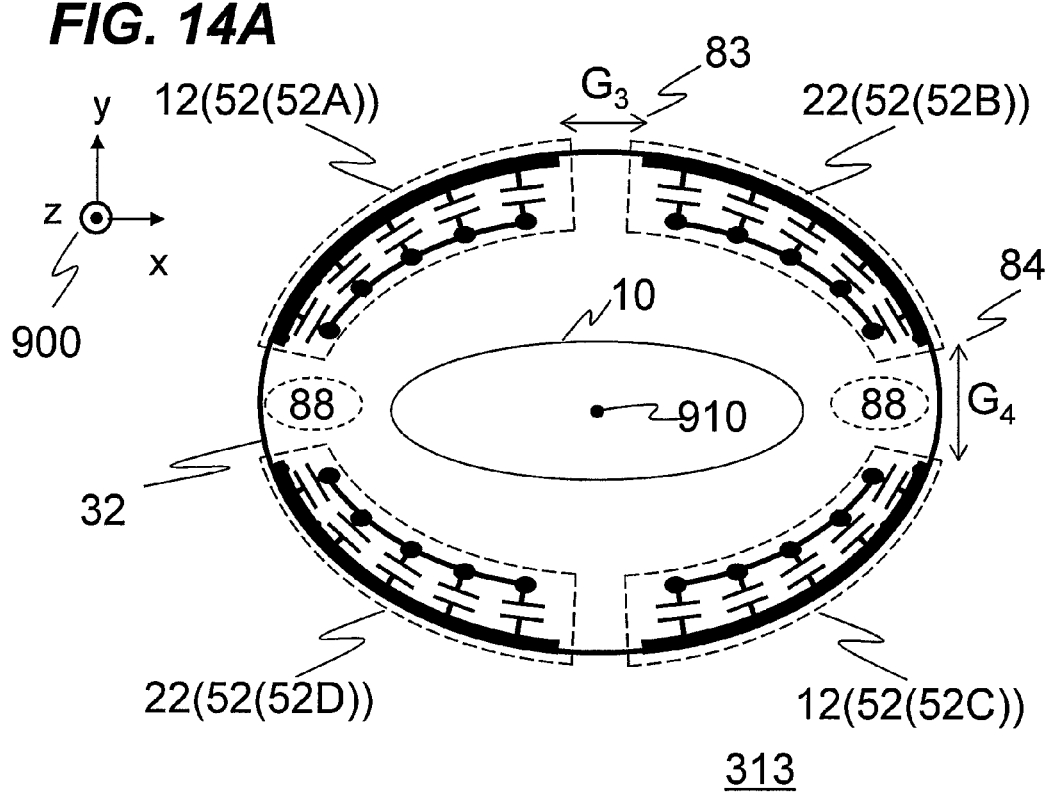
FIG. 14A illustrates the RF coil device according to a second embodiment, and shows the RF coil device viewed in the central axis direction.
Figure 14B:
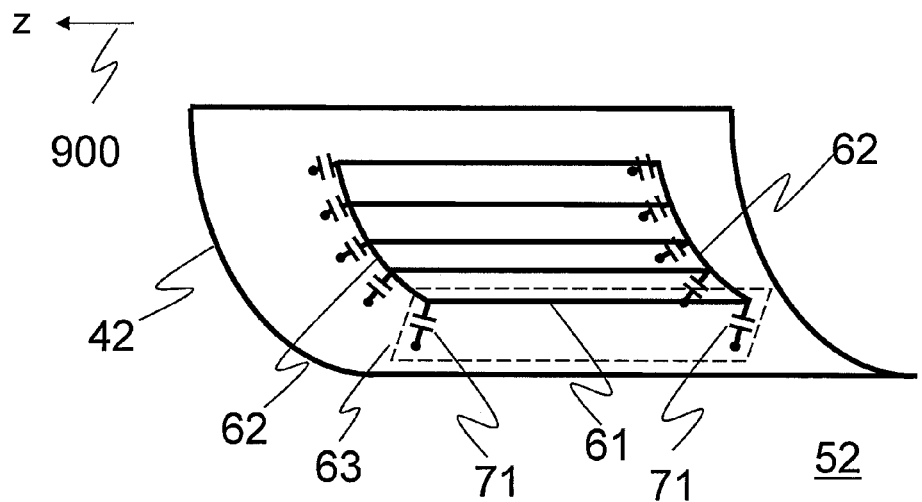
FIG. 14B illustrates the RF coil device according to a second embodiment, and shows a partial elliptic cylindrical coil being a constitutional element of the RF coil device according to a second embodiment, viewed at an oblique angle.

FIG. 14A and FIG. 14B illustrate a configuration of an RF coil device 313 according to the present embodiment. This RF coil device 313 is used as the transceive coil 310 as shown in FIG. 2. FIG. 14A illustrates the RF coil device 313 viewed in the direction of the central axis 910, FIG. 14B illustrates a partial elliptic cylindrical coil 52 viewed at an oblique angle, the coil constituting the first RF coil 12 and the second RF coil 22 of the RF coil device 313.

The RF coil device 313 of the present embodiment is provided with the first RF coil 12, the second RF coil 22, and the RF shield 32. The RF shield 32 of the present embodiment is made of an elliptic cylindrical conductor of a size accommodating the test subject 10. An ellipse as a cross section has a long axis in the x-axis direction of the coordinate system 900. The first RF coil 12 is provided with two partial elliptic cylindrical coils 52 (52A and 52C) which are arranged at opposed positions, along the circumferential direction inside the RF shield 32, placing the central axis 910 therebetween. The second RF coil 22 is provided with two partial elliptic cylindrical coils 52 (52B and 52D) which are arranged at opposed positions along the circumferential direction inside the RF shield 32, placing the central axis 910 therebetween.

The first RF coil 12 and the second RF coil 22 are placed plane-symmetrically with respect to the plane including the central axis 910. The first gap 83 having the length $G_3$ in the circumferential direction is provided each of between the partial elliptic cylindrical coils 52A and 52B, and between the partial elliptic cylindrical coils 52C and 52D. Also, the second gap 84 having the length $G_4$ in the circumferential direction is provided each of between the partial elliptic cylindrical coils 52A and 52D and between the partial elliptic cylindrical coils 52B and 52C. In the present embodiment, the length $G_3$ of the first gap 83 in the circumferential direction and the length $G_4$ of the second gap 84 in the circumferential direction are determined in such a manner that any magnetic coupling does not occur between the first RF coil 12 and the second RF coil 22. A method how to determine those lengths will be described below As shown in FIG. 14B, the partial elliptic cylindrical coil 52 is provided with a partial elliptic cylindrical conductor 42, multiple first conductors 61 being substantially parallel to the central axis 910, multiple first capacitors 71 respectively connecting both ends of the first conductor 61 with the partial elliptic cylindrical conductor 42, and multiple second conductors 62 connecting the ends of the first conductor 61 with the ends of the adjacent first conductor 61. FIG. 14B illustrates an example that there are five first conductors 61, ten first capacitors 71, and eight second conductors 62, but the number of lines and the number of units are not limited to those numbers above. The partial elliptic cylindrical conductor 42 is arranged in such a manner that it comes into contact with the inside surface (inner wall) of the RF shield 32.

Here, in the RF coil device 311 and the RF coil device 312 of the first embodiment, a distance between the RF shield 31 (the partial cylindrical conductor 41), and the first conductor 61 and the second conductor 62 of the partial cylindrical coil 51 is constant. However, in the RF coil device 313 of the present embodiment, the first conductors 61 are arranged in such a manner that the distance from the inner wall of the RF shield 32 becomes shorter, along with being positioned away from the central axis of the RF shield 32 (partial elliptic cylindrical conductor 42) in the long axis direction. In other words, in the present embodiment, elements are placed in such a manner that the distance between the first conductor 61 and the second conductor 62 of the partial elliptic cylindrical coil 52, and the RF shield 32 (partial elliptic cylindrical conductor 42) becomes narrower along with being positioned away from the central axis 910 in the x-axis direction. It is to be noted here that the first conductors 61 are arranged with equal spacing in the circumferential direction, in the same manner as the first embodiment.

The partial elliptic cylindrical coils 52A and 52C constituting the first RF coil 12, and the partial elliptic cylindrical coils 52B and 52D constituting the second RF coil 22, respectively have shapes being rotationally symmetric at an angle of 180 degrees, with respect to the central axis 910.

As shown in FIG. 14A, in the RF coil device 313 of the present embodiment, if the short axis (a diameter in the y-axis direction) of the RF shield 32 is the same length as the diameter in the y-axis direction of the RF shield 31 of the first embodiment, the diameter of the x-axis direction is longer than the diameter of the RF shield 31. Therefore, compared to the RF coil device 311, the space 88 between the test subject 10 and the RF shield 32 is expanded more.

In the present embodiment, each value of the multiple first capacitors 71 arranged in the partial elliptic cylindrical coil 52 of the RF coil device 313 is adjusted depending on the position being arranged. A method for the adjustment will be explained in the following.

It is assumed that each of multiple loop conductors (five in FIG. 14B) as a loop conductor 63, made up of the first conductor 61, two first capacitors 71, and the partial elliptic cylindrical coil 42, in the state where the second conductors 62 of the partial elliptic cylindrical coil 52 are removed. Firstly, as to each of the loop conductors 63, each value of the first capacitor 71 is adjusted in such a manner that all the resonance frequencies of the loop conductors 63, when each operates as a single unit, become the same. Next, connection is established with the second conductor 62, and while maintaining the ratio of the values of the first capacitors 71 being adjusted, the value of each of the first capacitors 71 is further adjusted so as to be tuned to the magnetic resonance frequency used in the RF coil device 313.

In the present embodiment, the partial elliptic cylindrical coil 52 places elements in such a manner that the distance between the first conductor 61 and the partial elliptic cylindrical conductor 42 becomes narrower along with being positioned away from the central axis 910 in the x-axis direction. As the first conductor 61 approaches the partial elliptic cylindrical conductor 42, a value of the inductance of the first conductor 61 becomes lower. And thus, in the present embodiment, along with being positioned toward outside in the x-axis direction away from the central axis 910, the value of the inductance of the first conductor 61 becomes lower. Therefore, when the values of the first capacitors 71 are adjusted so that the resonance frequencies of the respective loop conductors 63 are tuned to one another, there is a tendency that the values of the first capacitors 71 become larger along with being positioned away from the central axis 910 in the x-axis direction.

In the RF coil device 313 of the present embodiment, the placement of each feeding port, and the connection with the transmitter 330 and the receiver 340, via the high frequency signal divider/combiner 370 and the transmit/receive switching unit 320 are the same as those in the first embodiment as shown in FIG. 5. In other words, though not illustrated in FIG. 14A and FIG. 14B, the partial elliptic cylindrical coil 52A is provided with the first feeding port, the partial elliptic cylindrical coil 52B is provided with the second feeding port, the partial elliptic cylindrical coil 52C is provided with the third feeding port, and the partial elliptic cylindrical coil 52D is provided with the fourth feeding port, and each receives a supply of high frequency signals and detects the high frequency magnetic field being generated. Each feeding port is placed at the position where the first capacitor 71 becomes caught in the feeding port.

Next, an explanation will be made as to the RF coil device 313 being adjusted as described above, which irradiates the test subject 10 with a high frequency magnetic field, detects a nuclear magnetic resonance signal generated from the test subject 10, and outputs the signal as a detection signal.

As described above, the relation of connection between the RF coil device 313 and the transmitter 330 is similar to that of the first embodiment. Therefore, the high frequency signals applied from the transmitter 330 are distributed into four, by the high frequency signal divider/combiner 370, and applied respectively to the first feeding port, the second feeding port, the third-feeding port, and the fourth feeding port of the RF coil device 313. On this occasion, the phase difference between the signals respectively applied to the first feeding port and the third feeding port, and the phase difference between the signals respectively applied to the second feeding port and the fourth feeding port are both 180 degrees, and the phase difference between the signals respectively applied to the first feeding port and the second feeding port becomes 90 degrees.

As in the case of the first embodiment, the phase of the RF current which flows when the high frequency signals are respectively applied to the feeding ports is the same in the multiple first conductors 61 of the partial elliptic cylindrical coil 52. However, there is a tendency that the amplitude of the RF current becomes larger, along with being positioned toward outside in the x-axis direction away from the central axis 910. This is because, the value of the first capacitor 71 becomes larger along with positioned toward outside in the x-axis direction away from the central axis 910, simultaneously the second conductor 62 establishes a short-circuit on the ends of the adjacent first conductors, thereby keeping the potential constant on the ends of the first conductors being short-circuited.

Figure 15A:
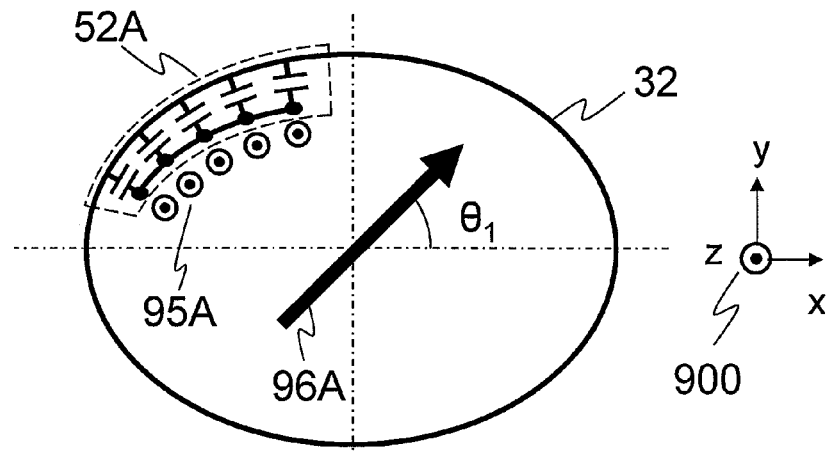
FIG. 15A illustrates current in the first RF coil of the RF coil device according to the second embodiment, and the magnetic field being generated.
Figure 15B:
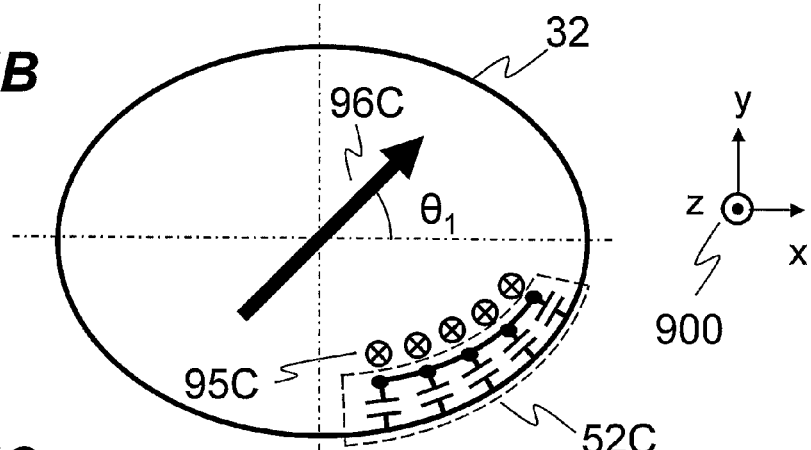
FIG. 15B illustrates current in the first RE coil of the RF coil device according to the second embodiment, and the magnetic field being generated.
Figure 15C:
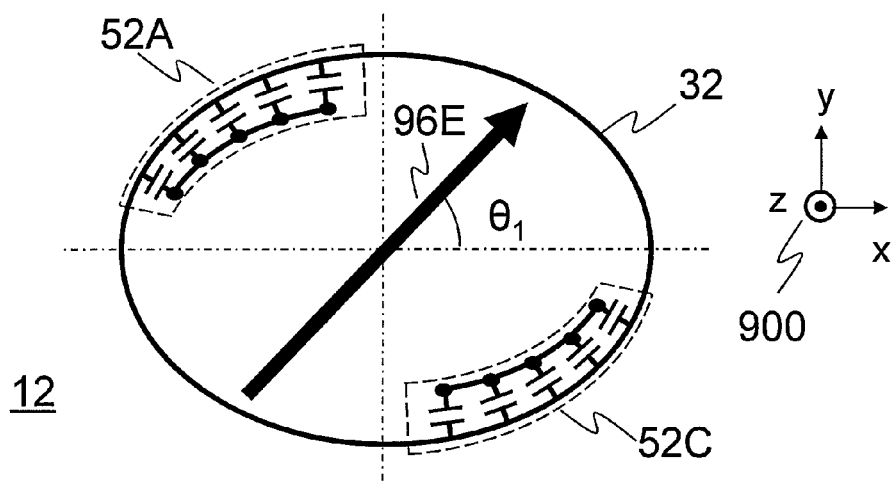
FIG. 15C illustrates current in the first RF coil of the RF coil device according to the second embodiment, and the magnetic field being generated.

With reference to FIG. 15A, FIG. 15B and FIG. 15C, operations of the partial elliptic cylindrical coils 52A and 52C will be explained, when the high frequency signals with the phase difference of 180 degrees between each other are applied to the first feeding port and the third feeding port, respectively. For ease of explanation, the partial elliptic cylindrical coils 52B, 52C, and 52D are not illustrated in FIG. 15A, the coils 52A, 52B, and 52D are not illustrated in FIG. 15B, and the second RF coil 22 is not illustrated in FIG. 15C.

If it is assumed that when high frequency signals are applied to the first feeding port, the RF current 95A having the same phase and whose amplitude becomes larger along with positioned toward outside in the x-axis direction away from the central axis 910, flows in the multiple first conductors 61 of the partial elliptic cylindrical coil 52A, in the direction to the front vertically with respect to the FIG. 15A on paper, the high frequency magnetic field 96A at the center of the RF shield 32 is generated in the direction forming the angle $\theta_1$ with respect to the x-axis of the coordinate system 900.

Since the phase difference between the high frequency signals respectively applied to the partial elliptic cylindrical coil 52A and the partial elliptic cylindrical coil 52C is 180 degrees, the RF current 95C in the partial elliptic cylindrical coil 52C flows toward the backside vertically with respect to FIG. 15B on paper, having the same phase and with the amplitude which becomes larger along with positioned toward outside in the x-axis direction away from the central axis 910. On this occasion, the high frequency magnetic field 96C generated by the RF current 95C indicates the same orientation as the high frequency magnetic field 96A, since the shapes of the partial elliptic cylindrical coil 52A and the partial elliptic cylindrical coil 52C have a 180-degree rotational symmetrical relation with respect to the central axis 910.

Therefore, as shown in FIG. 15C, the first RF coil 12 made up of the partial elliptic cylindrical coil 52A and the partial elliptic cylindrical coil 52C generates the high frequency magnetic field 96E at an angle $\theta_1$ with respect to the x-axis of the coordinate system 900.

Figure 16:
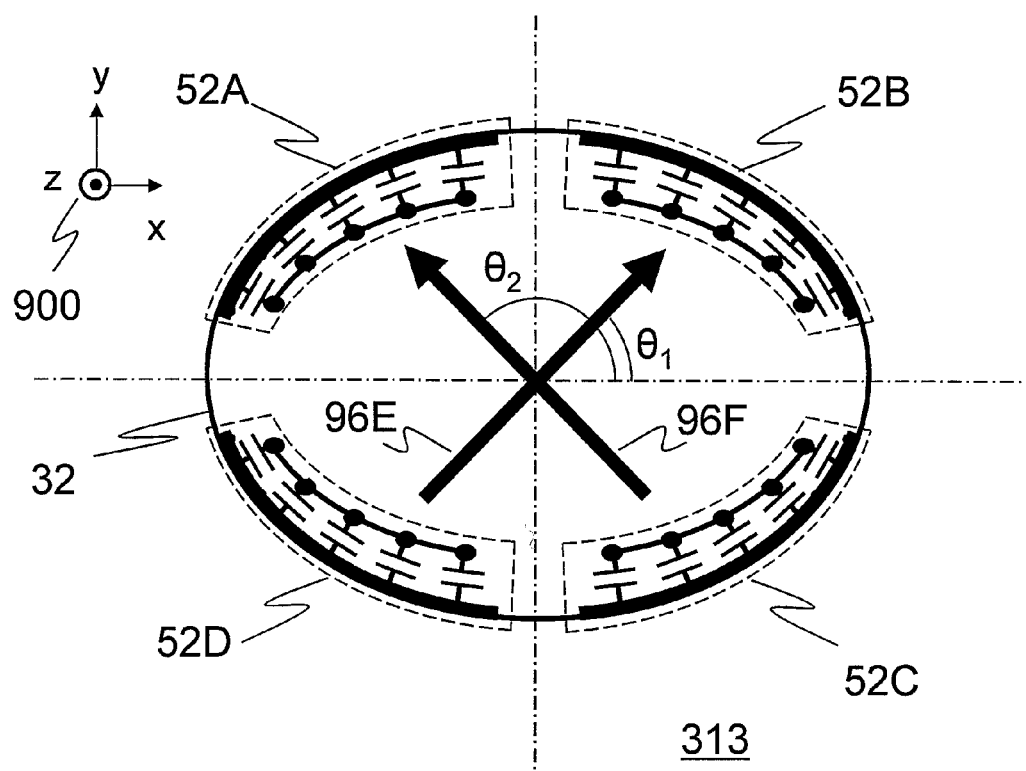
FIG. 16 illustrates the magnetic fields generated by the RF coil device according to the second embodiment.

On the other hand, the high frequency magnetic field 96F generated by the second RF coil 22 made up of the partial elliptic cylindrical coil 52B and the partial elliptic cylindrical coil 52D forms an angle of $\theta_2=180°-\theta_1$ with respect to the x-axis of the coordinate system 900 as shown in FIG. 16, since the second RF coil 22 is positioned at mirror symmetrical position with respect to the first RF coil 12, assuming the yz plane including the central axis 910 as a mirror plane.

The angle $\theta_d$ formed by the high frequency magnetic field 96E and the high frequency magnetic field 96F becomes $\theta_d=|\theta_2-\theta_1|$. The angle $\theta_d$ is determined according to the arrangement of multiple first conductor 61 of the partial elliptic cylindrical coil 52, the length $G_3$ of the first gap 83 in the circumferential direction, and the length $G_4$ of the second gap 84 in the circumferential direction, and the angle $\theta_d$ indicates a value ranging from 0 degree to 180 degrees.

On this occasion, since the phase difference between the high frequency signals applied respectively to the first 0°-180° divider/combiner 372 and to the second 0°-180° divider/combiner 373 is 90 degrees, the phase difference between the high frequency magnetic field 96E and the high frequency magnetic field 96F becomes 90 degrees. Then, the combined magnetic field of the high frequency magnetic field 96E and the high frequency magnetic field 96F forms an elliptically polarized wave field rotating within the xy plane when viewed from the z-direction of the coordinate system 900. When $\theta_d$ is 90 degrees, it becomes a circularly polarized wave field. Therefore, the RF coil device 313 irradiates the inner part of the RF shield 32 with the elliptically polarized wave field (including the circularly polarized wave field).

Figure 17:
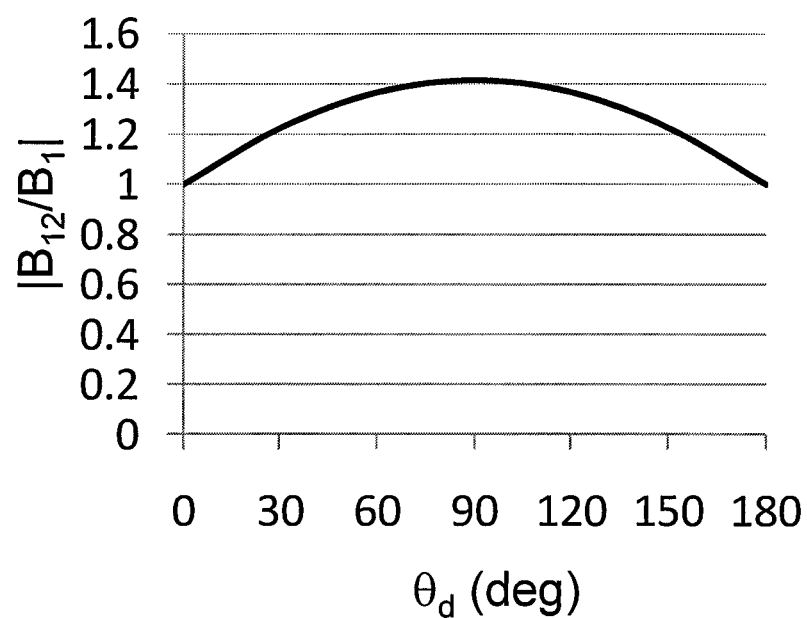
FIG. 17 is a graph showing a relation between the strength ratio and the angle $\theta_d$ of the high frequency magnetic field generated by the RF coil device according to the second embodiment.

FIG. 17 shows a relation between a ratio of $B_{12}$ to $B_1$ ($B_{12}/B_1$) and the angle $\theta_d$; the ratio between the circular polarized magnetic field strength ($B_{12}$) per 1 watt of a combined magnetic field obtained by combining the high frequency magnetic field 96E and the high frequency magnetic field 96F, and the circular polarized magnetic field strength ($B_1$) per 1 watt of the high frequency magnetic field 96E irradiated from the first RF coil 12. As illustrated, the circular polarized magnetic field strength ($B_{12}$) per 1 watt of the combined magnetic field indicates 1 or higher for all over the range of the angle $\theta_d$, being the maximum $\sqrt{2}$ when the angle $\theta_d$=90 degrees.

In response to the high frequency magnetic field being irradiated, nuclear magnetic resonance signals are emitted from the test subject 10, forming a magnetic field rotating in the xy plane viewed from the z-direction of the coordinate system 900. According to the reciprocity theorem, the RF coil device 313 detects the magnetic field rotating within the xy plane, in the same manner as the case where the high frequency magnetic field is irradiated.

As explained so far, the RF coil unit provided with the RF coil device 313 and the high frequency signal divider/combiner 370, operates as a transceive coil which irradiates the test subject 10 with the high frequency magnetic field and simultaneously detects the nuclear magnetic resonance signal generated from the test subject 10, and outputs the detected signal as a detection signal.

Next, with reference to FIG. 18A, FIG. 18B and FIG. 18C, an explanation will be made as to a method for deciding the length $G_3$ of the first gap 83 in the circumferential direction and the length $G_4$ of the second gap 84 in the circumferential direction according to the present embodiment. Those lengths are determined so that any magnetic coupling may not occur between the first RF coil 12 and the second RF coil 22.

Figure 18A:
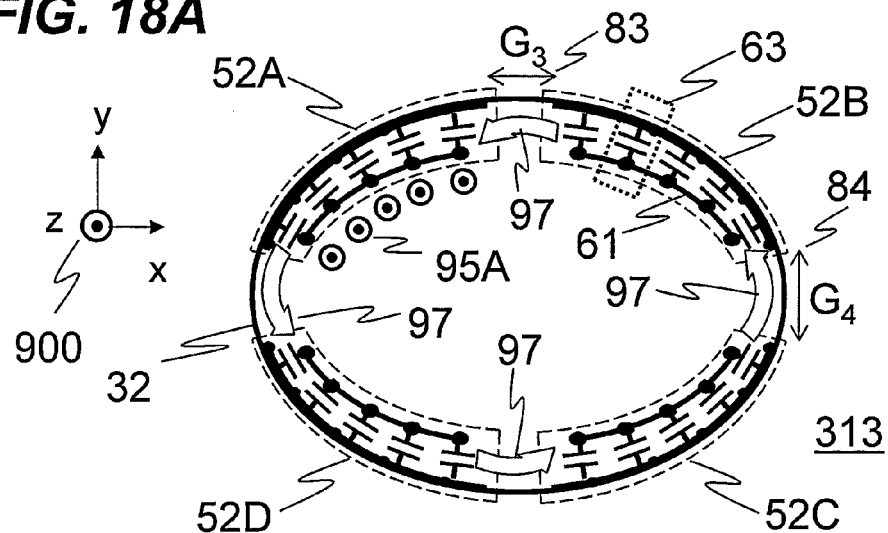
FIG. 18A illustrates a method for deciding the length of a gap in a circumferential direction in the RF coil device according to the second embodiment, and shows the state of magnetic coupling in the partial cylindrical coils.
Figure 18B:
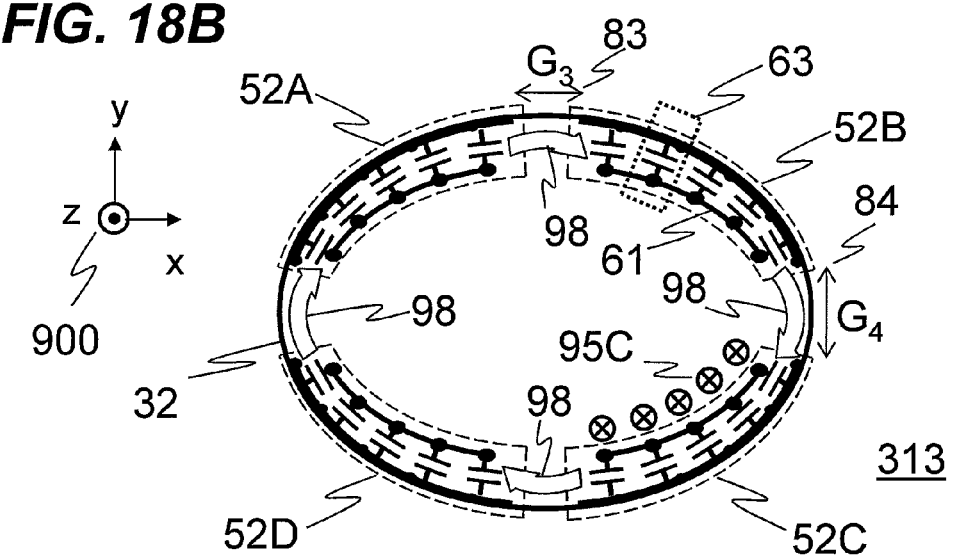
FIG. 18B illustrates a method for deciding the length of a gap in a circumferential direction in the RF coil device according to the second embodiment, and shows the state of magnetic coupling in the partial cylindrical coils.

When the RF current 95A, having the same phase, and the amplitude becoming larger along with positioned toward outside in the x-axis direction away from the central axis 910, flows in the multiple first conductors 61 of the partial elliptic cylindrical coil 52A, in the direction to the front vertically with respect to FIG. 18A on paper, the first flux 97 generated by the RF current 95A is interlinked with the loop conductor 63 of the partial elliptic cylindrical coil 52B, toward the partial elliptic cylindrical coil 52A from the partial elliptic cylindrical coil 52C along the inner wall of the RF shield 32. Therefore, the first inductive current ($I_A$) flows on the first conductor 61 of the partial elliptic cylindrical coil 52B, vertically toward the backside with respect to FIG. 18A on paper.

On the other hand, as for the RF current 95C flowing in partial elliptic cylindrical coil 52C, the phase difference between the high frequency signals applied respectively to the partial elliptic cylindrical coil 52A and to the partial elliptic cylindrical coil 52C is 180 degrees. Therefore, as shown in FIG. 18B, the second flux 98 generated by the RF current 95C is interlinked with the loop conductor 63 of the partial elliptic cylindrical coil 52B, toward the partial elliptic cylindrical coil 52C from the partial elliptic cylindrical coil 52A along the inner wall of the RF shield 32. As a result, the second inductive current ($I_C$) flows vertically toward the front with respect to FIG. 18A on paper, on the first conductor 61 of the partial elliptic cylindrical coil 52B. On this occasion, the magnitude of the first inductive current and that of the second inductive current depend on the length $G_3$ of the first gap 83 in the circumferential direction and the length $G_4$ of the second gap 84 in the circumferential direction.

Hereinafter, it is considered that the partial elliptic cylindrical coils 52A to 52D are moved along the inner wall of the RF shield 32.

Firstly, the partial elliptic cylindrical coil 52B is moved toward the partial elliptic cylindrical coil 52A, while fixing the partial elliptic cylindrical coils 52A and 52C. On this occasion, as the partial elliptic cylindrical coil 52B comes closer to the partial elliptic cylindrical coil 52A, the value of the first inductive current ($I_A$) increases, whereas the partial elliptic cylindrical coil 52B separates from the partial elliptic cylindrical coil 52C, and thus the second inductive current ($I_C$) decreases. Along with moving the partial elliptic cylindrical coil 52B, the partial elliptic cylindrical coil 52D is also moved to a position where the partial elliptic cylindrical coils 52B and 52D are rotationally symmetric at an angle of 180 degrees with respect to the central axis 910.

On the contrary, the partial elliptic cylindrical coil 52B is moved toward the partial elliptic cylindrical coil 52C. As the partial elliptic cylindrical coil 52B comes closer to the partial elliptic cylindrical coil 52C, the value of the second inductive current ($I_C$) increases, whereas the partial elliptic cylindrical coil 52B separates from the partial elliptic cylindrical coil 52A and thus the first inductive current ($I_A$) decreases.

Figure 18C:
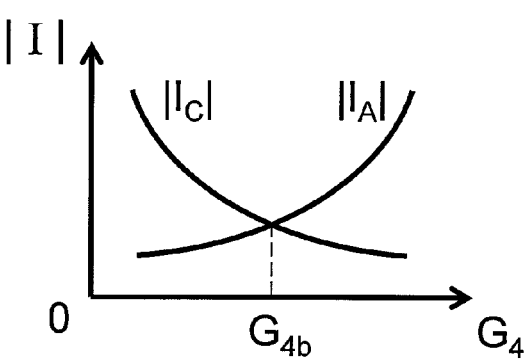
FIG. 18C illustrates a method for deciding the length of a gap in a circumferential direction in the RF coil device according to the second embodiment, and is a graph showing a relation between the inductive current flowing in the partial cylindrical coil and the length of the second gap in the circumferential direction.

Therefore, the relation between the absolute value of the first inductive current ($I_A$) and the second inductive current ($I_C$), and the length $G_4$ of the second gap 84 in the circumferential direction is illustrated as shown in FIG. 18C. In FIG. 18C, the vertical axis represents the absolute value of the inductive current (|I|), and the horizontal axis represents the length $G_4$ of the second gap 84 in the circumferential direction. As illustrated, at the length $G_{4b}$ of the second gap 84 in the circumferential direction, the absolute value of the first inductive current ($I_A$) becomes equal to the absolute value of the second inductive current ($I_C$). On this occasion, since the direction of the first inductive current ($I_A$) is opposite to the direction of the second inductive current ($I_C$), inductive current caused by the partial elliptic cylindrical coil 52A and the partial elliptic cylindrical coil 52C does not flow in the partial elliptic cylindrical coil 52B. In other words, when the length of the second gap 84 in the circumferential direction is assumed as $G_{4b}$, it is possible to achieve the state where any magnetic coupling does not occur. Accordingly, the length $G_4$ of the second gap 84 in the circumferential direction is determined as $G_{4b}$. Along with this decision, the length $G_3$ of the first gap 83 in the circumferential direction is also determined.

In the present embodiment, as described above, the position where the absolute value of the first inductive current ($I_A$) becomes equal to the absolute value of the second inductive current ($I_C$) is searched out, and thereby deciding the length $G_{4b}$ of the second gap 84 in the circumferential direction and the length $G_3$ of the first gap 83 in the circumferential direction. Therefore, when the length $G_4$ of the second gap 84 in the circumferential direction is decided as $G_{4b}$, it is necessary to check that any inductive current does not flow in the partial elliptic cylindrical coil 52B. This can be checked by using a network analyzer, for instance. In other words, the first port of the network analyzer is connected to the partial elliptic cylindrical coil 52A and the partial elliptic cylindrical coil 52C via the first 0°-180° divider/combiner 372, the second port of the network analyzer is connected to the partial elliptic cylindrical coil 52B, and it is judged based on passage characteristics of the first port and the second port ($S_{12}$). It is further possible to perform checking by the use of electromagnetic field simulation.

An explanation has been made so far, as to a method for deciding the length $G_3$ of the first gap 83 in the circumferential direction and the length $G_4$ of the second gap 84 in the circumferential direction, so that any magnetic coupling does not occur between the first RF coil 12 and the second RF coil 22.

Next, there will be shown a result of comparison with a birdcage coil conventionally used, with regard to a degree of enlarging the examination space, irradiation strength, and homogeneity in the irradiation distribution of the RF coil device 313 according to the present embodiment. The irradiation distributions of both coils are obtained by the electromagnetic field simulation.

The specifications of the RF coil device 313 used for the comparison were as the following. The elliptic cylindrical RF shield 32 was 700 min diameter in the long axis direction, 635 mm in diameter in the short axis direction, and 1,000 mm in length, the dimension of the first conductor 61 of the partial elliptic cylindrical coil 52 was 40 mm in width, 540 mm in length, and the number of the first conductor 61 was five, the dimension of the second conductor 62 of the partial elliptic cylindrical coil was 45 mm in width, 36 mm in length, and the number of the second conductor 62 were eight. The first conductor 61 and the second conductor 62 were placed along the elliptic cylindrical surface being 680 mm in diameter in the long axis direction and 575 mm in diameter in the short axis direction, sharing the central axis 910 of the RF shield 32. The length $G_3$ of the first gap 83 in the circumferential direction and the length $G_4$ of the second gap 84 in the circumferential direction were set to be 184 mm and 152 mm, respectively. A value of the first capacitor 71 was adjusted in such manner that the resonance frequency of the RF coil device 313 became 64 MHz.

An elliptic cylindrical RF shield having the same size as the RF shield 32 was employed as the birdcage coil used for the comparison, and it was a 16-rung high-pass elliptical birdcage coil being 540 mm in length in which coil elements being 40 mm in width were arranged along the elliptic cylindrical surface having the same size as the elliptic cylindrical surface where the first conductor 61 and the second conductor 62 were placed. Also for this birdcage coil, a value of the capacitor was adjusted in such manner that the resonance frequency became 64 MHz.

In the RF coil device 313, the QD irradiation according to the method of the present embodiment was performed, and in the elliptical birdcage coil, the irradiation was performed according to an ordinary QD method. As in the case of the comparative example of the first embodiment, a cylindrical phantom simulating a human abdominal region, 300 mm in diameter and 500 mm in length, was placed at the position sharing the center of the RF shield 32 as the center of the cylindrical phantom and sharing the central axis 910 as the central axis of the cylindrical phantom, and then, the irradiation strength was calculated. On this occasion, the electric conductivity of the phantom was set to 0.6 [S/m] and the relative permittivity was set to be 45. The homogeneity of the irradiation distribution was evaluated under the condition that the cylindrical phantom was not inserted (no load).

In the RF coil device 313, on a plane vertical to the central axis 910 passing through the center (origin point) of the RF shield 32, an average irradiation strength per 1 watt in the region being 150 mm in radius about the origin point was 0.272 [A/m/√W], and a degree of homogeneity of the irradiation distribution in the same region was 5.3%. On the other hand, in the elliptical birdcage coil, the average irradiation strength per 1 watt in the same region was 0.309 [A/m/√W], and the degree of homogeneity of the irradiation distribution was 5.0%. The degree of homogeneity of the irradiation distribution was expressed as a percentage, being a ratio of a difference between a maximum value and a minimum value to a sum of the maximum value and the minimum value of the irradiation strength within the set region.

The irradiation strength of the RF coil device 313 according to the present embodiment was 88% of the strength of the elliptical birdcage coil that performed the QD irradiation. The difference of 12% falls into an allowance range of the power capacity held by the amplifier of the transmitter 330, and thus it was shown that the RF coil device 313 of the present embodiment had the irradiation strength approximately equivalent to that of the conventional elliptical birdcage coil. As for the degree of homogeneity, the difference between the RF coil device 313 and the birdcage coil was just around 1% being extremely small, and it was shown that the RF coil device 313 of the present embodiment had almost equivalent homogeneity of irradiation distribution as that of the elliptical birdcage coil.

On the other hand, as for the examination space, if the RF coil device 313 is employed, the space is expanded in the x-axis direction and in the y-axis direction of the coordinate system 900, compared to the case of the elliptical birdcage coil. Specifically, when the center of the RF shield 32 is assumed as the origin point of the coordinate system 900, the space 88 in the x-axis direction (see FIG. 14A) expands by 20 mm within the region of ±76 mm in the y-direction, and the space 88 in the y-axis direction (see FIG. 14A) expands by 66 mm within the region of ±92 mm in the x-direction. Therefore, by using the RF coil device 313 of the present embodiment as the transceive coil 310, instead of the elliptical birdcage coil, it is possible to expand the examination space, while keeping a similar degree of irradiation strength and homogeneity of the irradiation distribution.

As explained above, according to the present embodiment, it is possible to provide the transceive coil 310 whose examination space is expanded for accommodating the test subject 10, without significantly deteriorating the irradiation efficiency and homogeneity of irradiation distribution in a desired imaging region. On this occasion, it is not necessary to enlarge the inner diameter of the magnet or the gradient magnetic field coil.

Further according to the present embodiment, since the RF shield and the RF coil are elliptic cylindrical shape, it is possible to expand the examination space further in one direction. Therefore, according to the present embodiment, it is possible to configure an MRI apparatus which provides a sense of openness to the test subject, or an MRI apparatus which reserves space for installing various equipment within the examination space.

In the present embodiment, an explanation has been made taking an example that elements are arranged in such a manner that a distance between the first conductor 61 and the second conductor 62, and the partial elliptic cylindrical conductor 42, becomes narrower, along with being positioned toward outside in the x-axis direction away from the central axis 910. However, the arrangement is not limited to this example. As in the case of the first embodiment, it is possible to set the distance to be constant between the first conductor 61 and the second conductor 62, and the partial elliptic cylindrical conductor 42. In other words, the conductors may be arranged in such a manner that the distance from the inner wall of the RF shield 32 to each of the conductors respectively constituting the first conductor 61 and the second conductor 62 becomes equal. Further, the conductors respectively constituting the first conductor 61 and the second conductor 62 may be arranged in such a manner that the distance from the RF shield 32 (partial elliptic cylindrical conductor 42) becomes larger, along with being positioned toward outside in the long axis direction away from the central axis of the RF shield 32. In other words, the distance between the first conductor 61 and the second conductor 62, and the partial elliptic cylindrical conductor 42 may become wider along with being positioned toward outside in the x-axis direction away from the central axis 910. The distance from the partial elliptic cylindrical conductor 42 may be different between any two of the first conductors 61. Further in the present embodiment, the first conductors 61 are arranged with equal spacing in the circumferential direction, but it is not necessary to place them with equal spacing. Any arrangement is possible as far as the irradiation distribution is homogeneous.

As in the case of the first embodiment, the RF shield 32 and the partial elliptic cylindrical conductor 42 of the partial elliptic cylindrical coil 52 may have a circular cylindrical shape. Even in this case, they are arranged in such a manner that the distance between the first conductor 61 and the second conductor 62, and the partial elliptic cylindrical conductor 42 of the partial elliptic cylindrical coil 52 becomes narrower along with being positioned toward outside away from the central axis 910 in the x-axis direction.

As in the case of the first embodiment, the RF shield 32 and the partial elliptic cylindrical conductor 42 may be configured as a single unit. It is also possible to configure in such a manner that space is provided between the RF shield 32 and partial elliptic cylindrical conductor 42.

Also in the present embodiment, as in the case of the first embodiment, it is only required that at least on one side of the ends of the first conductors 61 adjacent to each other are short-circuited by the second conductor 62.

It is only required that the RF shield 32 and the partial elliptic cylindrical conductor 42 have the thickness and structure which allow the gradient magnetic field to pass through and serve as a shielding against the high frequency magnetic field.

The configuration (inner wiring) of the high frequency signal divider/combiner 370 is not limited to those as shown in the aforementioned FIG. 5. It is only required that a relation between the amplitude and the phase of the input signal and the output signal of the high frequency signal divider/combiner 370 satisfies the relation described above. It is further possible to provide predetermined ranges to the phase difference in high frequency signals respectively applied to the feeding ports, and to the phase difference in high frequency signals respectively supplied to the first 0°-180° divider/combiner 372 and the second 0°-180° divider/combiner 373, as in the case of the first embodiment.

<<Third Embodiment>>

Next, the third embodiment to which the present invention is applied will be explained. The MRI apparatus of the present embodiment is basically the same as the second embodiment. However, an RF coil device 314 used as the transceive coil 310 of the MRI apparatus according to the present embodiment is provided with a magnetic coupling adjuster for adjusting magnetic coupling between the first RF coil 12 and the second RF coil 22, in addition to the RF coil device 313 of the second embodiment. Hereinafter, the present embodiment will be explained, focusing on the configuration different from the second embodiment. Also in the present embodiment, the orientation of the static magnetic field 920 generated by the magnet 110 of horizontal magnetic field system is assumed as the z-axis direction of the coordinate system 900.

Figure 19A:
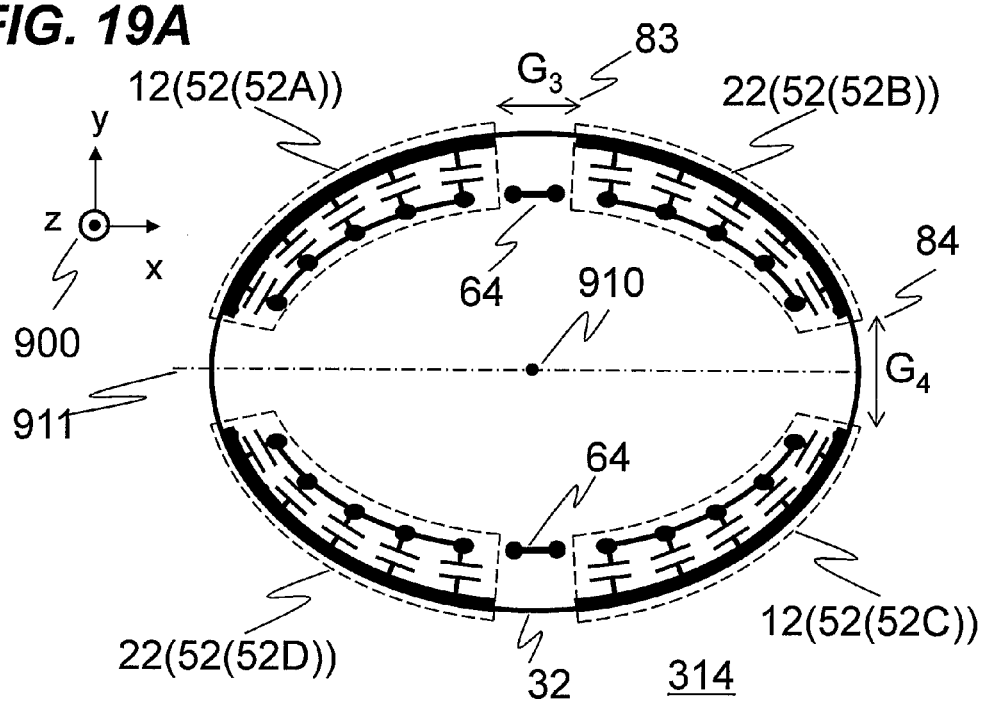
FIG. 19A illustrates the RF coil device according to a third embodiment, and shows the RF coil device viewed in the central axis direction.
Figure 19B:
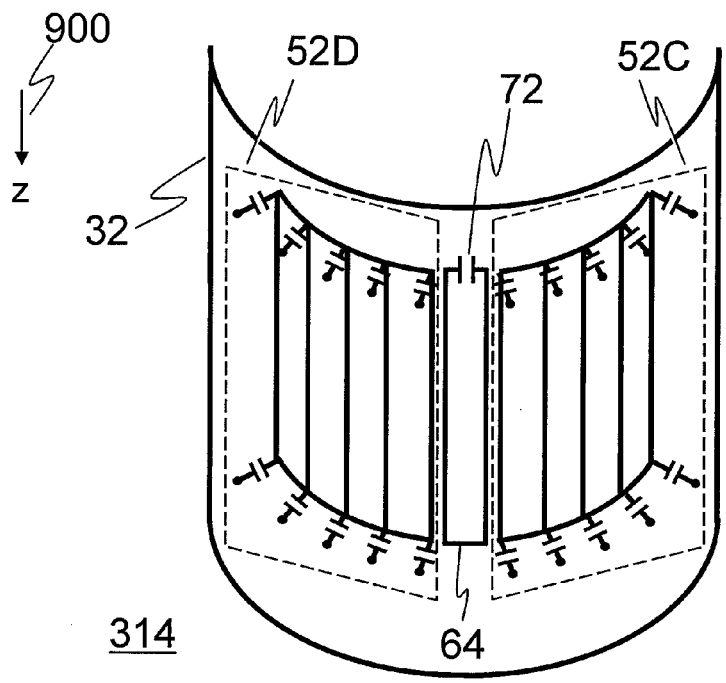
FIG. 19B illustrates the RF coil device according to a third embodiment, and shows the partial elliptic cylindrical coil viewed from a plane being parallel to the xz plane and passing through the central axis.

FIG. 19A and FIG. 19B illustrates a configuration of the RF coil device 314 of the present embodiment. This RF coil device 314 is used as the transceive coil 310 as shown in FIG. 2. FIG. 19A illustrates the RF coil device 314 viewed in the direction of the central axis 910, and FIG. 19B illustrates the partial elliptic cylindrical coils 52C and 52D, viewed from the plane 911 passing through the central axis 910 and being parallel to the xz plane of the coordinate system 900.

As described above, the RF coil device 314 of the present embodiment has a configuration basically the same as the RF coil device 313 of the second embodiment. The RF coil device 314 of the present embodiment is further provided with a magnetic coupling adjuster. The magnetic coupling adjuster is a configuration to prevent the occurrence of magnetic coupling between the first RF coil 12 and the second RF coil 22, and in the present embodiment, there is provided a conductor loop 64 which has a second capacitor 72 being inserted as the magnetic coupling adjuster.

The conductor loop 64 is placed in a pair of gaps positioned axial-symmetrically with respect to the central axis 910, among multiple gaps between the first RF coil 12 and the second RF coil 22. In other words, each conductor loop 64 is placed between the partial elliptic cylindrical coil 52A and the partial elliptic cylindrical coil 52B, and between the partial elliptic cylindrical coil 52C and the partial elliptic cylindrical coil 52D. The conductor loop 64 is placed in such a manner that the loop conductor surface becomes vertical with respect to the yz plane which includes the central axis 910. A value of the second capacitor 72 is adjusted in such a manner that any magnetic coupling does not occur between the first RF coil 12 and the second RF coil 22.

The arrangement of each of feeding ports and connection with the transmitter 330 and the receiver 340 via the high frequency signal divider/combiner 370 and the transmit/receive switching unit 320, of the RE coil device 314 of the present embodiment, are similar to the connection aspects of the first embodiment as shown in FIG. 5. In other words, though not illustrated in FIG. 19A and FIG. 19B, the partial elliptic cylindrical coil 52A is provided with the first feeding port, the partial elliptic cylindrical coil 52B is provided with the second feeding port, the partial elliptic cylindrical coil 52C is provided with the third feeding port, and the partial elliptic cylindrical coil 52D is provided with the fourth feeding port, and each of those elements receives a supply of high frequency signals and detects a high frequency magnetic field being generated. Each feeding port is placed at the position where the first capacitor 71 becomes caught in the feeding port, in the same manner as the first embodiment.

In the second embodiment, the length $G_3$ of the first gap 83 in the circumferential direction and the length $G_4$ of the second gap 84 in the circumferential direction are fixed to a particular length so that any magnetic coupling may not occur between the first RF coil 12 and the second RF coil 22. On the other hand, in the present embodiment, the magnetic coupling adjuster is able to set those lengths of the gaps in the circumferential direction arbitrarily. Hereinafter, it will be explained that the length $G_3$ of the first gap 83 in the circumferential direction and the length $G_4$ of the second gap 84 in the circumferential direction are adjustable by the magnetic coupling adjuster (the conductor loop 64) of the present embodiment.

The conductor loop 64 in which the second capacitor 72 is inserted is a resonance circuit having a resonance frequency $f_d$. When the value of the second capacitor 72 is adjusted in such a manner that the resonance frequency $f_d$ becomes lower than the operating frequency of the RF coil device 314, the conductor loop 64 operates as an inductive reactance in the operating frequency of the RF coil device 314.

On this occasion, when the RF current 95A flows in the multiple first conductors 61 of the partial elliptic cylindrical coil 52A, the RF current having the same phase and the amplitude becoming larger along with being positioned toward outside in the x-axis direction away from the central axis 910, being directed to the front vertically with respect to the figure on paper, as shown in FIG. 18A, the first flux 97 caused by the RF current 95A is interlinked with the loop conductor surface of the conductor loop 64, in the direction penetrating to the RF shield 32. As a result, inductive current flows in the conductor loop 64 so as to cancel the first flux 97. The flux generated by the inductive current is interlinked with the loop conductor 63 of the partial elliptic cylindrical coil 52B, along the inner wall of the RF shield 32 from the partial elliptic cylindrical coil 52C to the partial elliptic cylindrical coil 52A. Therefore, the conductor loop 64 substantially increases the first flux 97 interlinking with the loop conductor 63, and the first inductive current $(I_A)$ flowing on the partial elliptic cylindrical coil 52B increases.

Figure 20A:
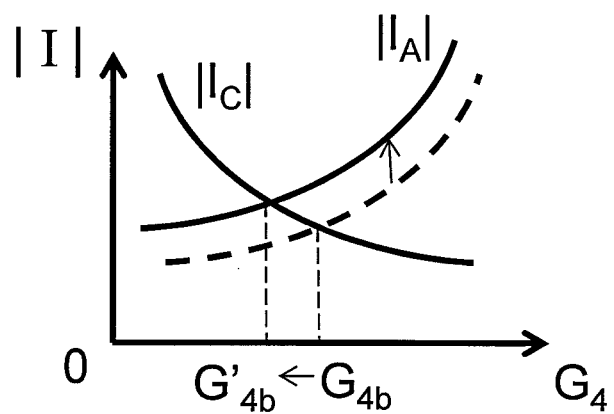
FIG. 20A is a graph showing a relation between the inductive current flowing in the partial cylindrical coil and the length of the second gap in the circumferential direction of the RF coil device according to the third embodiment.

FIG. 20A illustrates by a solid line, a relation between the absolute value of the first inductive current $(I_A)$ and the absolute value of the second inductive current $(I_C)$, and the length $G_4$ of the second gap 84 in the circumferential direction. In FIG. 20A, the vertical axis represents the absolute value of the inductive current (|I|), and the horizontal axis represents the length $G_4$ of the second gap 84 in the circumferential direction. Here, a relation between the absolute value of the first inductive current $(I_A)$ and the length $G_4$ of the second gap 84 in the circumferential direction is shown by the broken line, in the case where the conductor loop 64 is not provided. As illustrated, when the conductor loop 64 is added, the absolute value of the first inductive current $(I_A)$ increases with respect to the same length $G_4$ of the second gap 84 in the circumferential direction. Therefore, the length $G_4$ of the second gap 84 in the circumferential direction at which the absolute value of the first inductive current $(I_A)$ becomes equal to the absolute value of the second inductive current $(I_C)$, in other words, the length $G_4$ of the second gap 84 in the circumferential direction at which the first inductive current $(I_A)$ and the second inductive current $(I_C)$ cancel each other, becomes $G'_{4b}$ which is shorter than $G_{4b}$ being the length for the case where the conductor loop 64 is not provided.

The increased amount of the absolute value of the first inductive current $(I_A)$ may be changed by the value of the second capacitor 72. Therefore, by changing the value of the second capacitor 72, it is possible to make adjustments so as to further reduce the length $G_4$ of the second gap 84 in the circumferential direction. The length $G_3$ of the first gap 83 in the circumferential direction can be decided in the same manner.

On the other hand, when the value of the second capacitor 72 is adjusted in such a manner that the resonance frequency $f_d$ becomes higher than the operating frequency of the RF coil device 314, the conductor loop 64 operates as capacitative reactance in the operating frequency of the RF coil device 314.

On this occasion, the first flux 97 generated by the RF current 95A is interlinked with the loop conductor surface of the conductor loop 64 in the direction penetrating to the RF shield 32, and inductive current flows in the conductor loop 64 so as to generate a flux in the same direction as the first flux 97 interlinked with the conductor loop 64. The flux generated by the inductive current is interlinked with the loop conductor 63 of the partial elliptic cylindrical coil 52B, along the inner wall of the RF shield 32, from the partial elliptic cylindrical coil 52A towards the partial elliptic cylindrical coil 520. Therefore, due to the conductor loop 64, the first flux 97 interlinked with the loop conductor 63 decreases, and the first inductive current $(I_A)$ flowing on the partial elliptic cylindrical coil 52B substantially decreases.

Figure 20B:
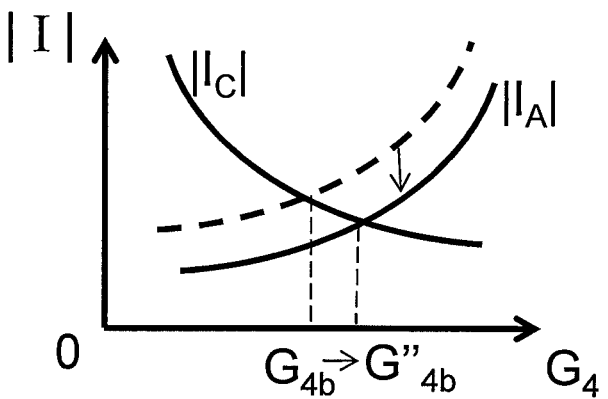
FIG. 20B is a graph showing a relation between the inductive current flowing in the partial cylindrical coil and the length of the second gap in the circumferential direction of the RF coil device according to the third embodiment.

FIG. 20B illustrates by a solid line, a relation between the absolute value of the first inductive current $(I_A)$ and the absolute value of the second inductive current $(I_C)$, and the length $G_4$ of the second gap 84 in the circumferential direction. In FIG. 20B, the vertical axis represents the absolute value of the inductive current (|I|) and the horizontal axis represents the length $G_4$ of the second gap 84 in the circumferential direction. Here, a relation between the absolute value of the first inductive current $(I_A)$ and the length $G_4$ of the second gap 84 in the circumferential direction is shown by the broken line, in the case where the conductor loop 64 is not provided. As illustrated, when the conductor loop 64 is added, the absolute value of the first inductive current $(I_A)$ decreases with respect to the same length $G_4$ of the second gap 84 in the circumferential direction. Therefore, the length $G_4$ of the second gap 84 in the circumferential direction at which the absolute value of the first inductive current $(I_A)$ becomes equal to the absolute value of the second inductive current $(I_C)$, in other words, the length $G_4$ of the second gap 84 in the circumferential direction at which the first inductive current $(I_A)$ and the second inductive current $(I_C)$ cancel each other, becomes $G''_{4b}$ which is longer than $G_{4b}$ being the length for the case where the conductor loop 64 is not provided.

The decreased amount of the absolute value of the first inductive current $(I_A)$ may be changed by the value of the second capacitor 72. Therefore, by changing the value of the second capacitor 72, it is possible to make adjustments so as to further increase the length $G_4$ of the second gap 84 in the circumferential direction. The length $G_3$ of the first gap 83 in the circumferential direction can be decided in the same manner.

As explained so far, by setting the conductor loop 64 and adjusting the value of the second capacitor 72, it is possible to arbitrarily decide the length $G_3$ of the first gap 83 in the circumferential direction and the length $G_4$ of the second gap 84 in the circumferential direction, without generating the magnetic coupling between the first RF coil 12 and the second RF coil 22.

The RF coil device 314 of the present embodiment has the same configuration as the RF device 313 of the second embodiment and operates similarly, except the configuration that the length $G_3$ of the first gap 83 in the circumferential direction and the length $G_4$ of the second gap 84 in the circumferential direction are flexibly settable. Therefore, as in the case of the second embodiment, the RF coil device operates as the transceive coil 310.

As explained above, according to the present embodiment, it is possible to obtain the same effect as the second embodiment. Further, according to the present embodiment, by adjusting the value of the second capacitor 72 inserted into the conductor loop 64, it is possible to arbitrarily set the length $G_3$ of the first gap 83 in the circumferential direction and the length $G_4$ of the second gap 84 in the circumferential direction, without generating the magnetic coupling, and therefore, design flexibility is increased.

In the present embodiment, the conductor loop 64 is arranged in such a manner that the loop conductor surface is vertical with respect to yz plane including the central axis 910, but the arrangement of the conductor loop 64 is not limited to this example. It is only required to have an arrangement which allows occurrence of the magnetic coupling between the first RF coil 12 and the second RF coil 22, only to the degree that the first inductive current ($I_A$) and the second inductive current ($I_C$) cancel each other by adjusting the value of the second capacitor 72. In the present embodiment, the conductor loop 64 in which the second capacitor 72 is inserted is used as the magnetic coupling adjuster, but this is not the only example. Any configuration or shape is applicable as far as the amount of magnetic coupling between the partial elliptic cylindrical coils 52 is adjustable.

Figure 21A:
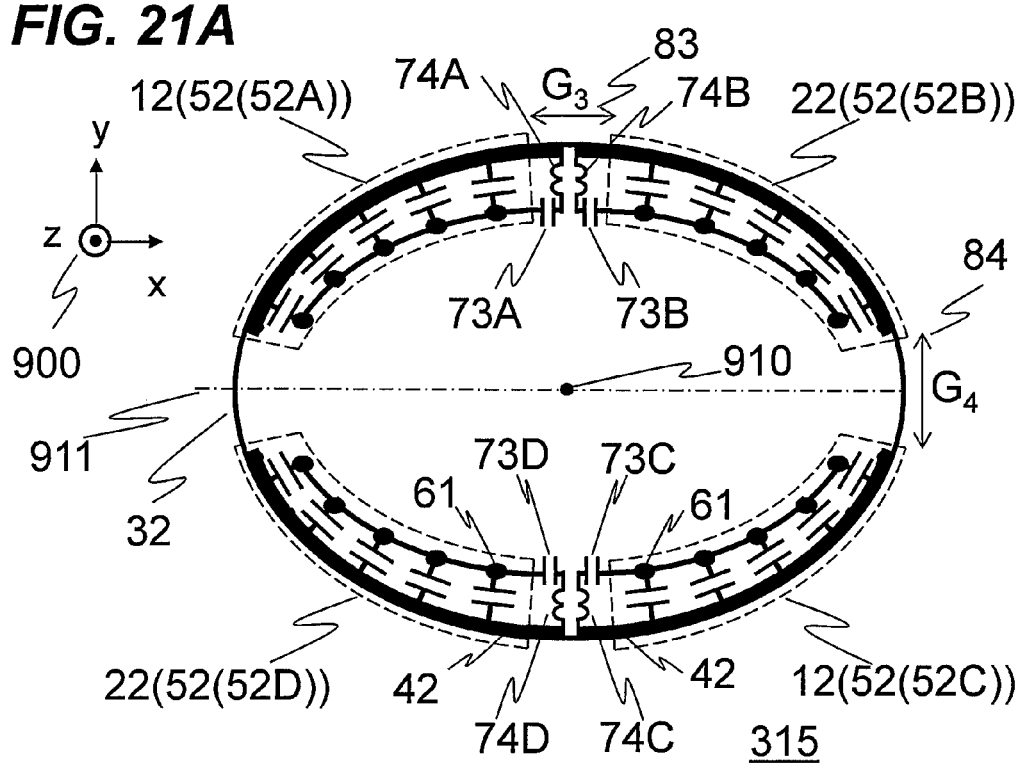
FIG. 21A illustrates a modification example of the RF coil device according to the third embodiment, and shows the RF coil device viewed in the central axis direction.
Figure 21B:
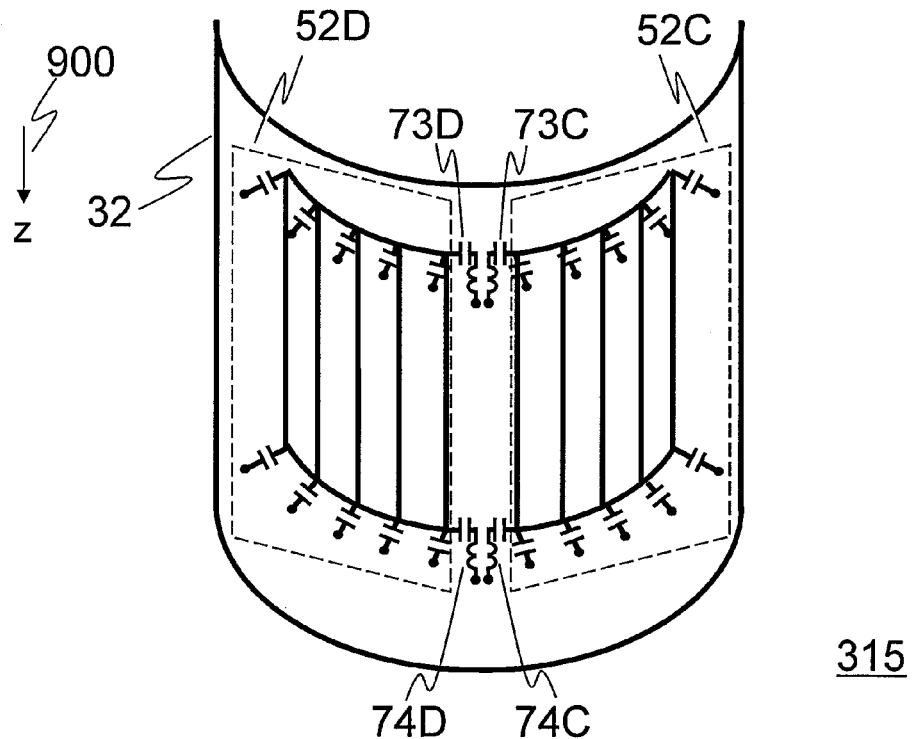
FIG. 21B illustrates a modification example of the RF coil device according to the third embodiment, and shows the partial elliptic cylindrical coil viewed from the plane being parallel to the xz plane and passing through the central axis.

FIG. 21A and FIG. 21B shows an RF coil device 315 which is provided with another magnetic coupling adjuster. FIG. 21A illustrates the RF coil device 315 viewed in the direction of the central axis 910, and FIG. 21B illustrates the RF coil device 315, viewing the partial elliptic cylindrical coils 52C and 52D, from the plane 911 passing through the central axis 910 and being parallel to the xz plane of the coordinate system 900.

The RF coil device 315 is provided with a magnetic coupling adjusting circuit as the magnetic coupling adjuster, which is made up of a third capacitor 73 and an adjusting inductor 74 being serially connected. The magnetic coupling adjusting circuit is placed within a pair of gaps positioned axial-symmetrically with respect to the central axis 910, among multiple gaps between the first RF coil 12 and the second RF coil 22. In other words, multiple magnetic coupling adjusting circuits are placed, between the partial elliptic cylindrical coils 52A and 52B and between the partial elliptic cylindrical coils 52C and 52D.

It is assumed here that there are placed between the partial elliptic cylindrical coils 52C and 52D, the magnetic coupling adjusting circuit provided with the third capacitor 73C and the adjusting inductor 74C, and the magnetic coupling adjusting circuit provided with the third capacitor 73D and the adjusting inductor 74D. On this occasion, the other end of the third capacitor 73C is connected to the first conductor 61 of the partial elliptic cylindrical coil 52C, and the other end of the adjusting inductor 740 is connected to the partial elliptic cylindrical conductor 42 of the partial elliptic cylindrical coil 52C. The other end the third capacitor 73D is connected to the first conductor 61 of the partial elliptic cylindrical coil 52D, and the other end of the adjusting inductor 74D is connected to the partial elliptic cylindrical conductor 42 of the partial elliptic cylindrical coil 52D. The adjusting inductor 74C and the adjusting inductor 74D are arranged in such a manner that magnetic coupling occurs between the adjusting inductor 74C and the adjusting inductor 74D. In other words, the adjusting inductor 74C and the adjusting inductor 74D are arranged in such a manner that both come to close to each other, and the magnetic field orientations generated by both inductors do not form a right angle. Furthermore, the value of mutual inductance between the adjusting inductors 74C and 74D and the value of the third capacitor 73 are adjusted, so that any magnetic coupling may not occur between the first RF coil 21 and the second RF coil 22.

Furthermore, the magnetic coupling adjusting circuit placed between the partial elliptic cylindrical coils 52A and 52B are provided with the third capacitors 73A and 73B, and the adjusting inductors 74A and 74B, respectively. The configuration and the aspects of connection are the same as those of the magnetic coupling adjusting circuits placed between the partial elliptic cylindrical coils 52C and 52D.

In this magnetic coupling adjusting circuit, the value of the mutual inductance of the adjusting inductors 74 and the value of the third capacitors 73 are changed, thereby changing the magnitude of the magnetic coupling which occurs between the first RF coil 12 and the second RF coil 22. Therefore, as in the case of the conductor loop 64 in which the second capacitor 72 is inserted, it is possible to arbitrarily set the length $G_3$ of the first gap 83 in the circumferential direction and the length $G_4$ of the second gap 84 in the circumferential direction.

Also in the present embodiment, various modifications are possible as in the case of the second embodiment.

In the present embodiment, an explanation has been made taking an example that the RF coil device 313 having an elliptic cylindrical shape of the second embodiment is provided with the magnetic coupling adjuster. However, it is also possible that the circular cylindrical RF coil device like the RF coil devices 311 and 312 of the first embodiment is provided with the magnetic coupling adjuster of the present embodiment. In the first embodiment, the length $G_1$ of the first gap 81 in the circumferential direction and the length $G_2$ of the second gap 82 in the circumferential direction are equalized, thereby preventing the occurrence of magnetic coupling. However, in this example here, the magnetic coupling can be prevented without such restriction. In other words, by adjusting the value of the second capacitor 72 of the magnetic coupling adjuster, it is possible to arbitrarily set the length $G_1$ of the first gap 81 in the circumferential direction, and the length $G_2$ of the second gap 82 in the circumferential direction.

<<Fourth Embodiment>>

Next, the fourth embodiment to which the present invention is applied will be explained. The MRI apparatus of the present embodiment is basically the same as the first embodiment. In the MRI apparatus of the present embodiment here, the transmit RF coil and the receive RF coil are provided separately. Hereinafter, an explanation will be made focusing on the configuration different from the first embodiment. Also in the present embodiment, the orientation of the static magnetic field 920 generated by the magnet 110 of the horizontal magnetic field system is assumed as the z-axis direction of the coordinate system 900.

Figure 22:
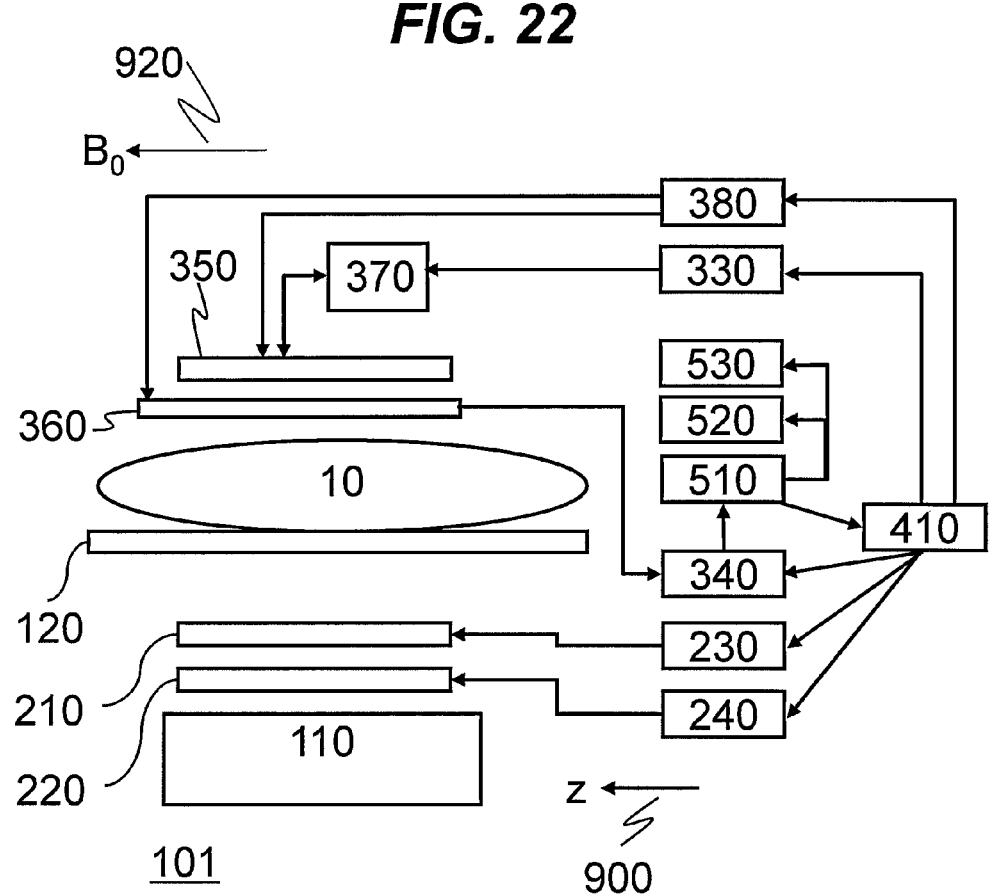
FIG. 22 is a block diagram showing a schematic configuration of the MRI apparatus according to a fourth embodiment.

FIG. 22 is a block diagram showing a schematic configuration of the MRI apparatus 101 of the present embodiment. The MRI apparatus 101 of the present embodiment has a configuration basically the same as the MRI apparatus 100 of the first embodiment. However, a transmit RF coil for performing irradiation of the high frequency magnetic field and a receive RF coil for receiving the nuclear magnetic resonance signal are provided independently. In other words, the transmit RF coil 350 and the receive RF coil 360 are provided, substituting for the transceive coil 310. In the present embodiment, the transmit RF coil 350 is connected to the transmitter 330 via the high frequency signal divider/combiner 370, and the receive RF coil 360 is connected to the receiver 340. The transmit/receive switching unit 320 is not provided.

The MRI apparatus 101 of the present embodiment is further provided with a detune circuit driver 380 for switching between operation and non-operation of the transmit RF coil 350 and the receive RF coil 360, and preventing the occurrence of magnetic coupling between both coils. The detune circuit driver 380 is connected to the transmit RF coil 350 and the receive RF coil 360, transmits detune signals to both coils, and switches between the operation and non-operation of both coils. In the present embodiment, while the detune signal is being transmitted, the transmit RF coil 350 is in the state of operation and the receive RF coil 360 is in the state of non-operation, whereas while the detune signal is not being transmitted, the transmit RF coil 350 is in the state of non-operation, and the receive RF coil 360 is in the state of operation. The detune signal is outputted based on an instruction from the sequencer 410 that is controlled by the computer 510 according to a predetermined program.

Figure 23A:
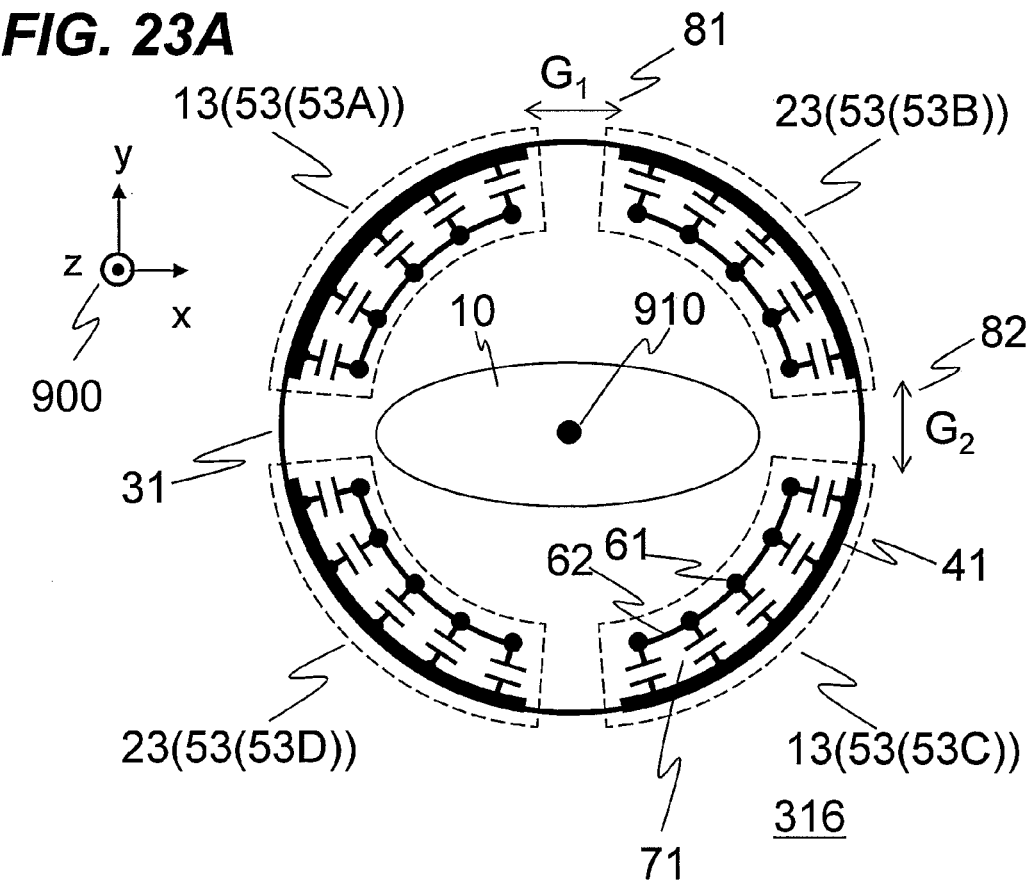
FIG. 23A illustrates the RF coil device according to the fourth embodiment, and shows the RF coil device viewed in the central axis direction.
Figure 23B:
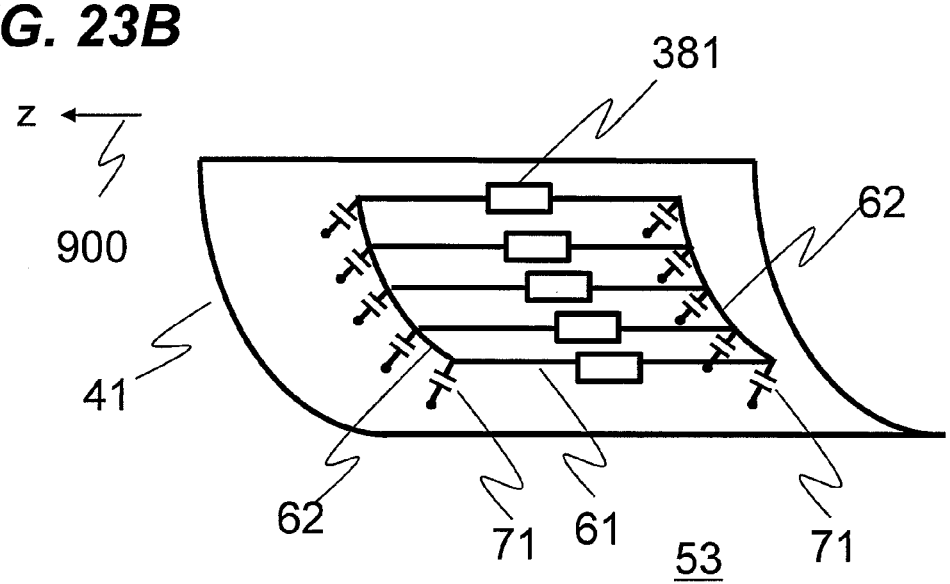
FIG. 23B illustrates the RF coil device according to the fourth embodiment, and shows the partial cylindrical coil being a constitutional element of the RF coil device, viewed at an oblique angle.

Next, an explanation will be made as to the transmit RF coil 350 according to the present embodiment. The transmit RF coil 350 of the present embodiment is provided with a configuration for switching between operation and non operation according to a detune signal. FIG. 23A and FIG. 23B illustrate an RF coil device 316 used as the transmit RF coil 350 of the present embodiment. FIG. 23A illustrates the RF coil device 316 viewed in the direction of the central axis 910 of the RF shield 31 described below, and FIG. 23B illustrates the partial cylindrical coil 53, being a constitutional element of the RF coil device 316, viewed at an oblique angle.

The RF coil device 316 has a configuration approximately the same as the configuration of the RF coil device 311 as shown in FIG. 3A and FIG. 3B. In other words, the first RF coil 13, the second RF coil 23, and the RF shield 31 are provided. As shown in FIG. 23A, the RF shield 31 is made up of a cylindrical conductor with the size accommodating the test subject 10. The arrangement of the first RF coil 13 and the second RF coil 23 is the same as the arrangement of the first RF coil 11 and the second RF coil 21 according to the first embodiment.

Further, the first RF coil 13 is provided with two partial cylindrical coils 53 (53A and 53C) arranged at positions opposed to each other placing the central axis 910 therebetween along the circumferential direction inside the RF shield 31. The second RF coil 23 is provided with two partial cylindrical coils 53 (53B and 53D), arranged at the positions opposed to each other placing the central axis 910 therebetween along the circumferential direction inside the RF shield 31.

As shown in FIG. 23B, the partial cylindrical coil 53 is provided with the partial cylindrical conductor 41, multiple first conductors 61 substantially parallel to the central axis 910, multiple first capacitors 71 connecting both ends of the first conductor 61 with the partial cylindrical conductor 41, and multiple second conductors 62 connecting both ends of the first conductor 61 with both ends of the first conductor 61 being adjacent, respectively. FIG. 23B illustrates an example that there are five first conductors 61, ten first capacitors 71, and eight second conductors 62, but the number of lines and the number of units are not limited to those numbers. In addition, each of the partial cylindrical coils 53 (53A, 53B, 53C, and 53D) is provided with detune circuits 381 on the first conductors 61, respectively.

Also in the present embodiment, the partial cylindrical conductor 41 is placed in such a manner as coming into contact with the inside surface (the inner wall 9) of the RF shield 31. The first conductors 61 are placed with equal spacing in the circumferential direction of the RF shield 31, while keeping a certain distance from the partial cylindrical conductor 41, in other words, on a virtual cylindrical surface sharing the central axis 910 with the RF shield 31. As in the case of the first embodiment, it is possible to configure the RF shield 31 and the partial cylindrical conductor 41 as a single unit.

The arrangement of the feeding ports and the connection with the high frequency signal divider/combiner 370, of the RF coil device 316 of the present embodiment, are similar to the connection aspects of the first embodiment as shown in FIG. 5. In other words, though not illustrated in FIG. 23A and FIG. 23B, the partial cylindrical coil 53A is provided with the first feeding port, the partial cylindrical coil 53B is provided with the second feeding port, the partial cylindrical coil 53C is provided with the third feeding port, the partial cylindrical coil 53D is provided with the fourth feeding port, and those coils respectively receive a supply of high frequency signals from the high frequency signal divider/combiner 370. Each of the feeding ports is arranged at the position where the first capacitor 71 becomes caught in the feeding port, as in the case of the first embodiment. However, in the present embodiment, as shown in FIG. 22, the high frequency signal divider/combiner 370 is connected to the transmitter 330 without passing through the transmit/receive switching unit 320, and receives an input of high frequency signals from the transmitter 330.

Figure 24A:
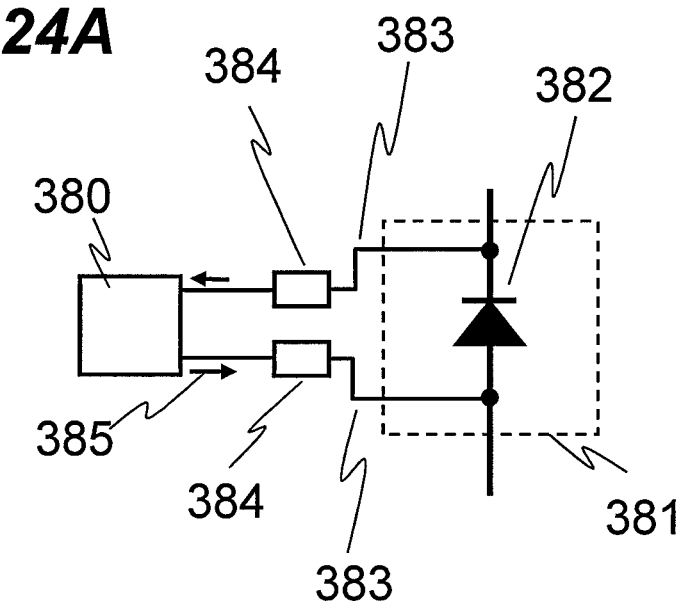
FIG. 24A illustrates a configuration and connection of a detune circuit of the RF coil device according to the fourth embodiment.

As shown in FIG. 24A, the detune circuit 381 is provided with a PIN diode 382 and a control line 383. The PIN diode 382 has the property that it becomes almost conduction state when a value of DC current flowing in a forward direction of the diode is a constant value or higher, and the DC current controls ON/OFF switching. Both ends of the PIN diode 382 are connected to the control line 383. The PIN diode 382 is connected to the output terminal of the detune circuit driver 380, via the control line 383 and the choke coils 384 which electrically insulate the high frequency signals. The ON/OFF switching of the PIN diode 382 is controlled by the control current 385 from the detune circuit driver 380.

When the detune signal is applied from the detune circuit driver 380, the control current 385 turns on all the PIN diodes 382 (conduction state), and the RF coil device 316 shows an electrical property similar to that of the RF coil device 311 as shown in FIG. 3A and FIG. 3B. On the other hand, when output of the detune signal from the detune circuit driver 380 is suspended, the value of the control current 385 becomes zero. When the PIN diode 382 is switched to the OFF state in the RF coil device 316, the first conductor 61 becomes nearly open state. Consequently, almost no current flows in the RF coil device 316. Therefore, no resonance occurs in the RF coil device 316 by the magnetic resonance frequency set at the MRI apparatus 101, and almost no high frequency magnetic field is generated.

Figure 25A:
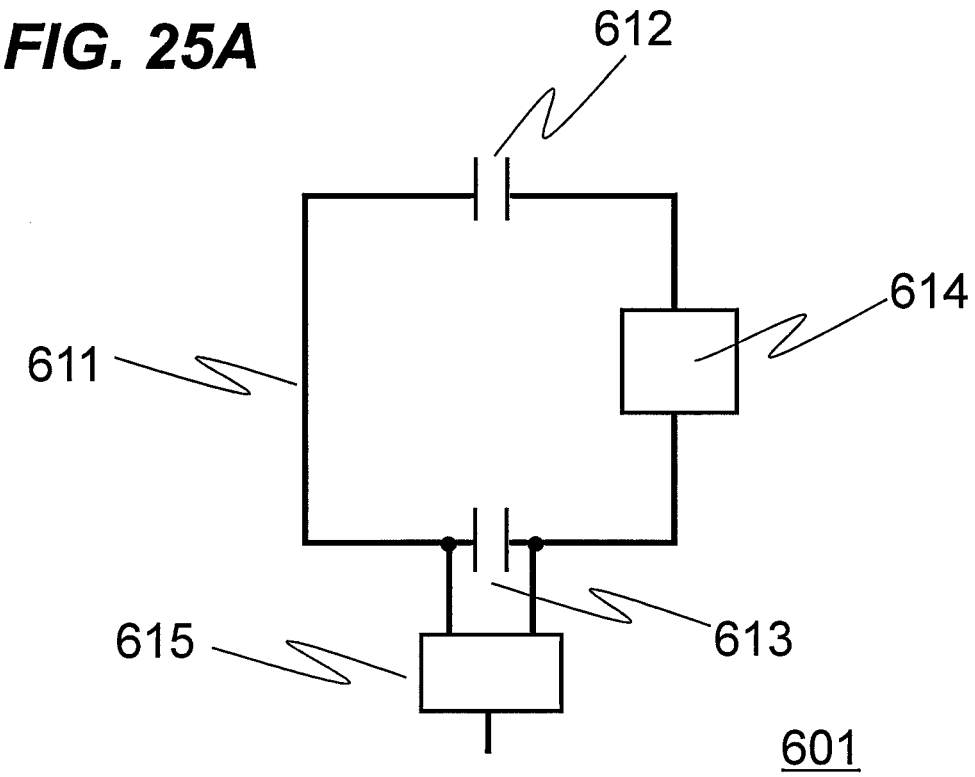
FIG. 25A illustrates a surface coil according to the fourth embodiment.
Figure 25B:
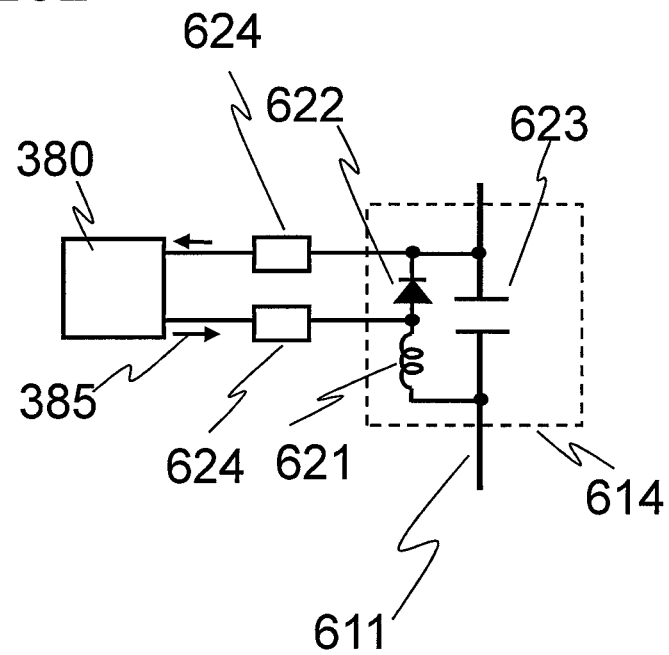
FIG. 25B illustrates a configuration and connection of the detune circuit of the surface coil.

Next, an explanation will be made as to the receive RF coil 360 of the present embodiment. In the present embodiment, the surface coil 601 is used as the receive RF coil 360 as illustrated in FIG. 25A and FIG. 25B. As shown in FIG. 25A, the surface coil 601 is provided with a loop conductor 611, a capacitor 612, a matching capacitor 613, a detune circuit 614, and a preamplifier 615. The capacitor 612, the matching capacitor 613, and the detune circuit 614 are inserted into the loop conductor 611. Wiring is disposed at both ends of the matching capacitor 613, and they are connected to the preamplifier 615.

As shown in FIG. 25B, the detune circuit 614 is provided with a circuit where the inductor 621 and a PIN diode 622 are serially connected, and the capacitor 623 connected to the circuit in parallel. The PIN diode 622 has the property that it becomes almost conduction state, when a value of DC current flowing in a forward direction of the diode is a constant value or higher, and the DC current controls ON/OFF switching. Both ends of the PIN diode 622 are connected to the output terminal of the detune circuit driver 380 via the choke coil 624.

The capacitor 612, the capacitor 623, and the matching capacitor 613 are adjusted in such a manner that the surface coil 601 produces resonance by the magnetic resonance frequency set in the MRI apparatus 101 of the present embodiment, and the impedance of the coil viewed from both ends of the matching capacitor 613 becomes a predetermined value. The detune circuit 614 is adjusted in such a manner that when the PIN diode 622 is ON state, resonance occurs in the inductor 621 and the capacitor 623, by the magnetic resonance frequency set at the MRI apparatus 101.

In the surface coil 601, when a detune signal is applied from the detune circuit driver 380, the control current 385 switches the PIN diode 622 to the ON state (conduction state), and the detune circuit 614 becomes a parallel resonance circuit made up of the inductor 621 and the capacitor 623. The impedance of this parallel resonance circuit becomes high by the magnetic resonance frequency set in the MRI apparatus 101, and the loop conductor 611 of the surface coil 601 becomes nearly open state. Consequently, resonance does not occur in the surface coil 601 by the magnetic resonance frequency set at the MRI apparatus 101, and almost no current flows in the loop conductor 611.

On the other hand, when output of the detune signal from the detune circuit driver 380 is suspended, the value of the control current 385 becomes zero in the surface coil 601. Then, the PIN diode 622 is switched to the OFF state, and the detune circuit 614 operates as the capacitor 623. Consequently, resonance occurs in the surface coil 601 by the magnetic resonance frequency set in the MRI apparatus 101.

Next, an explanation will be made as to the control by the detune circuit driver 380 using the detune signal.

Immediately before applying high frequency signals from the transmitter 330, the detune circuit driver 380 applies detune signals to the RF coil device 316 and the surface coil 601. Then, the RF coil device 316 operates as the transmit RF coil 350, as in the case of the RF coil device 311. On this occasion, almost no current flows in the loop conductor 611 of the surface coil 601, and the RF coil device 316 and the surface coil 601 come into the status that no magnetic coupling occurs therebetween.

Therefore, according to the detune signal applied at the aforementioned timing, the RF coil device 316 is allowed to irradiate the test subject 10 with the high frequency magnetic field, without a shift of resonance frequency nor reduction of Q value of the coil caused by the magnetic coupling. On this occasion, as described above, if all the PIN diodes 382 are switched to the ON state, the RF coil device 316 operates in the same manner as the RF coil device 311. Therefore, as in the case of the first embodiment, the transmit RF coil 350 that has received the signals as described above, irradiates the test subject 10 with the high frequency magnetic field, in the similar manner as the QD method.

On the other hand, upon receiving nuclear magnetic resonance signals emitted from the test subject 10, the detune circuit driver 380 suspends output of the detune signal to the RF coil device 316 and to the surface coil 601. Then, almost no current flows in the RE coil device 316, and no high frequency magnetic field is generated. As for the surface coil 601, resonance occurs by the magnetic resonance frequency set at the MRI apparatus 101.

Therefore, upon receiving the nuclear magnetic resonance signals emitted from the test subject 10, the magnetic coupling disappears between the surface coil 601 and the RE coil device 316, and the surface coil 601 is able to receive the nuclear magnetic resonance signals with high sensitivity, without the shift of resonance frequency nor reduction of Q value of the coil caused by the magnetic coupling. The signal received by the surface coil 601 is amplified by the preamplifier 615, and transferred to the receiver 340.

As explained so far, by controlling the output from the detune circuit driver 380, the RF coil device 316 as shown in FIG. 23A and FIG. 23B is allowed to operate as a coil for performing irradiation of the high frequency magnetic field in the same method as the QD method, and the surface coil 601 as shown in FIG. 25A and FIG. 25B is allowed to operate as the receive RF coil 360.

As described above, according to the present embodiment, upon applying the high frequency magnetic field, the impedance of the surface coil 601 (receive RF coil 360) is made much higher, and upon receiving the nuclear magnetic resonance signal, the impedance of the RE coil device 316 (transmit RF coil 350) is made much higher, thereby preventing the magnetic coupling between the transmit RF coil 350 and the receive RF coil 360, in which resonance occurs by the magnetic resonance frequency. Then, the RF coil device 316 is allowed to perform irradiation as in the case of the RF coil device 311 of the first embodiment.

Therefore, according to the present embodiment, even when the transmit RF coil 350 and the receive RF coil 360 are provided separately, or even when the shape of the transmit RF coil 350 is different from the shape of the receive RF coil 360 as described above, it is possible to obtain the effect similar to the first embodiment. In other words, according to the present embodiment, it is possible to expand the examination space which accommodates the test subject, without enlarging the inner diameter of the magnet or the gradient magnetic field coil. This enables the irradiation according to the QD method (QD irradiation), achieving the irradiation strength and homogeneity of irradiation distribution being comparable with a conventional cylindrical RF coil. Therefore, according to the present embodiment, in the tunnel type MRI apparatus, it is possible to provide a transmission coil which is able to reserve wide examination space, without significantly lowering the irradiation efficiency and the homogeneity in the irradiation distribution within a desired imaging region, nor enlarging the inner diameter of the magnet or the gradient magnetic field coil, relative to the birdcage coil.

According to the present embodiment, it is possible to select the shape of the transmit RF coil 350 and the shape of the receive RF coil 360, independently. By way of example, as explained in the aforementioned embodiment, it is possible to use the RF coil device 316 as the transmit RF coil 350, having wider examination space accommodating the test subject 10 and being able to performing irradiation of homogeneous high frequency magnetic field. In addition, it is possible to use the surface coil 601 as the receive RF coil 360, which is able to be placed near the test subject 10, allowing a highly sensitive receiving of the nuclear magnetic resonance signal. Therefore, according to the present embodiment, the test subject 10 is provided with a sense of openness, and imaging of a magnetic resonance image is possible which is optimized for individual test subject 10.

The shape of the RF coil device 316 is not limited to the example as described above. Any coil is applicable as far as the detune circuit 381 is able to be placed and it is controllable so that no interference occurs with the receive RF coil 360. By way of example, it may be a configuration similar to the RF coil device 312 being a modification example of the first embodiment. Alternatively, it may be the same configuration as the RF coil devices 313, 314, or 315, according to the second embodiment and its modification examples. Further alternatively, it may be the RF coil device as a modification example of those devices above.

The shape of the receive RF coil 360 is not limited to the example as described above. Any coil is applicable as far as the detune circuit 614 is placed and it is controllable so that no interference occurs with the transmit RF coil 350. By way of example, it may be an array boil on which the surface coil 601 is configured in the form of array, or a birdcage coil.

Figure 24B:
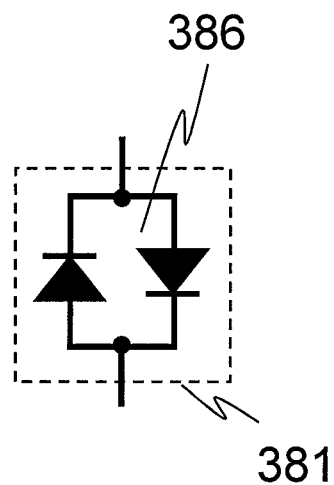
FIG. 24B illustrates an alternative example of the detune circuit.

In the RF coil device 316, the PIN diode 382 is employed for the detune circuit 381, but the detune circuit 381 is not limited to this example. By way of example, instead of the PIN diode 382, the cross diode 386 as shown in FIG. 24B may be employed. The cross diode 386 is turned on by the high frequency signal applied by the RF coil device 316, coming into the conduction state, and upon suspension of the high frequency signal application, it is turned off and becomes high resistive state. This operation is the same as the operation of the PIN diode 382. By using the cross diode 386, even without the control by the detune circuit driver 380, the RF coil device 316 operates as the transmit RF coil 350, without occurrence of magnetic coupling between the RF coil device 316 and the surface coil 601.

Figure 26A:
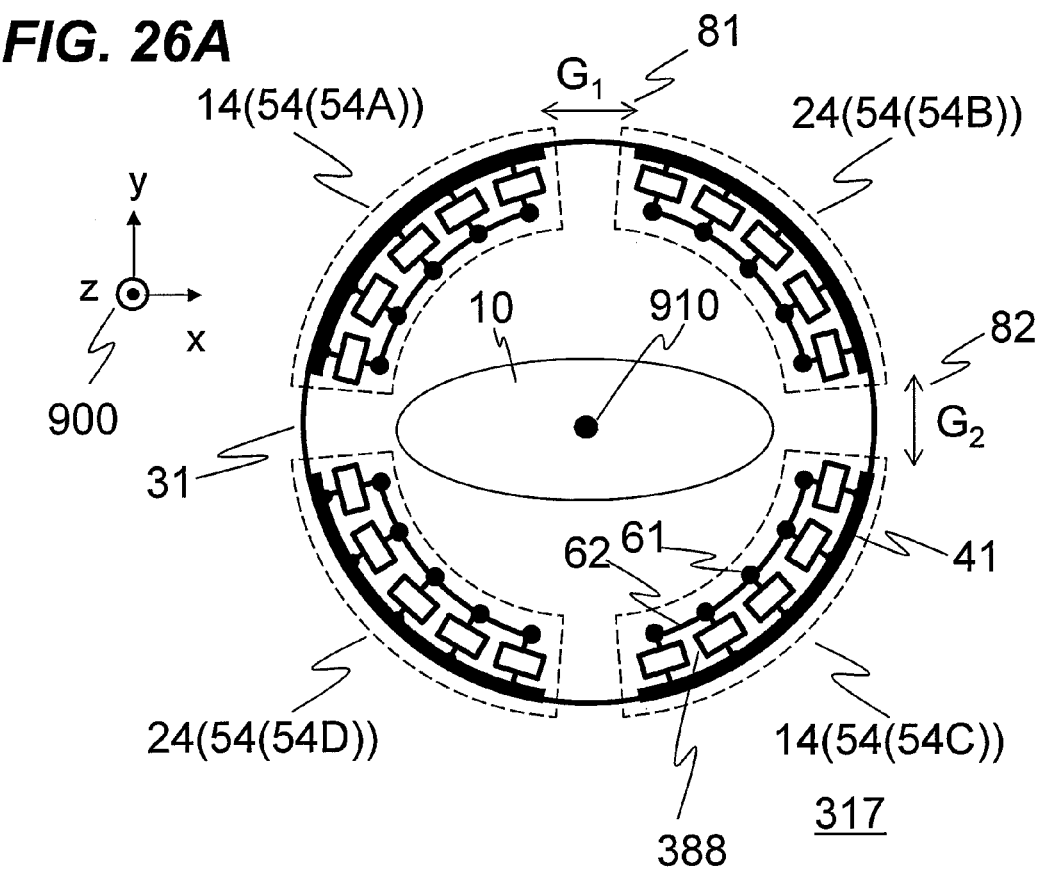
FIG. 26A illustrates a modification example of the RF coil device according to the fourth embodiment, and shows the RF coil device viewed in the central axis direction.
Figure 26B:
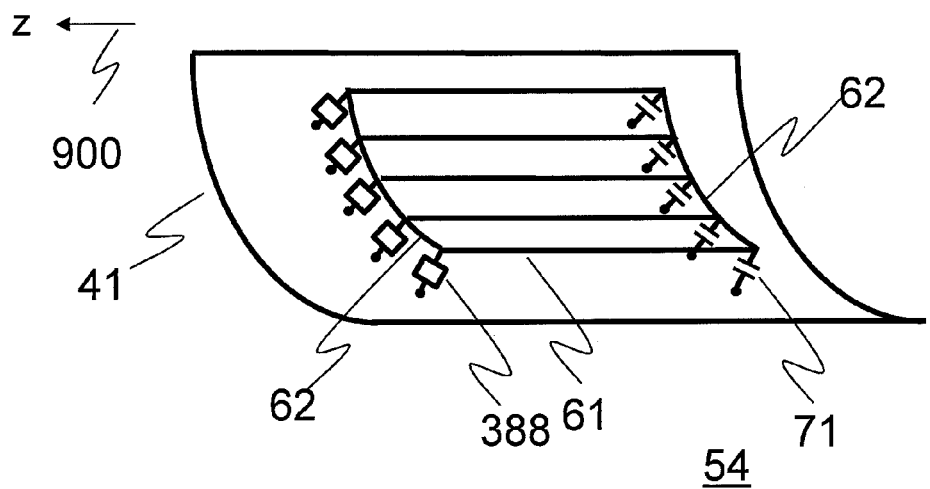
FIG. 26B illustrates a modification example of the RF coil device according to the fourth embodiment, and shows the partial cylindrical coil being a constitutional element of the RF coil device, viewed at an oblique angle.

The RF coil device of the present embodiment may be configured in such a manner that a detune circuit is provided instead of the first capacitor 71. In this case, the detune circuit 381 is not provided on the first conductor 61. FIG. 26A and FIG. 26B show the RF coil device 317 for this case. FIG. 26A illustrates the RF coil device 317 viewed in the direction of the central axis 910, and FIG. 26B illustrates the partial cylindrical coil 54 viewed at an oblique angle, being a constitutional element of the first RF coil 14 and the second RF coil 24. In here, an explanation will be made as to an example where only the first capacitor 71 on one side is replaced by the detune circuit 381, with regard to the first capacitor connecting both ends of each first conductor 61 with the partial cylindrical conductor 41, but the first capacitors 71 on both sides may be replaced by the detune circuits 381. In other words, it is only required that the detune circuit substitutes for the first capacitor 71 at least on one side.

The RF coil device 317 has configuration approximately the same as the RF coil device 311 as shown in FIG. 3A and FIG. 3B. In other words, the RF coil device 317 is provided with the first RF coil 14, the second RF coil 24, and the RF shield 31. As shown in FIG. 26A, the RF shield 31 is made up of the circular cylindrical conductor of a size accommodating the test subject 10. The arrangements of the first RF coil 14 and the second RF coil 24 are the same as those of the first RF coil 11 and the second RF coil 21 of the first embodiment.

The first RF coil 14 is provided with two partial cylindrical coils 54 (54A and 54C), arranged at the opposed positions placing the central axis 910 therebetween along the circumferential direction inside the RF shield 31. The second RF coil 24 is provided with two partial cylindrical coils 54 (54B and 54D), arranged at the opposed positions placing the central axis 910 therebetween along the circumferential direction inside the RF shield 31.

As shown in FIG. 26B, the partial cylindrical coil 54 is provided with the partial cylindrical conductor 41, multiple first conductors 61 substantially parallel to the central axis 910, multiple first capacitors 71 connecting the ends on one side of the first conductor 61 with the partial cylindrical conductor 41, and multiple second conductors 62 connecting both ends of the first conductor 61 with both ends of the adjacent first conductor 61 respectively. The partial cylindrical coil 54 of the RF coil device 317 is provided with the detune circuits 388 instead of the first capacitors 71, on the ends on the other side of the partial cylindrical coil 54. FIG. 26B illustrates the example that there are five first conductors 61, five first capacitors 71, eight second conductors 62, and five detune circuits 388, but the number of lines and the number units are not limited to those numbers.

The partial cylindrical conductor 41 is placed in such a manner that it comes into contact with the inside surface (inner wall) of the RF shield 31. The first conductors 61 are placed with equal spacing in the circumferential direction of the RF shield 31, while keeping a certain distance from the partial cylindrical conductor 41, in other words, on a virtual cylindrical surface sharing the central axis 910 with the RF shield 31.

The arrangement of each feeding port and connection with the high frequency signal divider/combiner 370, of the RF coil device 317, are similar to those of the aforementioned RF coil device 317. In other words, though not illustrated in FIG. 26A and FIG. 26B, the partial cylindrical coil 54A is provided with the first feeding port, the partial cylindrical coil 54B is provided with the second feeding port, the partial cylindrical coil 54C is provided with the third feeding port, the partial cylindrical coil 54D is provided with the fourth feeding port, and those coils respectively receive a supply of high frequency signals from the high frequency signal divider/combiner 370. Each feeding port is arranged at the position where the first capacitor 71 becomes caught in the feeding port, as in the case of the first embodiment. However, in the present embodiment, as shown in FIG. 22, the high frequency signal divider/combiner 370 is connected to the transmitter 330 without passing through the transmit/receive switching unit 320, and receives an input of high frequency signal from the transmitter 330.

Figure 27:
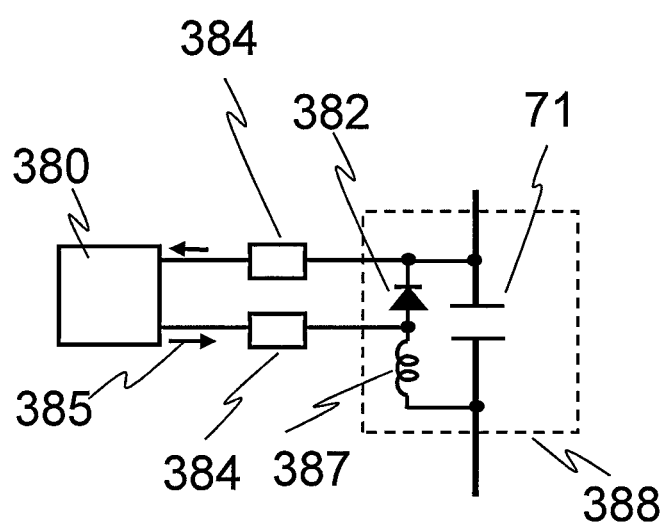
FIG. 27 illustrates a configuration and connection of the detune circuit of the modification example of the RF coil device according to the fourth embodiment.

As shown in FIG. 27, the detune circuit 388 is provided with a circuit in which an inductor 387 and a PIN diode 382 are serially connected, and the first capacitors 71 connected with the circuit in parallel. Both ends of the PIN diode 382 are connected to the output terminal of the detune circuit driver 380 via the choke coil 384.

The detune circuit 388 becomes open state, when the PIN diode 382 is in the ON state, whereas it operates as the first capacitor 71 when it is in the OFF state. Therefore, when the PIN diode 382 is switched to the OFF state, the RF coil device 317 shows the electrical property as in the case of the RF coil device 311 as shown in FIG. 3A and FIG. 3B.

Immediately before the transmitter 330 applies high frequency signals for the irradiation of the high frequency magnetic field, the detune circuit driver 380 sets the value of the control current 385 to be zero in such a manner that the PIN diode 382 of the detune circuit 388 is switched to the OFF state. Accordingly, upon irradiation of the high frequency magnetic field, the RF coil device 317 operates as the transmit RF coil 350.

After the irradiation of the high frequency magnetic field, the detune circuit driver 380 allows the control current 385 to flow to the detune circuit 388 in such a manner that the PIN diode 382 is switched to be the ON state. Accordingly, the detune circuit 388 of the partial cylindrical coil 54 as shown in FIG. 26B is nearly open state, and no more resonance occurs in the RF coil device 317 by the magnetic resonance frequency set in the MRI apparatus 101. Therefore, there is no more magnetic coupling between the surface coil 601 and the RF coil device 317, and the surface coil 601 is allowed to receive a nuclear magnetic resonance signal without a shift of resonance frequency nor lowering of Q value caused by the magnetic coupling.

Also in the present embodiment, as in the case of the first embodiment, the RF shield 31 and the partial cylindrical conductor 41 are only required to have the thickness and structure allowing the gradient magnetic field to pass through, while being shielded against the high frequency magnetic field. As in the case of the first embodiment, various modifications are available.

<<Fifth Embodiment>>

Next, a fifth embodiment to which the present invention is applied will be explained. The MRI apparatus of the present embodiment is basically the same as the first embodiment. However, there is a difference in the point that the RF coil device used as the transceive coil 310 is provided with a capacitor for preventing eddy current on the second conductor 62 of the partial cylindrical coil. Hereinafter, an explanation will be made focusing on the configuration which is different from the first embodiment. Also in the present embodiment, the orientation of the static magnetic field 920 generated by the horizontal magnetic field type magnet 110 corresponds to the z-axis direction of the coordinate system 900.

Figure 28A:
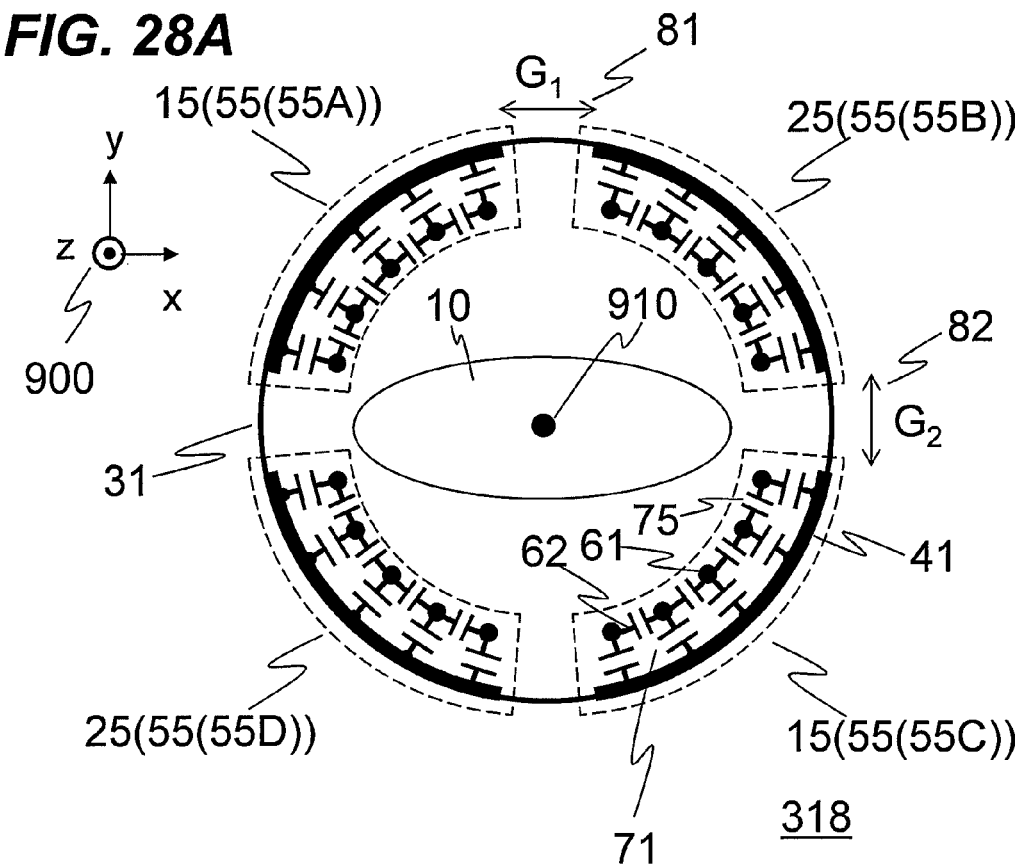
FIG. 28A illustrates the RF coil device according to a fifth embodiment, and shows the RF coil device viewed in the central axis direction.
Figure 28B:
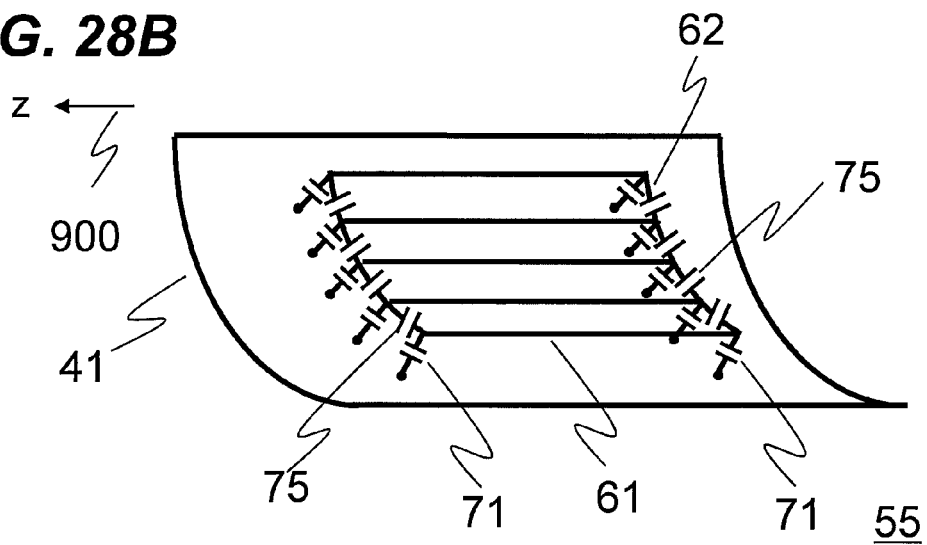
FIG. 28B illustrates the RF coil device according to a fifth embodiment, and shows the partial cylindrical coil being a constitutional element of the RF coil device, viewed at an oblique angle.

FIG. 28A and FIG. 28B illustrates a configuration of the RF coil device 318 of the present embodiment. This RF coil device 318 is used as the transceive coil 310 as shown in FIG. 2. FIG. 28A illustrates the RF coil device viewed in the central axis direction 910, and FIG. 28B illustrates the partial cylindrical coil 55 viewed at an oblique angle, constituting the first RF coil and the second RF coil of the RF coil device 318.

The RF coil device 318 has a configuration approximately the same as the RF coil device 311 as shown in FIG. 3A and FIG. 3B. In other words, the RF coil device is provided with the first RF coil 15, the second RF coil 25, and the RF shield 31. As shown in FIG. 28A, the RF shield 31 is made up of a circular cylindrical conductor of a size accommodating the test subject 10. The arrangements of the first RF coil 15 and the second RF coil 25 are the same as those of the first RF coil 11 and the second RF coil 21 according to the first embodiment.

The first RF coil 15 is provided with two partial cylindrical coils 55 (55A and 55C) which are arranged at the opposed positions placing the central axis 910 therebetween along the circumferential direction inside the RF shield 31. The second RF coil 25 is provided with two partial cylindrical coils 55 (55B and 55D) which are arranged at the opposed positions placing the central axis 910 therebetween along the circumferential direction inside the RF shield 31.

As shown in FIG. 28B, the partial cylindrical coil 55 is provided with the partial cylindrical conductor 41, multiple first conductors 61 substantially parallel to the central axis 910, multiple first capacitors 71 connecting both ends of the first conductors 61 with the partial cylindrical conductor 41, and multiple second conductors 62 connecting both ends of the first conductor 61 with both ends of the adjacent first conductor 61 respectively.

The partial cylindrical coil 55 of the present embodiment is further provided with a fourth capacitor 75 for preventing eddy current. This fourth capacitor 75 is inserted on the second conductor 62. A value of the fourth capacitor 75 is adjusted in such a manner as indicating a high resistive state in the frequency region of eddy current generated upon switching the gradient magnetic field that is produced by the gradient magnetic field coil 210, and indicating a short-circuited state in the operating frequency of the partial cylindrical coil 55.

FIG. 28B illustrates an example that there are five first conductors 61, ten first capacitors 71, eight second conductors 62, and eight fourth capacitors 75, but the number of lines and the number of units are not limited to those numbers.

Also in the present embodiment, the partial cylindrical conductor 41 is placed in such a manner as coming into contact with the inside surface (inner wall) of the RF shield 31. The first conductors 61 are placed with equal spacing in the circumferential direction of the RF shield 31, keeping a certain distance from the partial cylindrical conductor 41, in other words, on a virtual cylindrical surface sharing the central axis 910 with the RF shield 31. As in the case of the first embodiment, the RF shield 31 and the partial cylindrical conductor 41 may be configured as a single unit.

The arrangement of feeding ports and connection with the transmitter 330 and the receiver 340 via the high frequency signal divider/combiner 370 and the transmit/receive switching unit 320, of the RF coil device 318 of the present embodiment, are similar to the connection aspects of the first embodiment as shown in FIG. 5. In other words, though not illustrated in FIG. 28A and FIG. 28B, the partial cylindrical coil 55A is provided with the first feeding port, the partial cylindrical coil 55B is provided with the second feeding port, the partial cylindrical coil 55C is provided with the third feeding port, and the partial cylindrical coil 55D is provided with the fourth feeding port, and each of those coils receives a supply of high frequency signals, and detects the high frequency magnetic field being generated. Each feeding port is arranged at the position where the first capacitor 71 becomes caught in the feeding port, as in the case of the first embodiment.

When the gradient magnetic field applied from the gradient magnetic field coil 210 is switched, a change in magnetic field causes eddy current in the loop conductor made up of only conductors. In an imaging sequence such as an echo planar imaging, in which the orientation of the gradient magnetic field is switched periodically, image distortion or artifact may occur, in some cases, due to the magnetic field generated by the eddy current upon switching.

As described above, the RF coil device 318 of the present embodiment is provided with the fourth capacitor 75 that is adjusted in such a manner as indicating high resistivity in the frequency region of the eddy current, and a short-circuited state in the operating frequency of the partial cylindrical coil 55. Therefore, in the RF coil device 318 of the present embodiment, the fourth capacitor 75 becomes highly resistive in the frequency region of the eddy current generated upon switching the gradient magnetic field, and thus it is possible to prevent the eddy current from flowing on the conductor loop which is made up of adjacent two first conductors 61 and second conductors 62. Therefore, occurrence of image distortion or artifact due to the eddy current can be prevented.

Since the RF coil device 318 of the present embodiment is the same as the RF coil device 311 of the first embodiment, other than the configuration of the fourth capacitor 75, the RF coil device 318 operates in its operation frequency in the same manner as the RF coil device 311 of the first embodiment. Therefore, the RF coil unit provided with the RF coil device 318 of the present embodiment operates as the transceive coil 310 which irradiates the test subject 10 with a high frequency magnetic field, and detects the nuclear magnetic resonance signal generated from the test subject 10 to output the signal as a detection signal.

As explained so far, according to the present embodiment, it is possible to provide the transceive coil which produces the same effect as the first embodiment. Further, according to the present embodiment, it is possible to prevent generation of image distortion or artifact, thereby enhancing an image quality.

The present embodiment illustrates the case that the fourth capacitor 75 for preventing the eddy current is provided on the second conductor 62 of the partial cylindrical coil 55, but the location for inserting the fourth capacitor 75 is not limited this position. As described above, it is only required to prevent the eddy current from flowing on the conductor loop made up of the adjacent two first conductors 61 and the second conductors 62, and thus the fourth capacitor may be inserted on the first conductor 61, for instance. In other words, it may be inserted on at least one of the first conductor 61 and the second conductor 62.

In the present embodiment, an explanation has been made taking an example that the RF coil devices 311 and 312 of the first embodiment are provided with the fourth capacitor 75, but the RF coil device provided with the fourth capacitor 75 is not limited to this example. It may be the RF coil device 313 of the second embodiment, or the RF coil device 314 or 315 of the third embodiment. Alternatively, it may be the RF coil device 316 or 317 of the fourth embodiment.

Also in the present embodiment, as in the case of the first embodiment, it is only required that the RF shield 31 and the partial cylindrical conductor 41 have a thickness and structure allowing the gradient magnetic field to pass through, while shielded against the high frequency magnetic field. In addition, as in the case of the first embodiment, various modifications are possible.

According to each of the foregoing present embodiments, it is possible to provide the RE coil in which the examination space accommodating a test subject is expanded without enlarging the inner diameter of the magnet or the gradient magnetic field coil, thereby achieving a homogeneous irradiation distribution within the test subject and allowing irradiation of the high frequency magnetic field of a circular or elliptic circular polarized wave. With the RF coil as described so far, it is possible to configure an MRI apparatus which provides a sense of openness, and an MRI apparatus which reserves installation space for various equipment within the examination space.

EXPLANATION OF REFERENCES

10: test subject, 11: first RF coil, 12: first RF coil, 13: first RF coil, 14: first RF coil, 15: first RF coil, 21: second RF coil, 22: second RF coil, 23: second RF coil, 24: second RF coil, 25: second RF coil, 31: RF shield, 32: RF shield, 41: partial cylindrical conductor, 42: partial elliptic cylindrical conductor, 51: partial cylindrical coil, 52: partial elliptic cylindrical coil, 53: partial cylindrical coil, 54: partial cylindrical coil, 55: partial cylindrical coil, 61: first conductor, 62: second conductor, 63: loop conductor, 64: conductor loop, 71: first capacitor, 72: second capacitor, 73: third capacitor, 74: adjusting inductor, 75: fourth capacitor, 81: first gap, 82: second gap, 83: first gap, 84: second gap, 88: space, 89: space, 91: RF current, 92: high frequency magnetic field, 93: flux, 94: inductive current, 95: RF current, 96: high frequency magnetic field, 97: first flux, 98: second flux, 100: MRI apparatus, 101: MRI apparatus, 110: magnet, 120: patient table, 210: gradient magnetic field coil, 220: shim coil, 230: power supply for gradient magnetic field, 240: power supply for shim coil, 301: RF coil unit, 310: transceive coil, 311: RF coil device, 312: RF coil device, 313: RF coil device, 314: RF coil device, 315: RF coil device, 316: RF coil device, 317: RF coil device, 318: RF coil device, 320: transmit/receive switching unit, 330: transmitter, 340: receiver, 350: transmit RF coil, 360: receive RF coil, 370: high frequency signal divider/combiner, 371: QD hybrid, 372: first 0°-180° divider/combiner, 373: second 0°-180° divider/combiner, 374: feeding port, 380: detune circuit driver, 381: detune circuit, 382: PIN diode, 383: control line, 384: choke coil, 385: control current, 386: cross diode, 387: inductor, 388: detune circuit, 410: sequencer, 510: computer, 520: display, 530: storage memory, 601: surface coil, 611: loop conductor, 612: capacitor, 613: matching capacitor, 614: detune circuit, 615: preamplifier, 621: inductor, 622: PIN diode, 623: capacitor, 624: choke coil, 900: coordinate system, 910: central axis, 911: plane, 920: static magnetic field

What is claimed is:

1. A high frequency coil comprising:
a cylindrical RF shield, a first high frequency coil, and a second high frequency coil,
the first high frequency coil and the second high frequency coil being placed with a gap therebetween in a circumferential direction inside the RF shield, each of the first high frequency coil and the second high frequency coil being provided with two sheet-like partial cylindrical coils opposed to each other placing a central axis of the RF shield therebetween, and
each of the sheet-like partial cylindrical coils comprising:
a sheet-like partial cylindrical conductor sharing the central axis,
multiple first conductors being placed inside the sheet-like partial cylindrical conductor and substantially parallel to the central axis,
multiple first capacitors connecting both ends of the first conductors with the sheet-like partial cylindrical conductor, and
at least one second conductor establishing a short-circuit between at least one end of the first conductor and one end of an adjacent first conductor.

2. The high frequency coil according to claim 1, wherein, the RF shield has an elliptic cylindrical shape.

3. The high frequency coil according to claim 1, wherein, the RF shield has a circular cylindrical shape.

4. The high frequency coil according to claim 2, wherein, the first conductors are arranged in such a manner that a distance from an inner wall of the RF shield becomes shorter, along with being positioned away from the central axis of the elliptic cylindrical shape, in the long axis direction.

5. The high frequency coil according to claim 2, wherein, the first conductors are arranged in such a manner that a distance from an inner wall of the RF shield becomes equal.

6. The high frequency coil according to claim 1, wherein, the partial cylindrical conductor and the RF shield are structured as a single unit.

7. The high frequency coil according to claim 1, wherein, the RF shield and the partial cylindrical conductor has a structure allowing a gradient magnetic field to pass through, while being shielded against a high frequency magnetic field.

8. The high frequency coil according to claim 1, further comprising a magnetic coupling adjusting unit for adjusting magnetic coupling between the first high frequency coil and the second high frequency coil.

9. The high frequency coil according to claim 8, wherein,
the magnetic coupling adjusting unit comprises a conductor loop, at least one second capacitor being inserted therein,
the conductor loop each placed in one pair of gaps positioned axial-symmetrically with respect to the central axis, among multiple gaps between the first high frequency coil and the second high frequency coil, and
a value of the second capacitor is adjusted so as to prevent the magnetic coupling between the first high frequency coil and the second high frequency coil.

10. The high frequency coil according to claim 8, wherein,
the magnetic coupling adjusting unit comprises multiple magnetic coupling adjusting circuits, each including a third capacitor and an adjusting inductor being connected in series,
the magnetic coupling adjusting circuits are placed within one pair of gaps positioned axial-symmetrically with respect to the central axis, among multiple gaps between the first high frequency coil and the second high frequency coil,
the third capacitor is connected to the end of the first conductor,
the adjusting inductor is connected to the partial cylindrical conductor, being arranged in such a manner that the magnetic coupling occurs mutually between the adjusting inductors respectively connected to the first high frequency coil and the second high frequency coil, and
a value of mutual inductance of the adjusting inductors and a value of the third capacitor are adjusted so as to prevent the magnetic coupling between the first high frequency coil and the second high frequency coil.

11. The high frequency coil according to claim 1, wherein,
a capacitor for preventing eddy current for blocking the eddy current generated by a gradient magnetic field but allowing RF current to pass through, is inserted in at least one of the first conductor and the second conductor.

12. The high frequency coil according to claim 3, wherein,
all the gaps between the first high frequency coil and the second high frequency coil, provided in the circumferential direction, are equal.

13. The high frequency coil according to claim 1, wherein,
the first high frequency coil and the second high frequency coil each comprises a detune unit for switching between operation and non-operation of the high frequency coil, according to a predetermined signal.

14. The high frequency coil according to claim 13, wherein,
the detune unit comprises a PIN diode.

15. The high frequency coil according to claim 13, wherein,
the detune unit is a circuit formed by connecting a capacitor in parallel with a circuit in which a PIN diode and an inductor are serially connected.

16. A magnetic resonance imaging apparatus comprising:
a static magnetic field forming unit for forming a static magnetic field,
a gradient magnetic field forming unit for forming a gradient magnetic field,
a high frequency magnetic field forming unit for forming a high frequency magnetic field,
a transceive coil for applying the high frequency magnetic field to an examination target and detecting a nuclear magnetic resonance signal from the examination target,
a signal processing unit for processing the nuclear magnetic resonance signal detected by the transceive coil,
a control unit for controlling operations of the gradient magnetic field forming unit, the high frequency magnetic field forming unit, and the signal processing unit, wherein,
the transceive coil comprises:
the high frequency coil according to claim 1, and
a high frequency signal control unit, wherein, the high frequency signal control unit further comprises:
a first signal dividing and combining unit, and two second signal dividing and combining unit respectively connected to the first high frequency coil and the second high frequency coil, and
the first signal dividing and combining unit supplies high frequency signals having a phase difference of 90 degrees, respectively to the two second signal dividing and combining unit, and combining the high frequency signals respectively supplied from the two second signal dividing and combining unit, by shifting the phase of one signal by 90 degrees, and
the second signal dividing and combining unit supplies the high frequency signals having the phase difference of 180 degrees to two partial cylindrical coils of each of the first high frequency coil and the second high frequency coil, respectively, and combines the signals supplied from the two partial cylindrical coils by shifting the phase of one signal by 180 degrees.

17. A magnetic resonance imaging apparatus comprising:
a static magnetic field forming unit for forming a static magnetic field,
a gradient magnetic field forming unit for forming a gradient magnetic field,
a high frequency magnetic field forming unit for forming a high frequency magnetic field,
a transmit coil for applying the high frequency magnetic field to an examination target,
a receive coil for detecting a nuclear magnetic resonance signal from the examination target,
a signal processing unit for processing the nuclear magnetic resonance signal detected by the receive coil,
a control unit for controlling operations of the gradient magnetic field forming unit, the high frequency magnetic field forming unit, and the signal processing unit, wherein, the transmit coil comprises:
the high frequency coil according to claim 13, and
a high frequency signal control unit, wherein,
the high frequency signal control unit further comprises:
a first signal dividing and combining unit, and two second signal dividing and combining unit respectively connected to the first high frequency coil and the second high frequency coil, and
the first signal dividing and combining unit supplies high frequency signals having a phase difference of 90 degrees, respectively to the two second signal dividing and combining unit, and combining the high frequency signals respectively provided from the two second signal dividing and combining unit, by shifting the phase of one signal by 90 degrees, the second signal dividing and combining unit supplies the high frequency signals having the phase difference of 180 degrees to two partial cylindrical coils of each of the first high frequency coil and the second high frequency coil, respectively, and combines the signals supplied from the two partial cylindrical coils by shifting the phase of one signal by 180 degrees, and the receive coil further comprises a second detune unit for disabling operation of the receive coil according to the predetermined signal.

* * * * *